United States Patent
Cool et al.

(10) Patent No.: US 9,333,257 B2
(45) Date of Patent: May 10, 2016

(54) FGFR1 ANTIBODIES AND TREATMENT OF CANCER

(75) Inventors: Simon Cool, Singapore (SG); Victor Nurcombe, Singapore (SG); Ling Ling, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 211 days.

(21) Appl. No.: 14/004,913

(22) PCT Filed: Mar. 14, 2012

(86) PCT No.: PCT/SG2012/000085
§ 371 (c)(1),
(2), (4) Date: Nov. 26, 2013

(87) PCT Pub. No.: WO2012/125124
PCT Pub. Date: Sep. 20, 2012

(65) Prior Publication Data
US 2014/0086925 A1    Mar. 27, 2014

Related U.S. Application Data

(60) Provisional application No. 61/452,188, filed on Mar. 14, 2011.

(30) Foreign Application Priority Data

May 10, 2011 (SG) .................................. 201103325

(51) Int. Cl.
*A61K 39/395* (2006.01)
*C07K 16/28* (2006.01)

(52) U.S. Cl.
CPC ....... *A61K 39/39558* (2013.01); *C07K 16/2863* (2013.01); *C07K 2317/34* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 2007/0248605 A1* | 10/2007 | Hestir et al. | ............... | 424/139.1 |
| 2007/0274981 A1* | 11/2007 | Sun et al. | ................... | 424/130.1 |
| 2010/0047251 A1 | 2/2010 | Yayon et al. | | |
| 2011/0129524 A1* | 6/2011 | Imai et al. | ..................... | 424/450 |
| 2012/0141495 A1* | 6/2012 | Tsimafeyeu | ............... | 424/145.1 |

FOREIGN PATENT DOCUMENTS

| | | |
|---|---|---|
| EP | 2165715 | 3/2010 |
| WO | WO2005/066211 | 7/2005 |
| WO | WO2007/056604 | 5/2007 |

OTHER PUBLICATIONS

Duchesne et al., The Journal of Biological Chemistry vol. 281, No. 37, pp. 27178-27189, Sep. 15, 2006.*
Blanckaert et al., Partial characterization of endothelial FGF receptor functional domain by monoclonal antibody VBS—1, Hybridoma and Hybridomics, 21(3): 153-159 (2002).
Dombrowski et al., Heparan Sulfate Mediates the Proliferation and Differentiation of Rat Mesenchymal Stem Cells, Stem Cells and Development, 18(4): 661-670 (2009).
Johnson et al, The Human Fibroblast Growth Factor Receptor Genes: a Common Structural Arrangement Underlies the Mechanisms for Generating Receptor Forms that Differ in Their Third Immunoglobulin Domain, Molecular and Cellular Biology, 11(9): 4627-4634 (1991).
Kan et al., An Essential Heparin-Binding Domain in the Fibroblast Growth Factor Receptor Kinase, Science, 259: 1918-1921 (1993).
Karajannis et al., Activation of FGFRO signalling pathway promotes survival, migration and resistance to chemotherapy in acute myeloid leukemia cells, Leukemia, 20: 979-986 (2006).
Ling et al Sulfated Glycosaminoglycans Mediate the Effects of FGF2 on the Osteogenic Potential of Rat Calvarial Osteoprogenitor Cells, Journal of Cellular Physiology, 209: 811-825 (2006).
Ng et al., Osteogenic Differentiation of Murine Embryonic Stem Cells Is Mediates by Fibroblast Growth Factor Receptors, Stem Cells and Development, 16: 305-318 (2007).
Palamakumbura et al., Lysyl oxidase pro-peptide inhibits prostate cancer cell growth by mechanisms that target FGF-2-cell binding and signaling, Oncogene, 287(38): 3390-3400 (2009).
Ronca et al., Antiangiogenic activity of a neutralizing human single-chain antibody fragment against fibroblast growth factor receptor 1, Molecular Cancer Therapeutics, 9(12): 3244-3253 (2010).
Shen et al., FGF Signaling in Prostate Tumorigenesis—New Insights into Epithelial-Stromal Interactions, Cancer Cell,12: 495-497 (2007).
Xu et al., Expression and immunochemical analysis of rat and human fibroblast growth factor receptor (fig) isoforms, Journal of Biological Chemistry, 267(25), 17792-17803 (1992).
Yiangou et al., Down-regulation of a novel form of fibroblast growth factor receptor 1 in human breast cancer, British Journal of Cancer, 76(11): 1419-1427 (1997).
International Search Report and Written Opinion of PCT/SG2012/000085, dated May 30, 2012, 11 pages.
Ling, L. et al., Targeting the heparin-binding domain of fibroblast growth factor receptor 1 as a potential cancer therapy, Molecular Cancer, 14(136): 1-16 (2015); and Supplementary Data, pp. 17-21.

* cited by examiner

*Primary Examiner* — Ilia Ouspenski
(74) *Attorney, Agent, or Firm* — Choate, Hall & Stewart LLP; Charles E. Lyon; Michael L. Vetter

(57) ABSTRACT

The use of an FGFR1 antibody in the treatment of cancer is disclosed, wherein the FGFR1 antibody binds FGFR1 at an epitope that is positioned in the FGFR1 primary amino acid sequence no more than 50 contiguous amino acids away from the C- or N-terminal of the FGFR1 heparin binding domain.

17 Claims, 53 Drawing Sheets

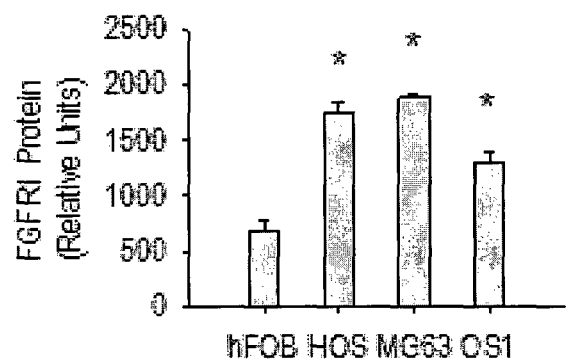
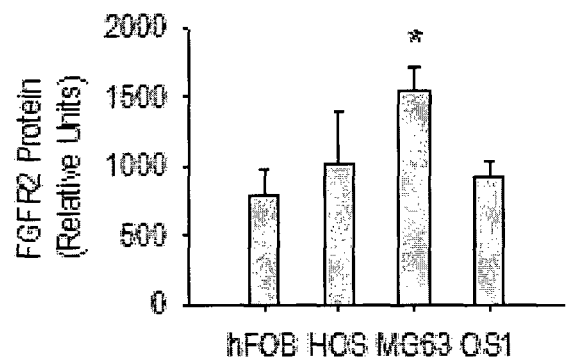
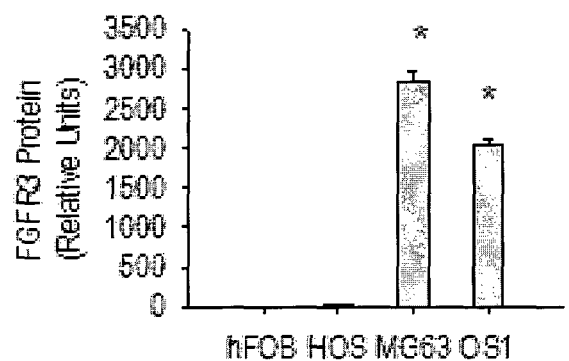
Figure 2E

IC50 ≈ 1:250
dilution in MG63

1 MWSWKCLLFW AVLVTATLCT ARPSPTLPEQ AQPWGAPVEV ESFLVHPGDL LQLRCRLRDD
61 VQSINWLRDG VQLAESNRTR ITGEEVEVQD SVPADSGLYA CVTSSPSGSD TTYFSVNVSD
121 ALPSSEDDDD DDDSSSEEKE TDNTKPNRMP VAPYWTSPEK MEKKLHAVPA AKTVKFKCPS
181 SGTPNPTLRW LKNGKEFKPD HRIGGYKVRY ATWSIIMDSV VPSDKGNYTC IVENEYGSIN
241 HTYQLDVVER SPHRPILQAG LPANKTVALG SNVEFMCKVY SDPQPHIQWL KHIEVNGSKI
301 GPDNLPYVQI LKTAGVNTTD KEMEVLHLRN VSFEDAGEYT CLAGNSIGLS HHSAWLTVLE
361 ALEERPAVMT SPLYLEIIIY CTGAFLISCM VGSVIVYKMK SGTKKSDFHS QMAVHKLAKS
421 IPLRRQVTVS ADSSASMNSG VLLVRPSRLS SSGTPMLAGV SEYELPEDPR WELPRDRLVL
481 GKPLGEGCFG QVVLAEAIGL DKDKPNRVTK VAVKMLKSDA TEKDLSDLIS EMEMMKMIGK
541 HKNIINLLGA CTQDGPLYVI VEYASKGNLR EYLQARRPPG LEYCYNPSHN PEEQLSSKDL
601 VSCAYQVARG MEYLASKKCI HRDLAARNVL VTEDNVMKIA DFGLARDIHH IDYYKKTTNG
661 RLPVKWMAPE ALFDRIYTHQ SDVWSFGVLL WEIFTLGGSP YPGVPVEELF KLLKEGHRMD
721 KPSNCTNELY MMMRDCWHAV PSQRPTFKQL VEDLDRIVAL TSNQEYLDLS MPLDQYSPSF
781 PDTRSSTCSS GEDSVFSHEP LPEEPCLPRH PAQLANGGLK RR

[SEQ ID NO:1]    GenBank Accession no: P11362.3 (GI:120046)

SSSEEKETDNTKPNR      [SEQ ID NO:2]

KMEKKLHAVPAAKTVKFK   [SEQ ID NO:3]

Figure 14

1 MWSWKCLLFW AVLVTATLCT ARPSPTLPEQ AQPWGAPVEV ESFLVHPGDL LQLRCRLRDD
61 VQSINWLRDG VQLAESNRTR ITGEEVEVQD SVPADSGLYA CVTSSPSGSD TTYFSVNVSD
121 ALPSSEDDDD DDDSSSEEKE TDNTKPNPVA PYWTSPEKME KKLHAVPAAK TVKFKCPSSG
181 TPNPTLRWLK NGKEFKPDHR IGGYKVRYAT WSIIMDSVVP SDKGNYTCIV ENEYGSINHT
241 YQLDVVERSP HRPILQAGLP ANKTVALGSN VEFMCKVYSD PQPHIQWLKH IEVNGSKIGP
301 DNLPYVQILK TAGVNTTDKE MEVLHLRNVS FEDAGEYTCL AGNSIGLSHH SAWLTVLEAL
361 EERPAVMTSP LYLEIIIYCT GAFLISCMVG SVIVYKMKSG TKKSDFHSQM AVHKLAKSIP
421 LRRQVTVSAD SSASMNSGVL LVRPSRLSSS GTPMLAGVSE YELPEDPRWE LPRDRLVLGK
481 PLGEGCFGQV VLAEAIGLDK DKPNRVTKVA VKMLKSDATE KDLSDLISEM EMMKMIGKHK
541 NIINLLGACT QDGPLYVIVE YASKGNLREY LQARRPPGLE YCYNPSHNPE EQLSSKDLVS
601 CAYQVARGME YLASKKCIHR DLAARNVLVT EDNVMKIADF GLARDIHHID YYKKTTNGRL
661 PVKWMAPEAL FDRIYTHQSD VWSFGVLLWE IFTLGGSPYP GVPVEELFKL LKEGHRMDKP
721 SNCTNELYMM MRDCWHAVPS QRPTFKQLVE DLDRIVALTS NQEYLDLSMP LDQYSPSFPD
781 TRSSTCSSGE DSVFSHEPLP EEPCLPRHPA QLANGGLKRR

[SEQ ID NO:4] GenBank Accession no: NP_056934.2 (GI:13186251)

HSGINSSDAE VLTLFNVTEA QSGEYVCKVS NYIGEANQSA WLTVTRP

[SEQ ID NO:5] GenBank Accession no: AAB19502.1 (GI:233769)

Figure 14 (cont'd)

MWSWKCLLFW AVLVTATLCT ARPSPTLPEQ AQPWGAPVEV ESFLVHPGDL LQLRCRLRDD
VQSINWLRDG VQLAESNRTR ITGEEVEVQD SVPADSGLYA CVTSSPSGSD TTYFSVNVSD
ALPSSEDDDD DDDSSSEEKE TDNTKPNPVA PYWTSPEKME KKLHAVPAAK TVKFKCPSSG
TPNPTLRWLK NGKEFKPDHR IGGYKVRYAT WSIIMDSVVP SDKGNYTCIV ENEYGSINHT
YQLDVVERSP HRPILQAGLP ANKTVALGSN VEFMCKVYSD PQPHIQWLKH IEVNGSKIGP
DNLPYVQILK HSGINSSDAE VLTLFNVTEA QSGEYVCKVS NYIGEANQSA WLTVTRP AL
EERPAVMTSP LYLEIIIYCT GAFLISCMVG SVIVYKMKSG TKKSDFHSQM AVHKLAKSIP
LRRQVTVSAD SSASMNSGVL LVRPSRLSSS GTPMLAGVSE YELPEDPRWE LPRDRLVLGK
PLGEGCFGQV VLAEAIGLDK DKPNRVTKVA VKMLKSDATE KDLSDLISEM EMMKMIGKHK
NIINLLGACT QDGPLYVIVE YASKGNLREY LQARRPPGLE YCYNPSHNPE EQLSSKDLVS
CAYQVARGME YLASKKCIHR DLAARNVLVT EDNVMKIADF GLARDIHHID YYKKTTNGRL
PVKWMAPEAL FDRIYTHQSD VVWSFGVLLWE IFTLGGSPYP GVPVEELFKL LKEGHRMDKP
SNCTNELYMM MRDCWHAVPS QRPTFKQLVE DLDRIVALTS NQEYLDLSMP LDQYSPSFPD
TRSSTCSSGE DSVFSHEPLP EEPCLPRHPA QLANGGLKRR

[SEQ ID NO:6]

Figure 14 (cont'd)

IIIb   -HSGINSSDAE--VLTLFNVTEAQSGEYVCKVSNYIGEANQSAWLTVTRP

IIIc   -TAGVNTTDKEMEVLHLRNVSFEDAGEYTCLAGNSIGLSHHSAWLTVLE

Figure 15

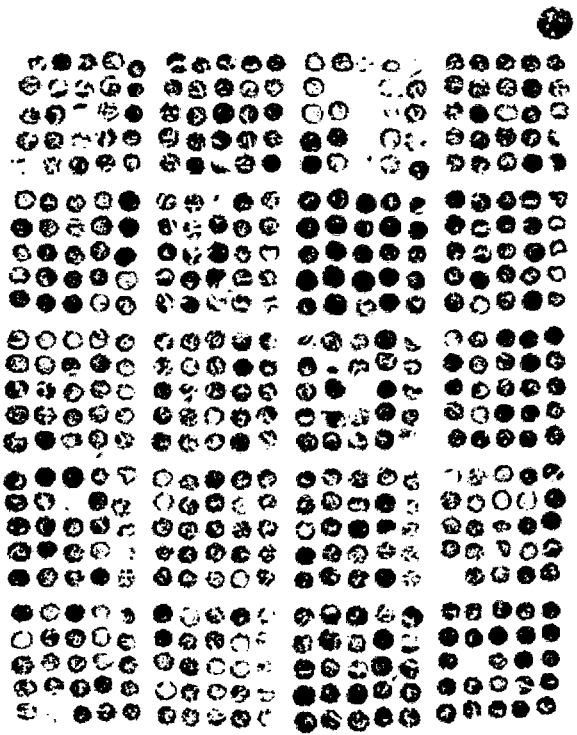
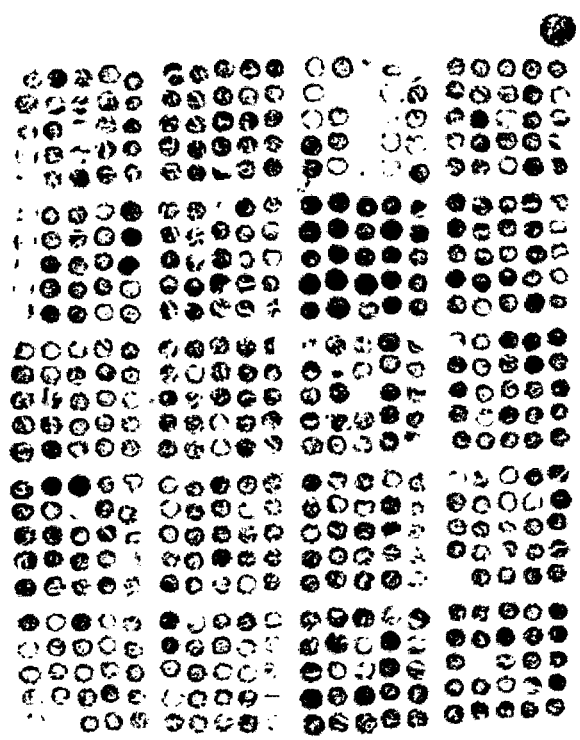
Figure 22

MG63:

FGFR1 ANTIBODIES AND TREATMENT OF CANCER

SEQUENCE LISTING

In accordance with 37 CFR §1.52(e)(5), a Sequence Listing in the form of a text file (entitled "Sequence_Listing.txt," created on Sep. 10, 2013 and 23 KB in size) is incorporated herein by reference in its entirety.

FIELD OF THE INVENTION

The present invention relates to FGFR1 antibodies and their use in the treatment of cancer.

BACKGROUND TO THE INVENTION

Signalling cascades generated from fibroblast growth factor receptors (FGFRs) have been established as key factors in the control of cell proliferation, migration, and differentiation for many types of cells (Fernig D and J T Gallagher. (1995). Fibroblast growth factors and their receptors: An information network controlling tissue growth morphogenesis and repair. Prog Growth Factor Res 5:353-377; Boilly B, A S Vercoutter-Edouart, H Hondermarck, V Nurcombe and X Le Bourhis. (2000). FGF signals for cell proliferation and migration through different pathways. Cytokine Growth Factor Rev 11:295-302; Marie P J. (2003). Fibroblast growth factor signalling controlling osteoblast differentiation. Gene 316:23-32. Eswarakumar V P, I Lax and J Schlessinger. (2005). Cellular signaling by fibroblast growth factor receptors. Cytokine Growth Factor Rev 16:139-149.).

Alternative splicing in the third immunoglobulin (Ig) loop of FGFR 1-3 transcripts result in a variety of isoforms, leading to differences in ligand binding specificity (Dell K R and L T Williams. (1992). A novel form of fibroblast growth factor receptor 2. Alternative splicing of the third immunoglobulin-like domain confers ligand binding specificity. J Biol Chem 267:21225-21229. Givol D and A Yayon. (1992). Complexity of FGF receptors: genetic basis for structural diversity and functional specificity. FASEB J 6:3362-3369.0), with the "b" and "c" isoforms generally expressed in epithelial and mesenchymal tissues, respectively Orr-Urtreger A, M T Bedford, T Burakova, E Arman, Y Zimmer, A Yayon, D Givol and P Lonai. (1993); Developmental localization of the splicing alternatives of fibroblast growth factor receptor-2 (FGFR2). Dev Biol 158: 475-486; Ornitz D M, J Xu, J S Colvin, D G McEwen, C A MacArthur, F Coulier, G Gao and M Goldfarb. (1996). Receptor specificity of the fibroblast growth factor family. J Biol Chem 271:15292-15297.).

Targeted disruptions of FGFRs have been shown to cause a variety of phenotypic abnormalities in mice, including embryonic lethality due to defective cell migration (FGFR1) (Partanen J, L Schwartz and J Rossant. (1998). Opposite phenotypes of hypomorphic and Y766 phosphorylation site mutations reveal a function for Fgfr1 in anteroposterior patterning of mouse embryos. Genes Dev 12:2332-2344.), impairment of bone and limb development (FGFR2) (Xu X, M Weinstein, C Li, M Naski, R I Cohen, D M Ornitz, P Leder and C Deng. (1998). Fibroblast growth factor receptor 2 (FGFR2)-mediated reciprocal regulation loop between FGF8 and FGF10 is essential for limb induction. Development 125: 753-765; Eswarakumar V P, E Monsonego-Ornan, M Pines, I Antonopoulou, G M Morriss-Kay and P Lonai. (2002). The IIIc alternative of Fgfr2 is a positive regulator of bone formation. Development 129:3783-3793.), and bone overgrowth (FGFR3) (Deng C, A Wynshaw-Boris, F Zhou, A Kuo and P Leder. (1996). Fibroblast growth factor receptor 3 is a negative regulator of bone growth. Cell 84:911-921.). In humans, genetic studies have linked bone growth and patterning disorders, including Pfeiffer syndrome (FGFR1) (Muenke M, U Schell, A Hehr, N H Robin, H W Losken, A Schinzel, L J Pulleyn, P Rutland, W Reardon and S Malcolm. (1994). A common mutation in the fibroblast growth factor receptor 1 gene in Pfeiffer syndrome. Nature Genet 8:269-274.), Crouzon syndrome (FGFR2) (Reardon W, R M Winter, P Rutland, L J Pulleyn, B M Jones and S Malcolm. (1994). Mutations in the fibroblast growth factor receptor 2 gene cause Crouzon syndrome. Nature Genet 8:98-103.), and achondroplasia (FGFR3) (Rousseau F, J Bonaventure, L Legeai-Mallet, A Pelet, J M Rozet, P Maroteaux, M Le Merrer and A Munnich. (1994). Mutations in the gene encoding fibroblast growth factor receptor-3 in achondroplasia. Nature 371:252-254.) to chromosomal mutations.

FGFR1 expression has been noted in a number of tumors (e.g. see Table 5 of WO 2005/066211).

SUMMARY OF THE INVENTION

In one aspect of the present invention the use of an FGFR1 antibody in the manufacture of a medicament for use in the treatment of cancer is provided, wherein the FGFR1 antibody binds FGFR1 at an epitope that is positioned in the FGFR1 primary amino acid sequence no more than 50 contiguous amino acids away from the C- or N-terminal of the FGFR1 heparin binding domain.

In another aspect of the present invention an FGFR1 antibody is provided for use in a method of treatment of cancer, wherein the FGFR1 antibody binds FGFR1 at an epitope that is positioned in the FGFR1 primary amino acid sequence no more than 50 contiguous amino acids away from the C- or N-terminal of the FGFR1 heparin binding domain.

In a further aspect of the present invention a method of treating a cancer in a subject in need of treatment is provided, the method comprising administering an FGFR1 antibody to the subject, wherein the FGFR1 antibody binds FGFR1 at an epitope that is positioned in the FGFR1 primary amino acid sequence no more than 50 contiguous amino acids away from the C- or N-terminal of the FGFR1 heparin binding domain.

In another aspect of the present invention the use of an FGFR1 antibody in the manufacture of a medicament for use in the treatment of cancer is provided, wherein the antibody binds to FGFR1 and to the peptide SSSEEKETDNTKPNR [SEQ ID NO:2].

In a further aspect of the present invention an FGFR1 antibody is provided for use in a method of treatment of cancer, wherein the FGFR1 antibody binds to FGFR1 and to the peptide SSSEEKETDNTKPNR [SEQ ID NO:2].

In yet a further aspect of the present invention a method of treating a cancer in a subject in need of treatment is provided, the method comprising administering an FGFR1 antibody to the subject, wherein the FGFR1 antibody binds to FGFR1 and to the peptide SSSEEKETDNTKPNR [SEQ ID NO:2].

In another aspect of the present invention an in vitro method of causing cell death in cancerous cells is provided, the method comprising contacting cancerous cells in vitro with an FGFR1 antibody that binds FGFR1 at an epitope that is positioned in the FGFR1 primary amino acid sequence no more than 50 contiguous amino acids away from the C- or N-terminal of the FGFR1 heparin binding domain.

In a further aspect of the present invention an in vitro method of causing cell death in cancerous cells is provided, the method comprising contacting cancerous cells in vitro with an FGFR1 antibody that binds to FGFR1 and to the peptide SSSEEKETDNTKPNR [SEQ ID NO:2].

DESCRIPTION OF PREFERRED EMBODIMENTS

The present invention concerns the use of a particular class of FGFR1 antibody in methods of causing cell death. In particular, methods and uses involve causing cell death in cancerous cells in vitro or in vivo and therefore include applications in the treatment of cancer.

The inventors have found that the polyclonal antibody IMB-R1 isolated against the peptide antigen SSSEEKETDNTKPNR [SEQ ID NO:2] is capable of:
  (i) specific binding to FGFR1 (in particular to isoforms FGFR1b and FGFR1c), over FGFR2 and FGFR3 and other FGFRs,
  (ii) inhibition of cell growth in sarcoma cells and carcinoma cells,
  (iii) driving apoptosis of sarcoma cells and induction of changes in the expression of tumor repressor and apoptotic proteins,
  (iv) inhibition of FGF2 stimulated cell growth in sarcoma cells, and
  (v) inhibition of phosphorylation of FGFR1 in response to stimulation of FGF2.

FGFR1 antibodies of the present invention preferably bind to FGFR1 with high affinity and exhibit specificity for FGFR1 over one or more of FGFR2, FGFR3 and/or FGFR4.

The binding affinity ($K_d$) of FGFR1 antibodies of the present invention for FGFR1 is preferably in the μM or nM range. Preferably, FGFR1 antibodies of the present invention have a $K_d$ of less than 500 μM, more preferably one of less than 400 μM, less than 300 μM, less than 200 μM, less than 100 μM, less than 50 μM, less than 40 μM, less than 30 μM, less than 20 μm, less than 10 μM, less than 5 μM, less than 1 μM, less than 900 nM, less than 800 nM, less than 700 nM, less than 600 nM, less than 500 nM, less than 400 nM, less than 300 nM, less than 200 nM, less than 100 nM, less than 90 nM, less than 80 nM, less than 70 nM, less than 60 nM, less than 50 nM, less than 40 nM, less than 30 nM, less than 20 nM, less than 10 nM, less than 5 nM, or less than 1 nM. The $K_d$ may be between 10 nM and 50 μM, or between 10 nM and 30 μM, or between 100 nM and 20 μM or between 100 nM and 10 μM.

FGFR1 antibodies of the present invention are capable of binding FGFR1 at an epitope that is positioned in the FGFR1 primary amino acid sequence no more than 50 contiguous amino acids away from the C- or N-terminal of the FGFR1 heparin binding domain. In some embodiments the epitope is positioned no more than one of 40, 35, 30, 25, 20, 15, 10 or 5 amino acids away from the C- or N-terminal of the FGFR1 heparin binding domain.

The separation of the epitope and heparin binding domain is determined as the minimum number of amino acids in the contiguous primary amino acid sequence of the FGFR1 between either (i) the C-terminal end of the primary amino acid sequence of the epitope as it appears in the FGFR1 primary amino acid sequence and the N-terminal end of the primary amino acid sequence of the heparin binding domain as it appears in the FGFR1 primary amino acid sequence, or (ii) the C-terminal end of the primary amino acid sequence of the heparin binding domain as it appears in the FGFR1 primary amino acid sequence and the N-terminal end of the primary amino acid sequence of the epitope as it appears in the FGFR1 primary amino acid sequence, wherein the N- and C-terminal amino acids are not included in the number of amino acids separating the respective sequence components.

As such, the separation between the epitope sequence and heparin binding domain sequence may be selected from any one of 50 amino acids or less, 45 amino acids or less, 40 amino acids or less, 35 amino acids or less, 30 amino acids or less, 25 amino acids or less, 20 amino acids or less, 15 amino acids or less, 10 amino acids or less, or 5 amino acids or less. The separation between the epitope sequence and heparin binding domain sequence may be selected from any one of 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids.

In some embodiments FGFR1 antibodies of the present invention preferably bind to an epitope having the amino acid sequence SSSEEKETDNTKPNR [SEQ ID NO:2] and/or to an epitope having an amino acid sequence comprising SSSEEKETDNTKPNR [SEQ ID NO:2] and/or to an epitope having an amino acid sequence comprising part of the amino acid sequence of SSSEEKETDNTKPNR [SEQ ID NO:2], for example an amino acid sequence comprising one of at least 8, 9, 10, 11, 12, 13, or 14 amino acids of SEQ ID NO:2 in the same contiguous sequence.

In some embodiments FGFR1 antibodies of the present invention preferably bind to a peptide or polypeptide comprising an amino acid sequence of less than 20 amino acids in length having at least 66% sequence identity to the amino acid sequence of SSSEEKETDNTKPNR [SEQ ID NO:2]. The length of said amino acid sequence may be one of less than 19 amino acids, less than 18 amino acids, less than 17 amino acids, less than 16 amino acids or less than 15 amino acids. The percentage sequence identity may be selected from one of at least 70%, at least 75%, at least 80%, at least 85%, at least 90%, at least 91% at least 92% at least 93% at least 94% at least 95% at least 96% at least 97% at least 98% at least 99% or 100%.

The heparin binding domain of the FGFR may have the amino acid sequence KMEKKLHAVPAAKTVKFK [SEQ ID NO:3] or an amino acid sequence having at least 66% sequence identity to the amino acid sequence of SEQ ID NO:3. The percentage sequence identity may be selected from one of at least 70%, at least 75%, at least 80%, at least 85%, at least 90%, at least 91% at least 92% at least 93% at least 94% at least 95% at least 96% at least 97% at least 98% at least 99% or 100%.

In preferred embodiments FGFR1 antibodies of the present invention are capable of binding to the extracellular domain of FGFR1, e.g. when expressed at the cell surface.

In some embodiments FGFR1 antibodies of the present invention are antagonist antibodies. In some preferred embodiments FGFR1 antibodies of the present invention are capable of inhibiting binding of a Fibroblast Growth Factor (e.g. FGF2, preferably mammalian or human FGF2) to FGFR1. In some embodiments FGFR1 antibodies of the present invention are capable of inhibiting/antagonizing FGFR1 signalling, optionally leading to inhibition of cell growth and/or induction of apoptosis in tumor cells that express FGFR1, most preferably on their cell surface.

In some embodiments FGFR1 antibodies of the present invention may be monoclonal or polyclonal and may be obtained by a method of generating antibodies against a peptide comprising the amino acid sequence SSSEEKETDNTKPNR [SEQ ID NO:2].

In some embodiments FGFR1 antibodies of the present invention may be monoclonal or polyclonal and may be obtained by a method of generating antibodies against a polypeptide or peptide having an amino acid sequence comprising all or part of the amino acid sequence of SSSEEKETDNTKPNR [SEQ ID NO:2], for example an amino acid sequence comprising one of at least 8, 9, 10, 11, 12, 13, 14, or 15 amino acids of SEQ ID NO:2 in the same contiguous sequence.

In some embodiments FGFR1 antibodies of the present invention may be monoclonal or polyclonal and may be obtained by a method of generating antibodies against a polypeptide or peptide having an amino acid sequence comprising an amino acid sequence of less than 20 amino acids in length having at least 66% sequence identity to the amino acid sequence of SSSEEKETDNTKPNR [SEQ ID NO:2]. The length of said amino acid sequence may be one of less than 19 amino acids, less than 18 amino acids, less than 17 amino acids, less than 16 amino acids or less than 15 amino acids. The percentage sequence identity may be selected from one of at least 70%, at least 75%, at least 80%, at least 85%, at least 90%, at least 91% at least 92% at least 93% at least 94% at least 95% at least 96% at least 97% at least 98% at least 99% or 100%.

Monoclonal antibodies (mAbs) are a homogenous population of antibodies specifically targeting a single epitope on an antigen. Suitable monoclonal antibodies can be prepared using methods well known in the art (e.g. see Köhler, G.; Milstein, C. (1975). "Continuous cultures of fused cells secreting antibody of predefined specificity". Nature 256 (5517): 495; Siegel D L (2002). "Recombinant monoclonal antibody technology". Schmitz U, Versmold A, Kaufmann P, Frank H G (2000); "Phage display: a molecular tool for the generation of antibodies—a review". Placenta. 21 Suppl A: S106-12. Helen E. Chadd and Steven M. Chamow; "Therapeutic antibody expression technology," Current Opinion in Biotechnology 12, no. 2 (Apr. 1, 2001): 188-194; McCafferty, J.; Griffiths, A.; Winter, G.; Chiswell, D. (1990). "Phage antibodies: filamentous phage displaying antibody variable domains". Nature 348 (6301): 552-554; "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger et al (1988, 8th International Biotechnology Symposium Part 2, 792-799)).

Polyclonal antibodies are useful in the methods of the invention. Monospecific polyclonal antibodies are preferred. Suitable polyclonal antibodies can be prepared using methods well known in the art, e.g. as described herein for the generation of IMB-R1.

In view of today's techniques in relation to monoclonal antibody technology, antibodies can be prepared to most antigens.

The antigen-binding portion of an FGFR1 antibody of the present invention may be a part of an antibody (for example a Fab fragment) or a synthetic antibody fragment (for example a single chain Fv fragment [ScFv]). Suitable monoclonal antibodies to selected antigens may be prepared by known techniques, for example those disclosed in "Monoclonal Antibodies: A manual of techniques", H Zola (CRC Press, 1988) and in "Monoclonal Hybridoma Antibodies: Techniques and Applications", J G R Hurrell (CRC Press, 1982). Chimaeric antibodies are discussed by Neuberger et al (1988, 8th International Biotechnology Symposium Part 2, 792-799).

Fragments of antibodies, such as Fab and $Fab_2$ fragments, may also be used as can genetically engineered antibodies and antibody fragments. The variable heavy ($V_H$) and variable light ($V_L$) domains of the antibody are involved in antigen recognition, a fact first recognised by early protease digestion experiments. Further confirmation was found by "humanisation" of rodent antibodies. Variable domains of rodent origin may be fused to constant domains of human origin such that the resultant antibody retains the antigenic specificity of the rodent parented antibody (Morrison et al (1984) Proc. Natl. Acad. Sd. USA 81, 6851-6855).

That antigenic specificity is conferred by variable domains and is independent of the constant domains is known from experiments involving the bacterial expression of antibody fragments, all containing one or more variable domains. These molecules include Fab-like molecules (Better et al (1988) Science 240, 1041); Fv molecules (Skerra et al (1988) Science 240, 1038); single-chain Fv (ScFv) molecules where the $V_H$ and $V_L$ partner domains are linked via a flexible oligopeptide (Bird et al (1988) Science 242, 423; Huston et al (1988) Proc. Natl. Acad. Sd. USA 85, 5879) and single domain antibodies (dAbs) comprising isolated V domains (Ward et al (1989) Nature 341, 544). A general review of the techniques involved in the synthesis of antibody fragments which retain their specific binding sites is to be found in Winter & Milstein (1991) Nature 349, 293-299.

By "ScFv molecules" we mean molecules wherein the $V_H$ and $V_L$ partner domains are covalently linked, e.g. directly, by a peptide or by a flexible oligopeptide.

Fab, Fv, ScFv and dAb antibody fragments can all be expressed in and secreted from *E. coli*, thus allowing the facile production of large amounts of the said fragments.

Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site. Synthetic FGFR1 antibodies of the present invention may also be made using phage display technology as is well known in the art (e.g. see "Phage display: a molecular tool for the generation of antibodies—a review". Placenta. 21 Suppl A: S106-12. Helen E. Chadd and Steven M. Chamow; "Phage antibodies: filamentous phage displaying antibody variable domains". Nature 348 (6301): 552-554).

In some preferred embodiments the FGFR1 antibody is detectably labelled or, at least, capable of detection. For example, the antibody may be labelled with a radioactive atom or a coloured molecule or a fluorescent molecule or a molecule which can be readily detected in any other way. Suitable detectable molecules include fluorescent proteins, luciferase, enzyme substrates, and radiolabels. The antibody may be directly labelled with a detectable label or it may be indirectly labelled. For example, the antibody may be unlabelled and can be detected by another antibody which is itself labelled. Alternatively, the second antibody may have bound to it biotin and binding of labelled streptavidin to the biotin is used to indirectly label the first antibody.

In certain embodiments, the FGFR1 antibody is IMB-R1. IMB-R1 is a polyclonal antibody isolated by Ling et al (Journal of Cellular Physiology 209:811-825 (2006)) and was subsequently used by Woie N g et al (Stem Cells and Development 16:305-318 (2007)). As reported, IMB-R1 was isolated by the following method: The peptide SSSEEKETDNTKPNR located between the 1$^{st}$ and 2nd Ig loop of FGFR1 was used for the production of polyclonal antibodies in two rabbits (BioGenes). The choice of the peptidic sequence was based on identity between the human, mouse, and rat protein and the highest hydrophilicity according to the Kyte-Doolittle hydropathy plot. This sequence was unique to FGFR1 and not found in FGFR2, 3 or 4. The peptide was conjugated to LPH (Hemocyanine from *Limulus polyphemus*) and immunization was performed with injections at 0, 7, 14, 28, and 35 days. Sera from the first and the second bleeding were pooled and used for the subsequent experiments. The titer of the pooled antibodies was determined to be >1:200,000 by standard enzyme-linked immunosorbent assay (ELISA). The specificity of the antibody was verified by producing the extracellular portion of FGFR1 in *Escherichia coli*, lysing the pelleted bacteria directly in Laemmli buffer, and Western blotting with the FGFR1 antibody (1:10, 000). Furthermore, MG-63, MC3T3-E1, and rat calvarial cell lysates, which are known to express FGFR1, were also examined by Western blot for the detection of endogenous FGFR1 under reducing conditions.

In other embodiments the FGFR1 antibody is a monoclonal antibody with the same binding properties as IMB-R1. The monoclonal antibody may be a monoclonal antibody raised against SSSEEKETDNTKPNR. The antibody may be an IgG. The monoclonal antibody may have higher affinity for FGFR1c than FGFR1b. The antibody may have higher binding affinity for FGFR1 than FGFR 2 or FGFR3. In some cases the antibody does not bind FGFR2 and/or FGFR3. The monoclonal antibody may be obtained by any protocol known in the art. It may be obtained by the protocol described in Example 16 and/or as set out in FIG. 25.

FGFR1 is a member of the fibroblast growth factor receptor (FGFR) family. Member of the family of FGFRs have highly conserved amino acid sequences. FGFR family members differ from one another in their ligand affinities and tissue distribution.

FGFR isoform a (IIIa) is a secreted protein, whereas isoforms b (IIIb) and c (IIIc) are found in the cell membrane and have an extracellular region, composed of three immunoglobulin-like domains, a single hydrophobic membrane-spanning segment and a cytoplasmic tyrosine kinase domain. The extracellular portion of the protein interacts with fibroblast growth factors, setting in motion a cascade of downstream signals, ultimately influencing mitogenesis and differentiation (Johnson et al Molecular and Cellular Biology September 1991 p4267-4634).

FGFR1 has been found to be expressed in a wide range of human cancers, including tumors of the adrenal glad, adrenal medulla, anus, appendix, bladder, bone, bone marrow, brain, breast, cecum, cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph node (including abdominal lymph node, axillary lymph node, cervical lymph node, inguinal lymph node, mediastinal lymph node, pelvic lymph node, periaortic lymph node), lymphoblast, maxilla, mediastinum, mesentery, myometrium, nasopharynx, oral cavity, ovary, pancreas, parotid gland, peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells (e.g. see Table 5 of WO 2005/066211).

The amino acid sequence for human FGFR1 is shown in FIG. 14 (SEQ ID NO:1). The amino acid sequence for human FGFR1 isoform c is also shown in FIG. 14 (SEQ ID NO:4) in which the amino acid sequence of the third immunoglobulin domain is underlined. The projected amino acid sequence for human FGFR1 isoform b is also shown in FIG. 14 (SEQ ID NO:6) in which the third immunoglobulin domain (SEQ ID NO:5) is underlined.

SEQ ID NO:4 is indicated to have an approximately 99% sequence identity with SEQ ID NO:1, as determined by BLAST. SEQ ID NO:6 is indicated to have an approximately 97% sequence identity with SEQ ID NO:1, as determined by a BLAST alignment and comparison.

In this specification reference to FGFR1 is to Fibroblast Growth Factor Receptor 1. Preferably, the FGFR1 is mammalian (e.g. rabbit, guinea pig, rat, mouse or other rodent (including cells from any animal in the order Rodentia), cat, dog, pig, sheep, goat, cattle, horse, non-human primate or other non-human mammal) and most preferably is human. Reference to FGFR1 includes FGFR1 molecules having at least 60% sequence identity to one of SEQ ID NOs:1, 4 or 6. The percentage sequence identity may be one of 65%, 70%, 75%, 80%, 85%, 90%, 91%, 92%, 93%, 94%, 95%, 96%, 97%, 98%, 99% or 100%.

Aspects of the present invention concern the effect of FGFR1 antibodies of the present invention on cancer and cancerous cells.

The subject to be treated may be any animal or human. The subject is preferably mammalian, more preferably human. The subject may be a non-human mammal, but is more preferably human. The subject may be male or female. The subject may be a patient. Therapeutic uses may be in human or animals (veterinary use).

A cancer may be any unwanted cell proliferation (or any disease manifesting itself by unwanted cell proliferation), neoplasm or tumour or increased risk of or predisposition to the unwanted cell proliferation, neoplasm or tumour. The cancer may be benign or malignant and may be primary or secondary (metastatic). A neoplasm or tumour may be any abnormal growth or proliferation of cells and may be located in any tissue. Examples of tissues include the adrenal glad, adrenal medulla, anus, appendix, bladder, blood, bone, bone marrow, brain, breast, cecum, central nervous system (including or excluding the brain) cerebellum, cervix, colon, duodenum, endometrium, epithelial cells (e.g. renal epithelia), gallbladder, oesophagus, glial cells, heart, ileum, jejunum, kidney, lacrimal glad, larynx, liver, lung, lymph, lymph node (including abdominal lymph node, axillary lymph node, cervical lymph node, inguinal lymph node, mediastinal lymph node, pelvic lymph node, periaortic lymph node), lymphoblast, maxilla, mediastinum, mesentery, myometrium, nasopharynx, oral cavity, ovary, pancreas, parotid gland, peripheral nervous system peritoneum, pleura, prostate, salivary gland, sigmoid colon, skin, small intestine, soft tissues, spleen, stomach, testis, thymus, thyroid gland, tongue, tonsil, trachea, uterus, vulva, white blood cells Cancers may be of a particular type. Examples of types of cancer include astrocytoma, carcinoma, glioma, lymphoma, medulloblastoma, melanoma, myeloma, meningioma, neuroblastoma, sarcoma. In some embodiments the cancer is a carcinoma or a sarcoma. In some embodiments the cancer is an osteosarcoma or a carcinoma of the breast.

The cancer may be selected from breast cancer such as breast carcinoma, lung cancer such as lung adenocarcinoma or lung squamous cell carcinoma, Hodgkin's lymphoma, non-Hodgkin's lymphoma, esophageal cancer such as squamous cell esophageal carcinoma or esophageal adenocarcinoma, bladder cancer such as urothelial carcinoma, ovarian cancer such as ovary carcinoma, skin cancer such as melanoma, prostate cancer such as prostate carcinoma, cervical cancer such as cervical carcinoma, testis cancer such as seminoma or embryonal carcinoma, colon cancer such as colon adenocarcinoma, uterine cancer such as uterus endometrioid adenocarcinoma, thyroid cancer such as thyroid carcinoma, kidney cancer such as kidney carcinoma, liver cancer, liposarcoma, fibrosarcoma, pancreatic cancer such as pancreas carcinoma, brain cancer such as gliobastoma or astrocytoma or stomach cancer such as stomach adenocarcinoma.

In some embodiments, the disorder to be treated is selected from breast carcinoma, lung adenocarcinoma, lung squamous cell carcinoma, Hodgkin's lymphoma, non-Hodgkin's lymphoma, squamous cell esophageal carcinoma, esophageal adenocarcinoma, urothelial carcinoma, melanoma.

In others, the disorder to be treated is pancreas carcinoma, glioblastoma, astrocytoma or stomach adenocarcinoma.

Cancerous cells may be cells obtained from a cancer in a subject, e.g. a human or mammalian patient, or may be from a cancer cell line. Cancerous cells preferably express FGFR1 on the cell surface. Cancerous cells may be obtained from or derived from any of the tissues described above. The cancerous cells may have differential expression or activity of FGFR1 as compared to non-cancerous cells. For example, FGFR1 activity or expression may be upregulated in the cancerous cells as compared to normal, or non-cancerous, cells.

The FGFR1 antibodies for use in the present invention may be formulated as medicaments or pharmaceutical compositions for clinical use and may comprise a pharmaceutically acceptable carrier, diluent or adjuvant. The medicament or composition may be formulated for topical, parenteral, systemic, intravenous, intra-arterial, intramuscular, intrathecal, intraocular, intratumoral, subcutaneous, oral or transdermal routes of administration which may include injection. Injectable formulations may comprise the selected compound in a sterile or isotonic medium. Injection may be to cancer tissue.

Administration is preferably in a "therapeutically effective amount", this being sufficient to show benefit to the individual. The actual amount administered, and rate and time-course of administration, will depend on the nature and severity of the disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins. A composition may be administered alone or in combination with other treatments, either simultaneously or sequentially dependent upon the condition to be treated.

FGFR1 antibodies of the present invention may cause cell death in cancerous cells that express FGFR1, e.g. on the cell surface. As such, the FGFR1 antibodies may kill cancerous cells that are contacted with the FGFR1 antibody.

The nature of the cell death may involve programmed cell death (apoptosis). Apoptotic cell death, as opposed to necrosis (cyotoxic cell death), involves a series of biochemical events that lead to death of the cell. Cells undergoing apoptosis often undergo blebbing, loss of cell membrane asymmetry, cell shrinkage, nuclear fragmentation, chromosome condensation and fragmentation. The presence of apoptotic cell death can also be determined by assaying for markers of apoptosis such as Annexin V and Caspase 3. Methods according to the present invention may be performed in vitro or in vivo. The term "in vitro" is intended to encompass experiments with cells in culture whereas the term "in vivo" is intended to encompass experiments with intact multi-cellular organisms.

Percentage (%) sequence identity is defined as the percentage of amino acid residues in a candidate sequence that are identical with residues in the given listed sequence (referred to by the SEQ ID NO.) after aligning the sequences and introducing gaps if necessary, to achieve the maximum sequence identity, and not considering any conservative substitutions as part of the sequence identity. Sequence identity is preferably calculated over the entire length of the respective sequences.

Alignment for purposes of determining percent amino acid sequence identity can be achieved in various ways known to a person of skill in the art, for instance, using publicly available computer software such as BLAST or ClustalW 1.82. T-coffee or Megalign (DNASTAR) software. When using such software, the default parameters, e.g. for gap penalty and extension penalty, are preferably used. The default parameters of ClustalW 1.82 are: Protein Gap Open Penalty=10.0, Protein Gap Extension Penalty=0.2, Protein matrix=Gonnet, Protein/DNA ENDGAP=−1, Protein/DNA GAPDIST=4.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which:

FIG. 14.
SEQ ID NO:1—Amino acid sequence for human FGFR1 (GenBank Accession No. P11362.3 (GI:120046)).
SEQ ID NO:2—The 15 amino acid peptide (SS-SEEKETDNTKPNR) used to generate antibody IMB-R1 (underlined in SEQ ID NO:1).
SEQ ID NO:3—The 18 amino acid heparin binding domain of FGFR1 (KMEKKLHAVPAAKTVKFK) (also underlined in SEQ ID NO:1). SEQ ID NO:3 is reported in Kan et al Science Vol. 259 p 1918 26 Mar. 1993.
SEQ ID NO:4—Amino acid sequence for FGFR1 isoform c (GenBank Accession no: NP_056934.2 (GI: 13186251)) having about 99% sequence identity to SEQ ID NO:1, differing in sequence by two amino acids. The amino acid sequence of the third immunoglobulin domain is underlined.
SEQ ID NO:5—Amino acid sequence for the third immunoglobulin domain of FGFR1 isoform b (GenBank Accession no: AAB19502.1 (GI:233769)). This splice variant differs from the amino acid sequence of FGFR1 isoform c (SEQ ID NO:4) in the third immunoglobulin domain.
SEQ ID NO:6—Proposed amino acid sequence for FGFR isoform b based on replacement of the third immunoglobulin domain sequence from SEQ ID NO:4 with the sequence of SEQ ID NO:5 (underlined in SEQ ID NO:6).
FIG. 15. Alignment of amino acid sequence of the third immunoglobulin domain of FGFR1 isoform b (SEQ ID NO:5) with the third immunoglobulin domain of FGFR1 isoform c (SEQ ID NO:7) (Johnson et al. Molecular and Cellular biology September 1991 p 4267-4632).

FIG. 22. Tissue array of IMB-R1 in different cancer types.

DETAILED DESCRIPTION OF THE INVENTION

Figure 1:
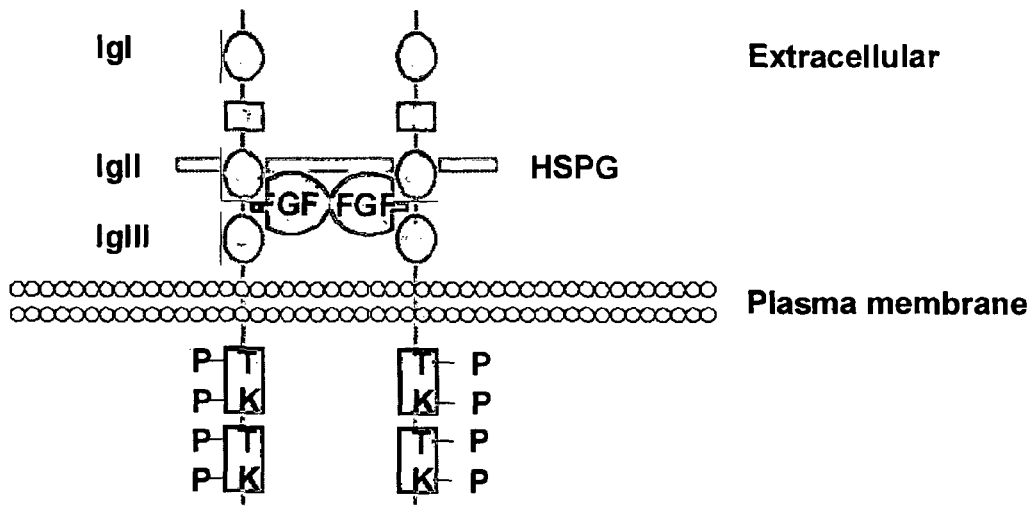
FIG. 1. Diagram of FGFR1 receptor at the cell membrane.
Figure 2A:
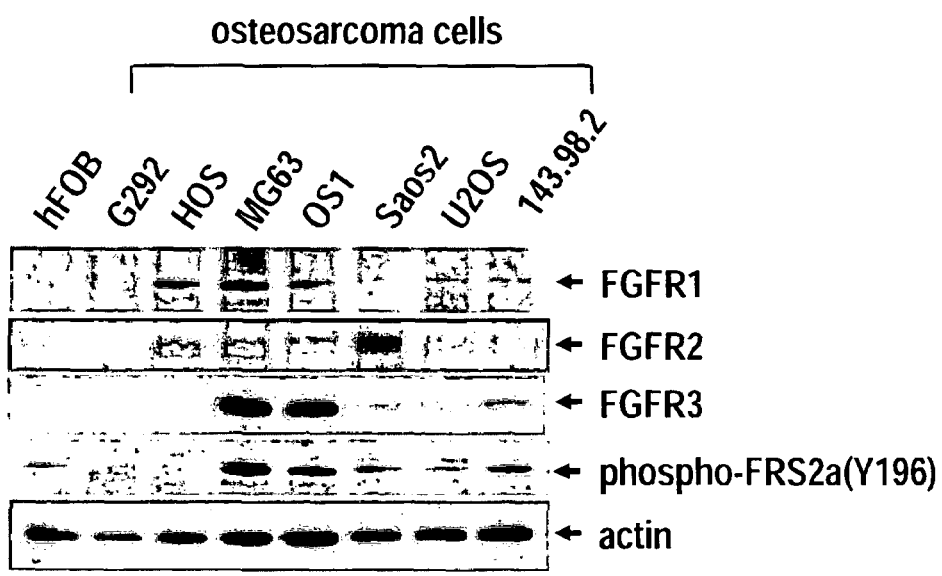
FIG. 2. (A) Western blot indicating protein expression levels of FGFR1, FGFR2, FGFR3 and the level of phosphorylated FRS2a in normal human osteoblasts (hFOB), osteosarcoma cell lines (G292, HOS, MG63, Saos2, U2OS, 143.98.2) and primary human osteosarcoma cells (OS1). (B) and (C) graphs showing quantified intensity of protein bands on Western blots. (D) protein levels of FGFRs examined by western blot in normal human osteoblasts (hFOB), osteosarcoma cells (HOS and MG63) and primary human osteosarcoma cells (OS1). (F) protein expression levels of FGFRs examined by western blot analysis in normal human mammary gland epithelial cell (MCF10A) and three breast cancer cell lines (MCF7, T47D and MDA-MB468) (E), (G) The intensity of protein bands on blots was quantified by densitometric scanning (Epson V500, Epson) and analysed by Quantity One software (Bio-Rad).
Figure 2B:
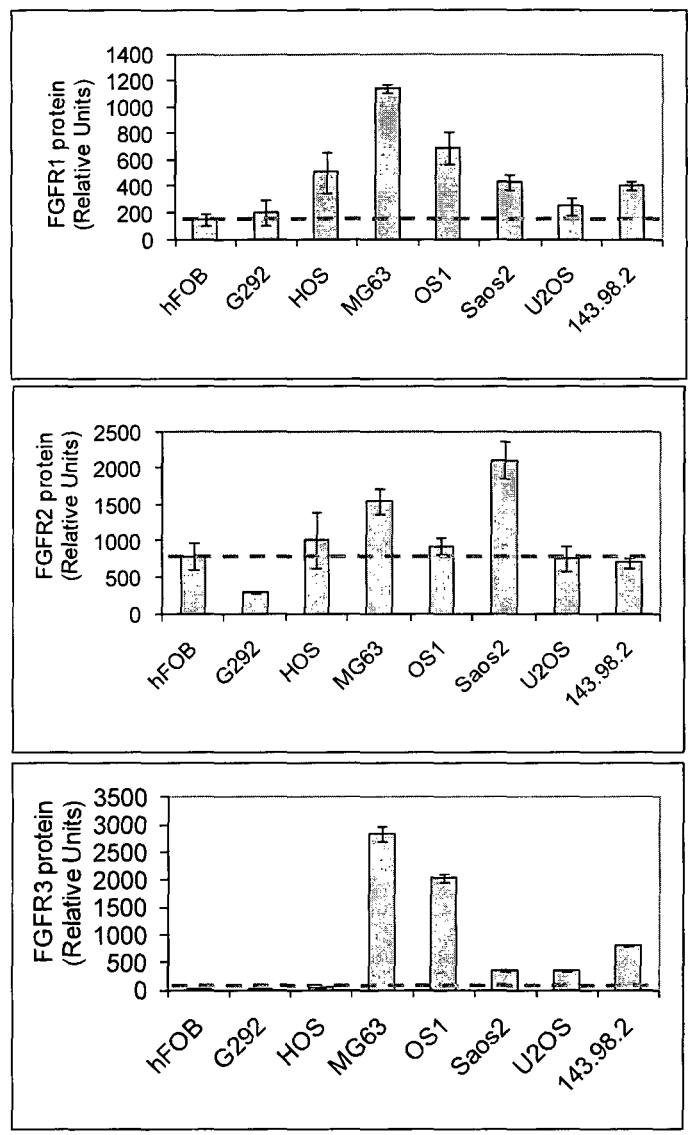
Figure 2C:
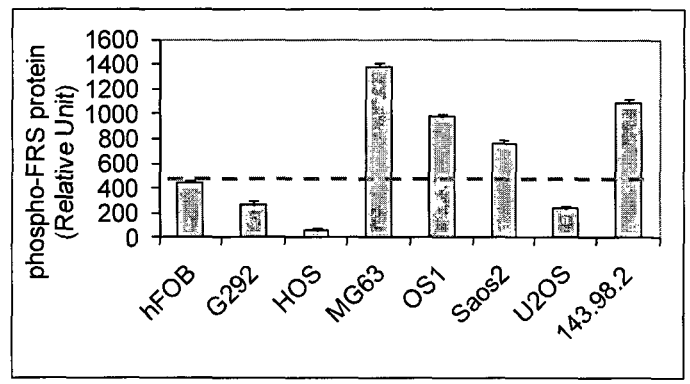
Figure 2D:
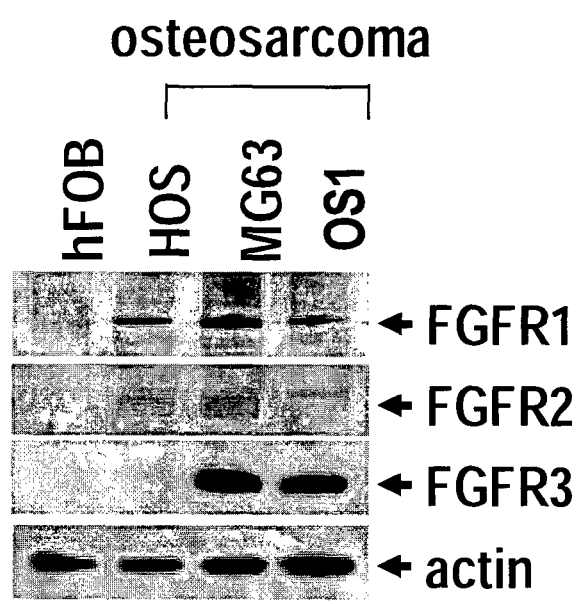
Figure 2F:
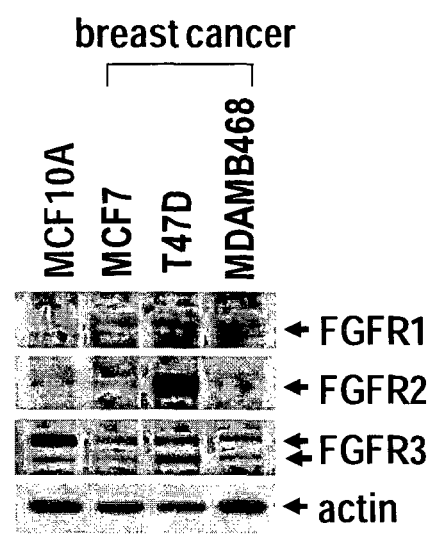
Figure 2G:
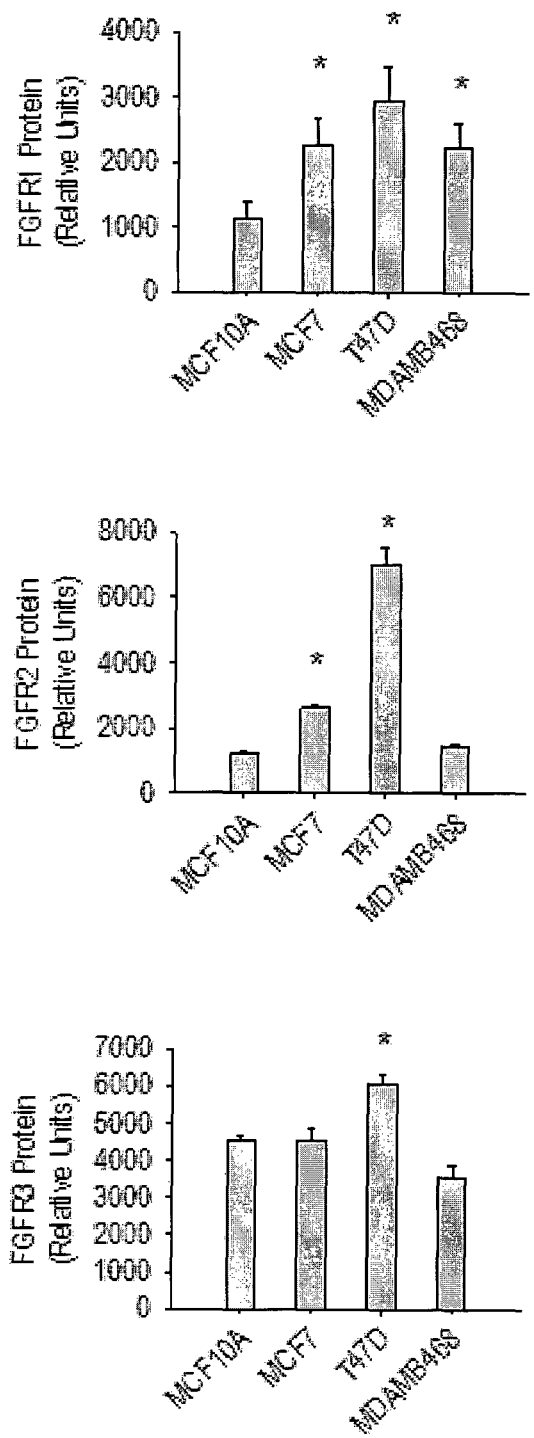

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

As described in the following Examples, the inventors have found that polyclonal antibody IMB-R1 binds to cell surface FGFR1 resulting in induction of cell death in cancerous cells. IMB-R1 specifically targets a peptide sequence SSSEEKETDNTKPNR [SEQ ID NO:2] present on the extracellular portion of FGFR1 that is not present on other cell surface receptors with the target sequence being less than 30 amino acids upstream of the heparin-binding domain (HBD) on FGFR1 which is known to be important for interaction of FGF with FGFR1. It is believed that IMB-R1 is able to mask the HBD that facilitates FGF binding to FGFR1.

IMB-R1 is shown to have a high specificity for FGFR1 and high potency to block FGF signalling pathway in cancerous cells.

Sarcoma and carcinoma cells treated with IMB-R1 were unable to divide and underwent programmed cell death due to an elevated p53/p21 DNA damage response pathway. IMB-R1 binds to the FGFR1 cell surface receptor in an antagonistic manner (blocking FGF signalling and inhibiting FGF2 stimulated cell growth) and induces apoptotic cell death in sarcoma cells.

In comparison, a commercially available neutralizing FGFR1 antibody from R&D systems was found not to be able to inhibit endogenous FGFR1 signalling, although it was able to inhibit FGFR1 signalling induced by high doses of exogenous FGF2, suggesting a low potency. Furthermore, this commercial antibody only neutralizes the bioactivity of a specific isoform of FGFR1 (IIIb isoform), but not that of the IIIc isoform of FGFR1. IMB-R1 targets the various isoforms of FGFR1 binding to both 'b' and 'c' isoforms.

EXAMPLES

Example 1

Preparation of IMB-R1

IMB-R1 is a polyclonal antibody isolated by Ling et al (Journal of Cellular Physiology 209:811-825 (2006)) and was subsequently used by Woie N g et al (Stem Cells and Development 16:305-318 (2007)).

IMB-R1 was isolated by the following method: The peptide SSSEEKETDNTKPNR located between the $1^{st}$ and 2nd Ig loop of FGFR1 was used for the production of polyclonal antibodies in two rabbits (BioGenes). The choice of the peptidic sequence was based on identity between the human, mouse, and rat protein and the highest hydrophilicity according to the Kyte-Doolittle hydropathy plot. This sequence was unique to FGFR1 and not found in FGFR2, 3 or 4. The peptide was conjugated to LPH (Hemocyanine from *Limulus polyphemus*) and immunization was performed with injections at 0, 7, 14, 28, and 35 days. Sera from the first and the second bleeding were pooled and used for the subsequent experiments. The titer of the pooled antibodies was determined to be >1:200,000 by standard enzyme-linked immunosorbent assay (ELISA). The specificity of the antibody was verified by producing the extracellular portion of FGFR1 in *Escherichia coli*, lysing the pelleted bacteria directly in Laemmli buffer, and Western blotting with the FGFR1 antibody (1:10,000). Furthermore, MG-63, MC3T3-E1, and rat calvarial cell lysates, which are known to express FGFR1, were also examined by Western blot for the detection of endogenous FGFR1 under reducing conditions.

Example 2

Uprequlation of FGFRs in Osteosarcoma

Protein expression levels of FGFR1, FGFR2, FGFR3 and the level of phosphorylated FRS2a were examined by Western blot analysis in normal human osteoblasts (hFOB), osteosarcoma cell lines (G292, HOS, MG63, Saos2, U2OS, 143.98.2) and primary human osteosarcoma cells (OS1). The intensity of protein bands on the Western blot was quantified by densitometric scanning (Epson V500, Epson) and analyzed by Quantity One software (Bio-Rad).
Results
FGFRs were up-regulated in most osteosarcoma cells tested (except G292), compared with hFOB, the noncancerous human osteoblasts and in cancerous as compared to normal breast tissues (MCF10A). FRS2a is phosphorylated on tyrosine 196 (Y196) by activated FGFRs. Most (4 out of 6) osteosarcoma cells that expressed more FGFRs also showed increased level of phosphorylated FRS2a, especially in MG63 and OS1 where FGFR1 was most upregulated, phosphorylated FRS2a was also significantly induced, suggesting in those cells the overexpressed FGFR1 correlated with enhanced FGFR signalling (FIG. 2). FGFR2 and FGFR3 were also up-regulated in some of the cancer cells, but not as frequently as FGFR1.

Figure 23:
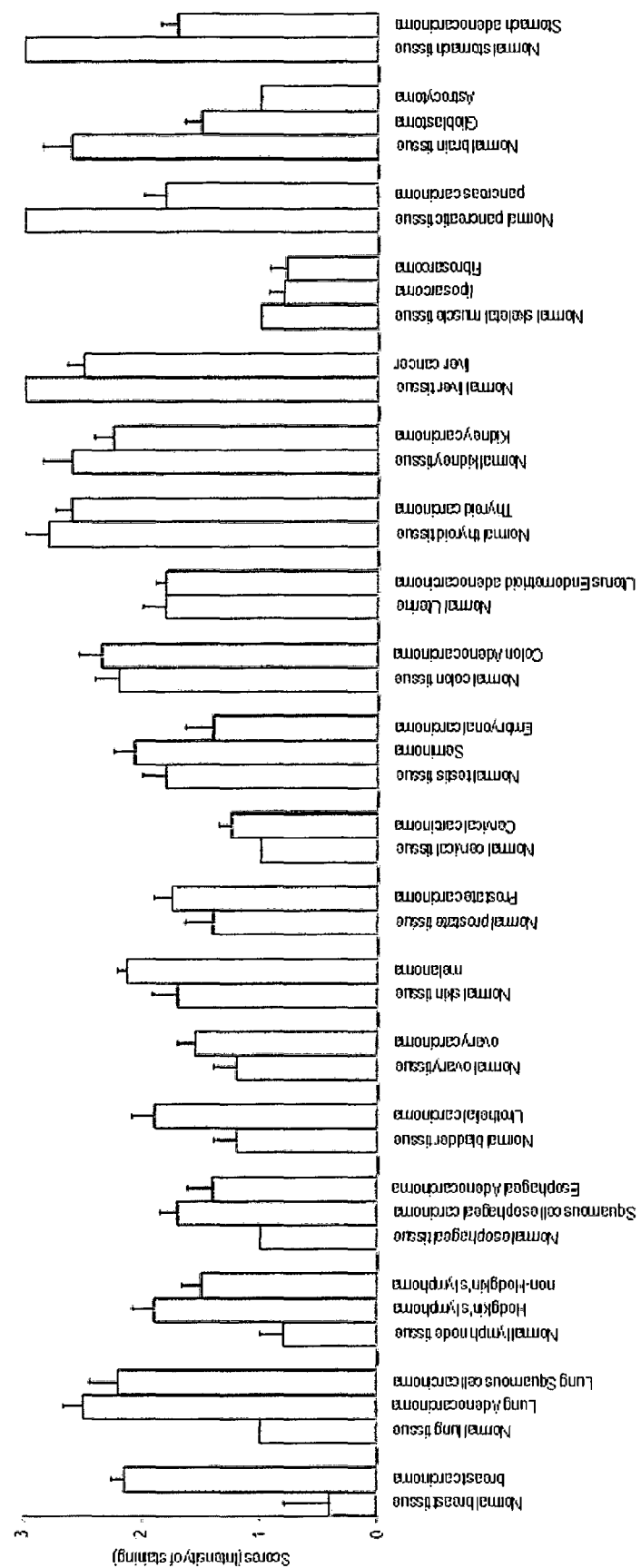
FIG. 23. Graph showing intensity of staining of IMB-R1 in tissue array shown in FIG. 22.

To determine the distribution of IMB-R1 in different cancers, immunohistochemistry (IHC) staining was performed in different human cancer tissues as well as the corresponding normal tissues using IMB-R1. The tissue microarray used for this study is human high-density multiple organ cancer tissue array (US biomax, Inc). This array contains 20 most common types of cancer with about 20 cases/type and 5 cases/type of normal controls. The array is in single core per case format. The tissue samples were formalin fixed, paraffin embedded. Tissue array sections were mounted on the positive charged SuperFrost Plus glass slide. The tissue microarray sections were cut at 5 micron in thickness. Individual cores were 0.6 mm in diameter, spaced 0.25 mm. The staining procedure is the standard IHC protocol. The DAB substrate-chromogen yields a dark brown reaction end-product at the site of the target antigen. Hematoxylin was used for counterstaining cell nuclei which yields blue color staining. Two slides were scanned. 20× object images were provided (FIG. 22). The total positive cell numbers and intensity of the antibody staining were computed and measured by ImageScope from Aperio Scanning System and plotted. The intensity of staining was scored as negative (0), weak (1+), moderate (2+), or strong (3+). The total scores of each cancer type were compared with the corresponding normal tissue as shown in FIG. 23.

Results: As shown in FIG. 22 all of the positive staining (weak to strong positive, 1+-3+) of IMB-R1 antibody were located in cytoplasm and cytoplasm/nucleus in tumor cells of human cancer in varied stages, and staining of cytoplasm and cytoplasm/nucleus in normal tissue. As shown in FIG. 23 IMB-R1 staining was significantly stronger in breast cancer, lung cancer, lymphoma, esophageal cancer, bladder cancer, ovary cancer and melanoma than the normal tissues, suggesting FGFR1 expression was increased in those tumors. Whereas, IMB-R1 staining was significantly weaker in pancreas, stomach and brain tumors, suggesting that FGFR1 level was reduced in those cancers. Interestingly, the amplification of FGFR1 gene has been reported previously in breast, ovarian, lung, bladder and esophageal cancers (Gennaro Daniele, Curr Oncol Rep, 2012. FGF receptor inhibitors: Role in Cancer therapy), which is consistent with our findings that FGFR1 expression was increased in these tumors. More importantly, the fact that these tumors have stronger staining by IMB-R1 than their corresponding normal tissues demonstrated that IMB-R1 was able to target/attack the tumor cells in these tissues or organs at the significantly higher chance than the adjacent normal cells.

Example 3

Predominance of FGFR1 Expression in MG63 Cells

Figure 3A:
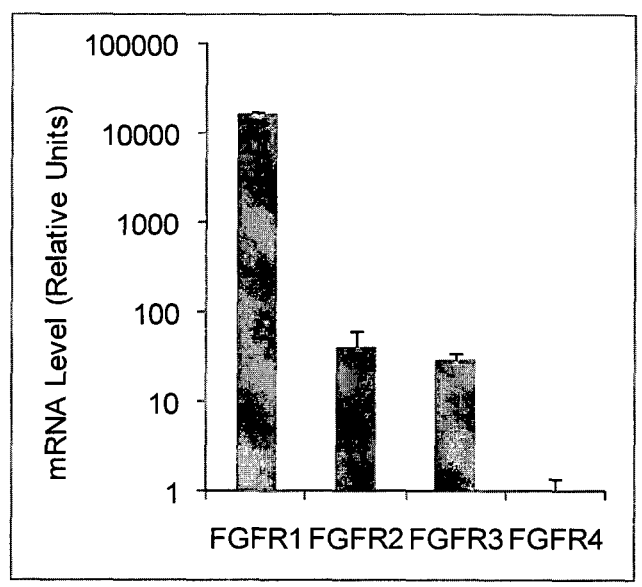
FIG. 3. (A) Graph showing mRNA expression levels of all four FGFR family members in MG63 cells. (B), (C) mRNA expression levels of FGFR1-3 were detected by Taqman Real-time Quantitative PCR analysis using commercial primers and probes from Applied Biosystems.
Figure 3B:
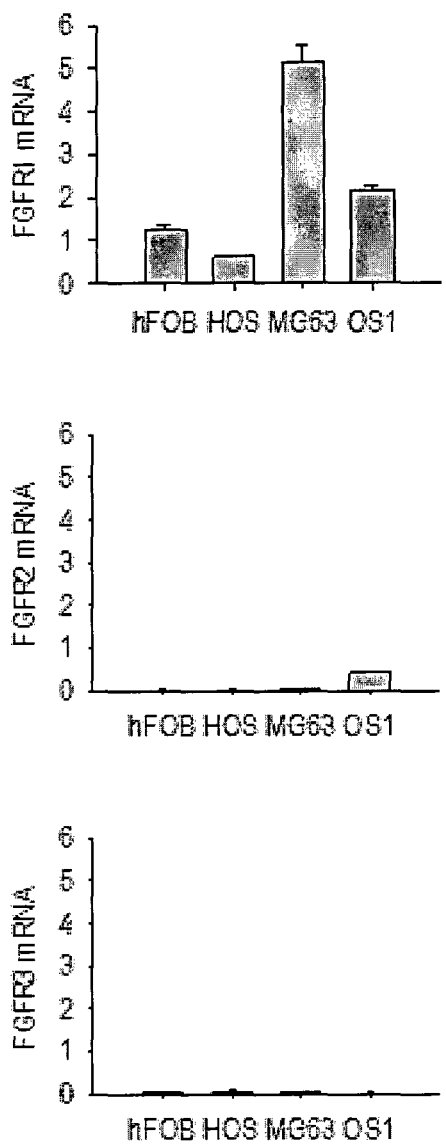
Figure 3C:
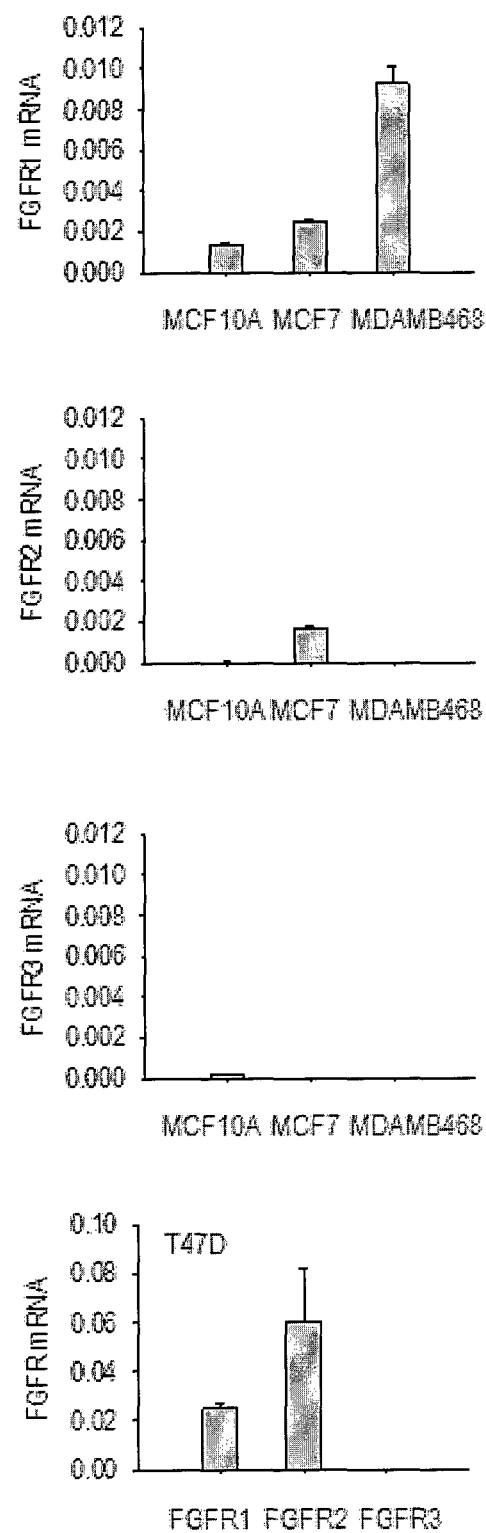

The mRNA expression levels of all four FGFR family members FGFR1-4 were detected in MG63 cells by Taqman Real-time Quantitative PCR analysis using commercial primers and probes from Applied Biosystems.
Results
In MG63, the transcripts of FGFR1 were more than 100 fold of that of FGFR2 and FGFR3, while the level of FGFR4 was barely detectable (FIG. 3). Therefore FGFR1 was the most abundant member of FGFR family in MG63, suggesting an important role of this receptor.

mRNA transcripts of FGFR1 were significantly more abundant than other FGFRs in all cells tested except in T47D. The mRNA level of FGFR1 is more than 100 folds of that of FGFR2 and FGFR3 in MG63 and MDA-MB468. Therefore generally speaking, FGFR1 transcripts are the most abundant member of FGFR family in these cancer cells, suggesting an important role of FGFR1.

Example 4

IMB-R1 specifically bound to FGFR1

Figure 4:
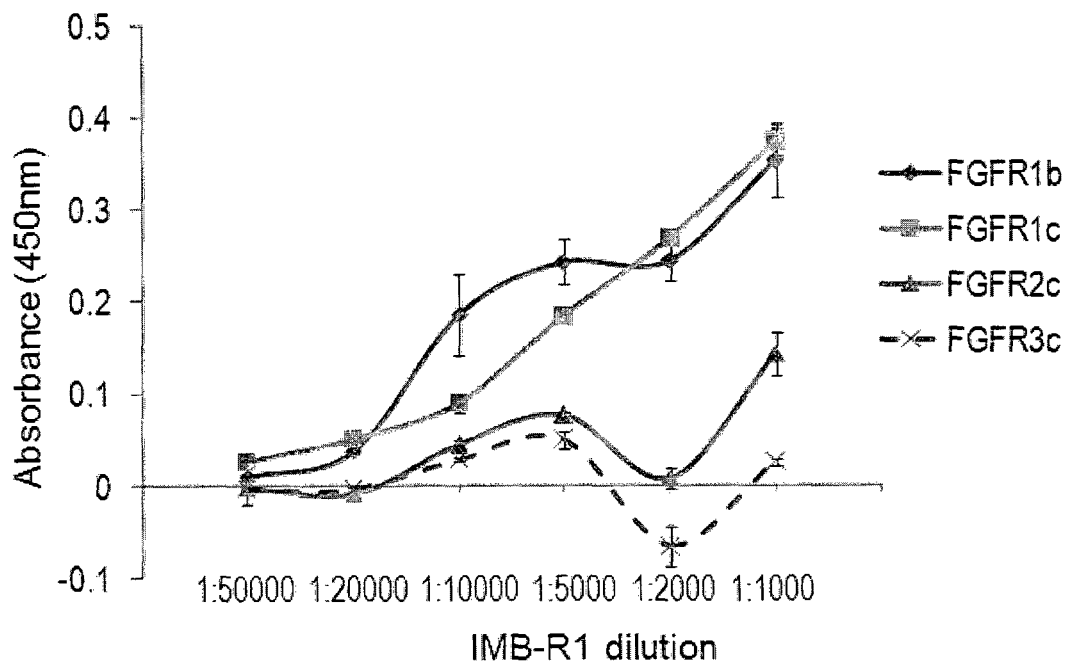
FIG. 4. Graph demonstrating specificity of binding of IMB-R1 for FGFR1b, FGFR1c over FGFR2c and FGFR3c.

To examine whether IMB-R1 has specificity for FGFR1 but not other FGFRs, we used ELISA assays. FGFR1, 2 and 3 have splice variants "b" and "c". The "c" splice form exhibits responsiveness to more FGF ligands than the "b" slice form, especially in the cases of FGFR2 and FGFR3. Therefore we only included "c" isoforms for FGFR2 and 3 in this assay. First, the ELISA plates were coated with goat anti-human IgG-Fc (Jackson ImmunoResearch Labs), followed by blocking with 2% BSA. The plates were next incubated with 100 ng/ml FGFRs isoforms conjugated with Fc fragment or control human IgG, and then incubated with various concentrations of IMB-R1 or normal rabbit IgG as the control. Thereafter, the bound antibodies were detected with HRP conjugated goat anti-rabbit IgG (Jackson ImmunoResearch Labs) and visualized by TMB substrate. The developed color was measured using Victor3 multiplate reader at wavelength 450 nm. The raw data were normalized by the readings of the control wells. Higher readings indicated higher affinity of IMB-R1 to the FGFRs.
Results The affinity of IMB-R1 to FGFR1b or FGFR1c was dose-dependently increased and the Ab450 reached approximately 0.37 in the case of FGFR1c at 1:1000 dilution. However, the absorbance of FGFR2c or 3c fluctuated around the low level 0.14). Our data demonstrates that IMB-R1 is specific to FGFR1 and not FGFR2 or FGFR3 (FIG. 4).

Example 5

IMB-R1 Specifically Blocked the Phosphorylation of FGFR1

Figure 5A:
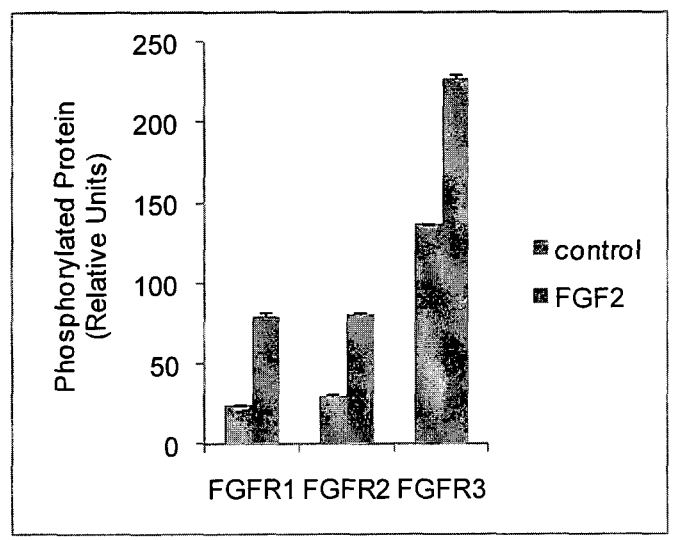
FIG. 5. (A), Graph showing FGF2 was able to stimulate the phosphorylation of FGFRs (FGFR1, FGFR2 and FGFR3) in MG63 cells. (B) Graph showing IMB-R1 specifically blocked the phosphorylation of FGFR1 (stimulated by FGF2) but not the phosphorylation of FGFR2 or FGFR3. (C) Graph showing fold change in tyrosine kinase activity.
Figure 5B:
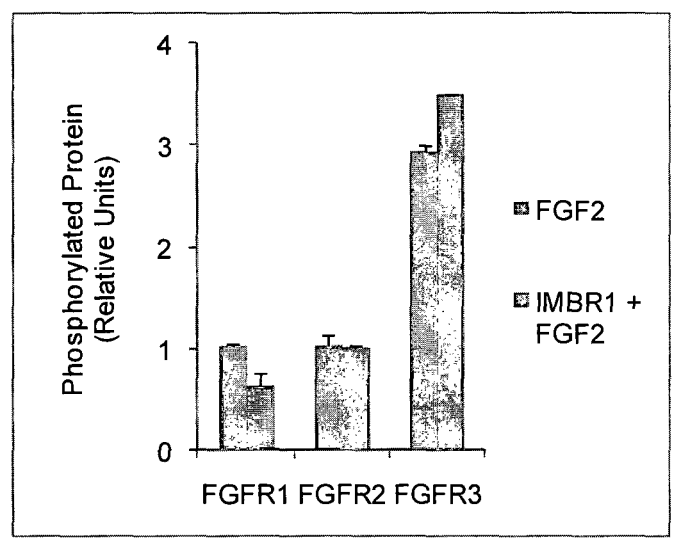

The levels of phosphorylated-FGFRs were examined by the Receptor Tyrosine Kinases Array (R&D Systems) in MG63. The cells were deprived of serum for 48 hours followed by:
 1. Treatment with 20 ng/ml recombinant human FGF2 (R&D Systems) for 5 minutes. The control cells were without treatment with FGF2.
 2. Treatment with IMB-R1 (1:250) for 1 hour then 20 ng/ml recombinant human FGF2 for another 5 minutes.
Thereafter, 500 µg cell lysates were used for the Receptor Tyrosine Kinases Array as per Manufacturer's instruction.
 3. MG63 cells were deprived of serum for 48 hours followed by treatment with IMB-R1 (1:250) for 1 hour then with 20 ng/ml recombinant human FGF2 for 10 minutes. The cells were then lysed and the protein samples were prepared for Western Blotting to detect the phosphorylation of FRS2α.
Results FGF2 was able to stimulate the phosphorylation (indicating activation) of FGFR1, 2 and 3 FIG. 5(A). In the presence of IMB-R1, the FGF2 stimulated phosphorylation of FGFR1 was inhibited, but not that of FGFR2 or FGFR3 (FIG. 5B). This data demonstrated that IMB-R1 specifically blocked FGFR1 activity but not the activity of FGFR2 or 3.

Figure 5C:
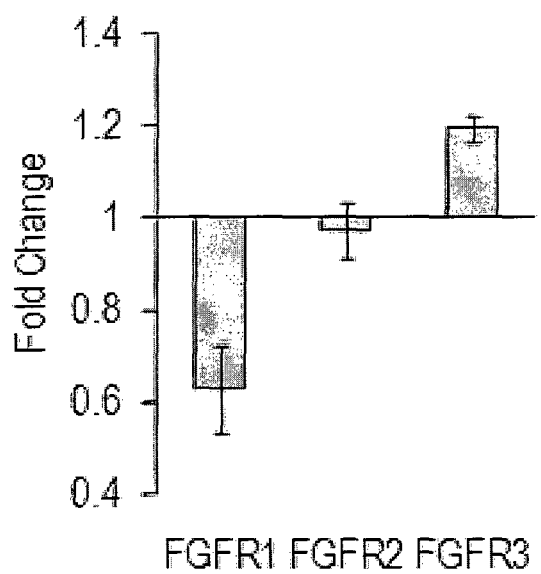

FRS2α is the direct downstream target of FGFRs. Once FGFRs are phosphorylated, they would activate the phosphorylation of FRS2α. Therefore, the change of the phosphorylated FRS2α is another indicator of the activity of FGFR signaling. MG63 cells were starved by serum deprivation for 48 hours before stimulated by 20 ng/ml FGF2 for 10 minutes. To test if IMB-R1 was able to affect the phosphorylation of FRS2α we treated the cells with IMB-R1 (1:250) 1 hour before FGF2 stimulation. The results are shown in FIG. 5C. Without IMB-R1, FGF2 stimulated the phosphorylation of FRS2α at tyrosine 196 (Y196) and several other tyrosine sites, since the bands shifted to the higher molecular weight indicating hyper-phosphorylation. However, in the presence of IMB-R1, the bands shifted to the lower molecular weight, indicating less tyrosine sites were phosphorylated. Notably, the intensity of the bands was increased, suggesting that more FRS2α molecules were phosphorylated on Y196 by IMB-R1. Therefore, IMB-R1 was able to significantly affected the phosphorylation pattern of FRS2α. It caused more FRS2α molecules to be phosphorylated on Y196 but inhibited the phosphorylation of more than one other tyrosine sites.

Example 6

IMB-R1 Inhibited the Growth of Osteosarcoma and Breast Cancer Cells

Figure 6A:
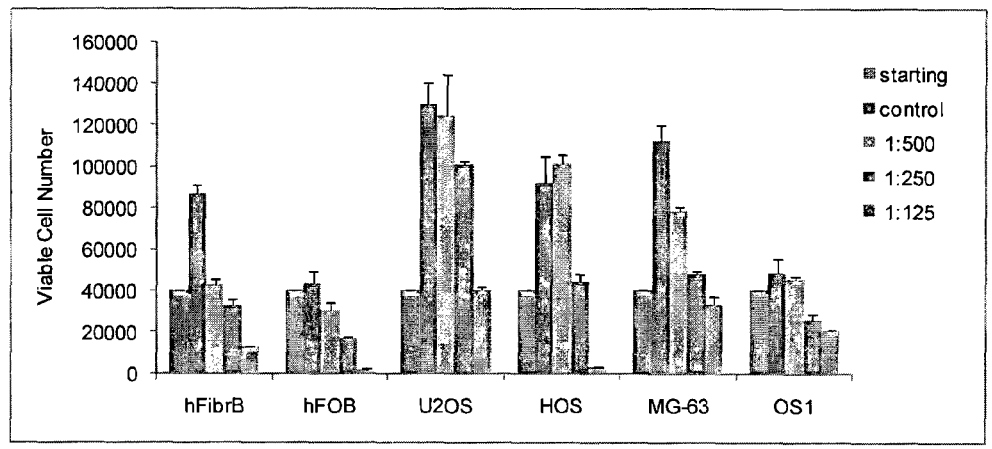
FIG. 6. Graphs showing IMB-R1 induced inhibition of growth of osteosarcoma and breast cancer cells.
Figure 6B:
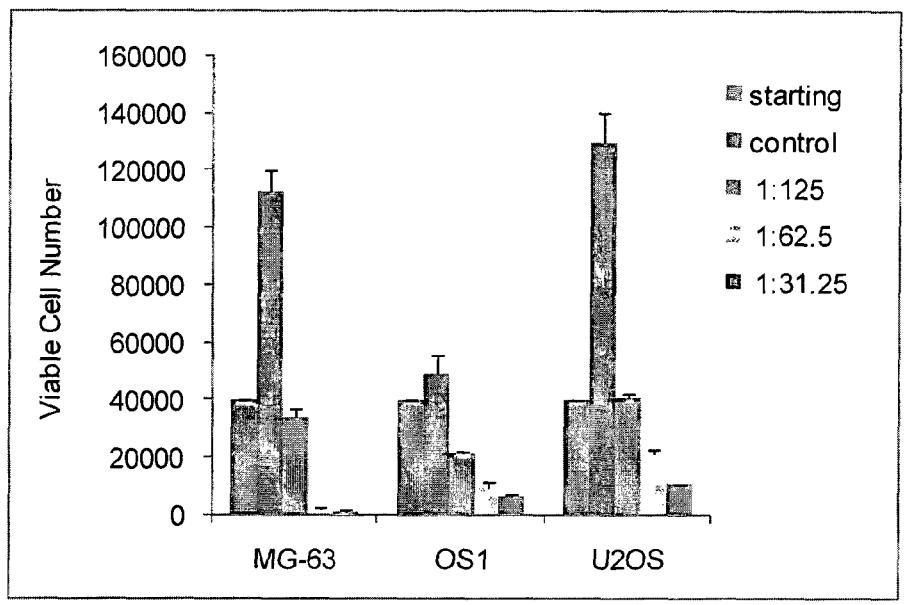
Figure 6C:
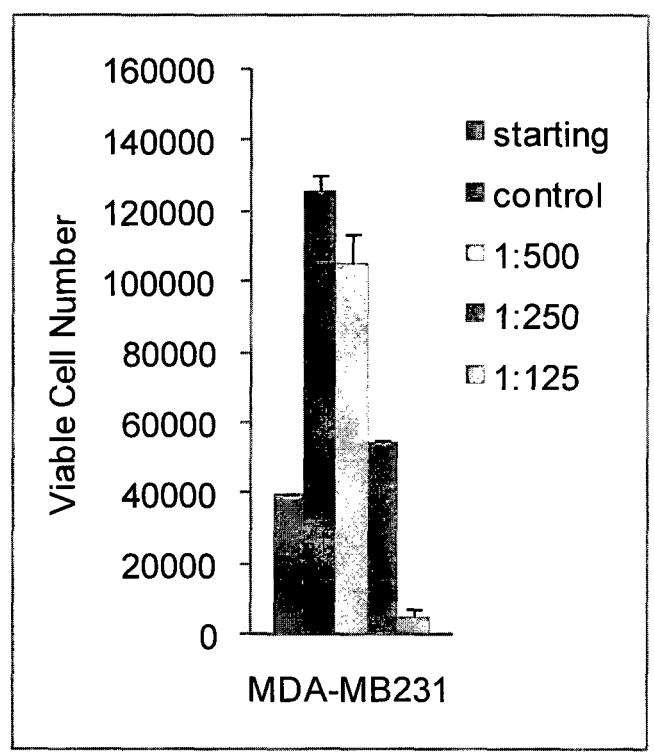
Figure 6D:
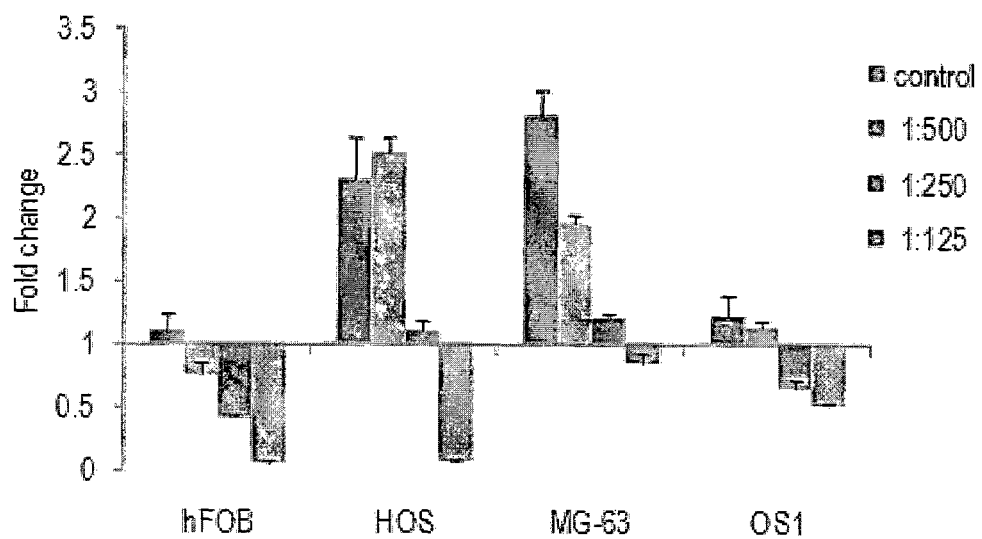
Figure 6E:
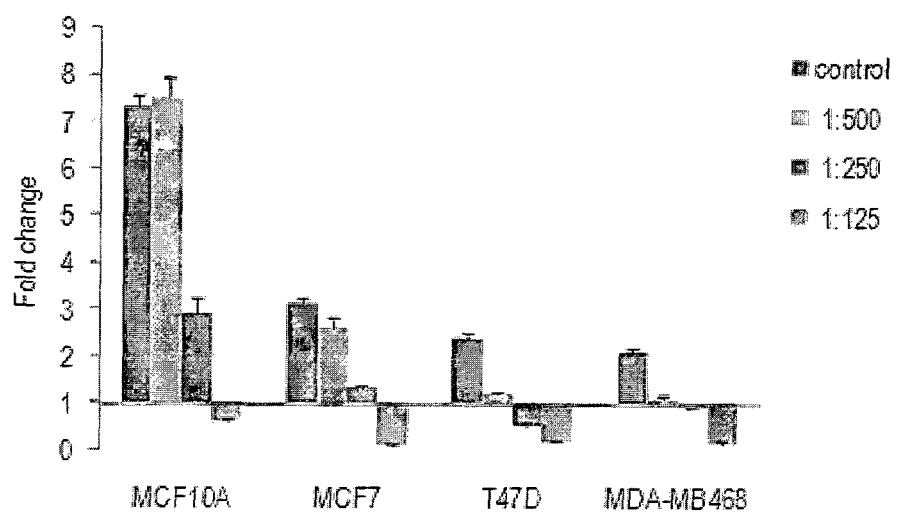

The effect of IMB-R1 on cell growth was examined by the GUAVA EasyCyte flow cytometry system in normal human fibroblasts (hFibrB), hFOB, osteosarcoma cells U2OS, HOS, MG63 and OS1, human mammary epithelial cells (MCF10A) and breast cancer cell lines MDA-MB231, MCF7 and T47D. The cells were seeded in triplicates at 20,000 cells/cm$^2$ in 24-well plates, except MDA-MB468 which was plated at 100,000 cells/cm$^2$. After 24 hours, cells were either treated with rabbit IgG as the control (the vehicle control for IMB-R1 which was produced as the rabbit anti-sera), or IMB-R1 at a serial of dilutions of 1:500, 1:250 or 1:125. For MG63, OS1 and U2OS, even higher dosages of IMB-R1 were applied which was 1:62.5 or 1:31.25 dilutions. 48 hours after treatment, the viable cell numbers were counted using the GUAVA Viacount Program and used to plot the graph (FIG. 6). The 'starting' cell numbers which were seeded for the assay were also included. hFOB is the normal cell control for osteosarcoma cells, while MCF10A is the normal cell control for breast cancer cells.
Results IMB-R1 inhibited the cell growth in a dose-dependent manner (FIGS. 6A and 6C). In MG63 cells, IC$_{50}$ (the dose to induce 50% inhibitory effect) was approximately 1:250 dilution of IMB-R1. In MG63, OS1 and U2OS, IMB-R1 did not eliminate the population as effectively as in other cells. Therefore, we increased the dose and found it was able to kill most of the cells at a higher dose (FIG. 6B). The negative fold change (less than 1) indicated that IMB-R1 killed the cell population since the cell number is less than the starting cell number. It takes a higher dose of IMB-R1 to kill MCF10A (≥1:125) than breast cancer cells (≥1:250), suggesting normal mammary epithelial cells are less sensitive to IMB-R1 than breast cancer cells, which shows that certain dosage of IMB-R1 can target breast cancer cells without harming normal mammary cells. While in the case of bone tissue, it is opposite. At (≥1:500 dose IMB-R1 was sufficient to kill hFOB, but it generally needed higher dose (≥1:250) to do the same thing to osteosarcoma cells. Thus, one side effect of IMB-R1 when administered systemically is expected to be osteoporosis. But this could be avoided if IMB-R1 were delivered locally to the tumor itself.

Example 7

Comparison of IMB-R1 with Commercial Reagents

Two common types of reagents to block FGFR signalling are available in the market. One type are small chemical molecules that inhibit kinase activity of FGFRs. The most potent and widely used of these is SU5402, and PD166866 and PD173074 are more recently reported. The other types of reagents are the neutralizing antibodies. The only commercially available neutralizing antibody against FGFR1 we are aware of is a monoclonal antibody provided by R&D Systems (# MAB765). We tested the effectiveness of these reagents to block the growth of MG63 using GUAVA Viacount system. To demonstrate the doses of the commercial FGFR1 antibody were within the effective range, we measured if the FGFR1 antibody could inhibit FGF2-stimulated BrdU incorporation into the cells.

Results

Figure 7A:
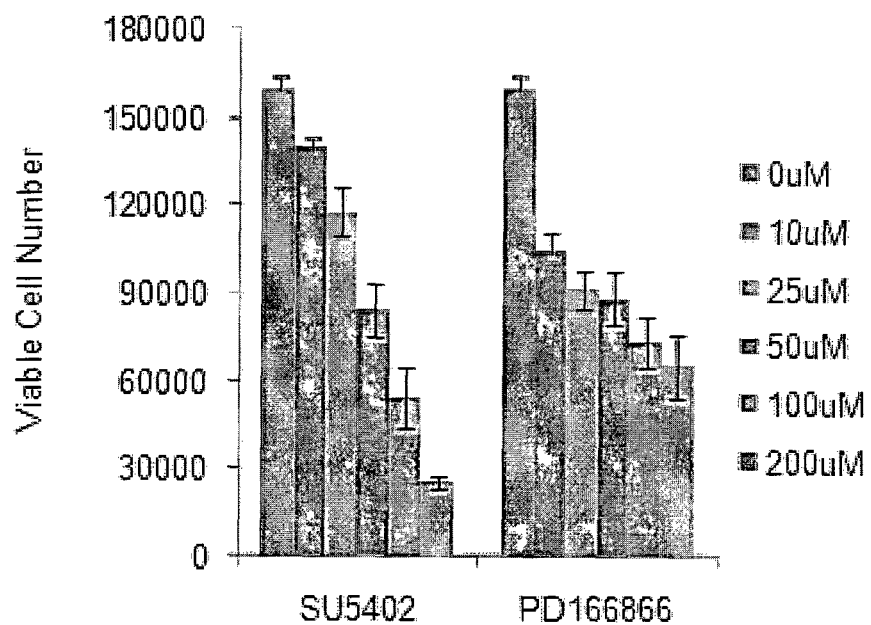
FIG. 7. (A) Graph showing effect of SU5402 and PD166866 on growth of MG63 cells. (B) Graph showing effect of #MAB765 (R&D Systems) on growth of MG63 cells. (C) Graph showing effect of #MAB765 on BrdU incorporation in FGF2 stimulated MG63 cells. (D) Graph showing effect of PD173074 on growth of MG63 cells.
Figure 7B:
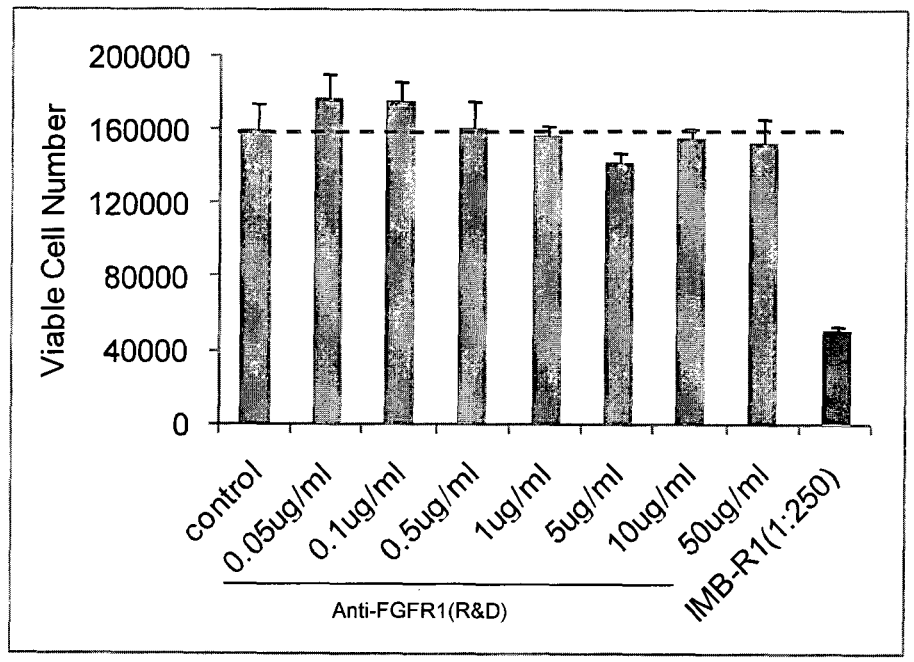
Figure 7C:
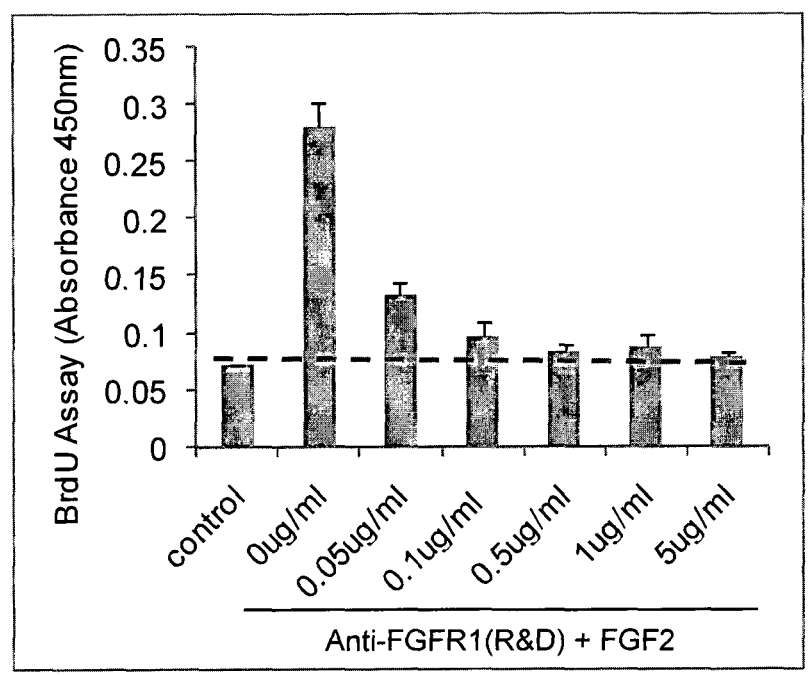
Figure 7D:
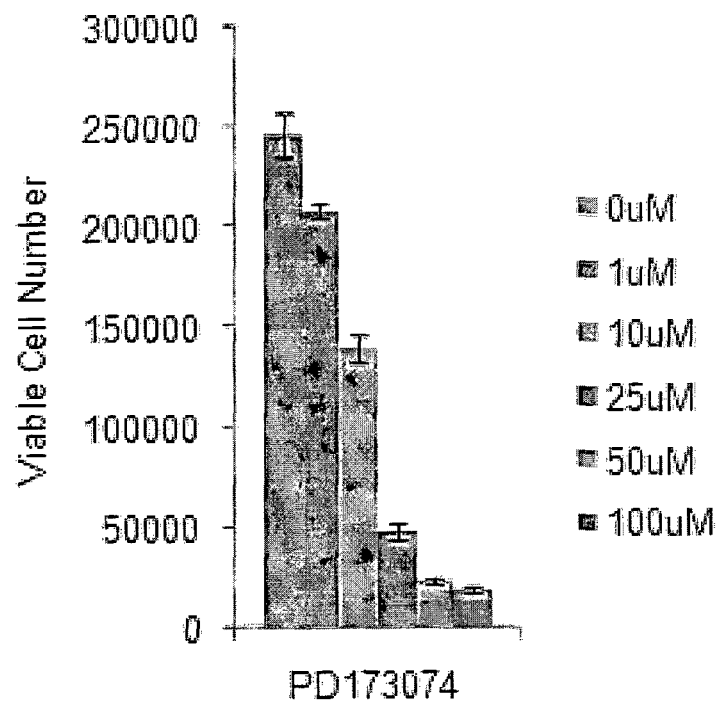

MG63 cells were treated with chemical inhibitors for 48 hours at indicated doses. SU5402, PD166866 and PD173074 were able to inhibit the growth of MG63 dose dependently (FIGS. 7A and D). At 50 μM, SU5402 and PD166866 repressed cell growth approximately by 50%, while 10 to 25 μM PD173074 was able to induce 50% cell growth inhibition, there PD173074 is more potent than the first two. The commercial FGFR1 antibody (#MAB765) did not affect MG63 cell growth even at the dose up to 50 μg/ml, while it significantly inhibited FGF2-stimulated BrdU incorporation even at a dose of 0.05 μg/ml (FIGS. 7B and 7C).

Example 8

IMB-R1 Increased Cell Apoptosis

The observation that IMB-R1 dramatically reduced cell numbers suggested that this antibody might also induce apoptosis. Thus we treated MG63 with 1:250 dilution of IMB-R1 or equal volume of rabbit IgG for 24 hours and then stained the cells with Annexin V-FITC and Propidium Iodide (PI) (BD Biosciences). Annexin V binds to phosphatidylserine which is only present on the outer layer of cell membrane at the early stage of apoptosis. Therefore positive staining of Annexin V indicates early apoptosis. PI is unable to penetrate the intact cell membrane. Only when the membrane breaks down at the late stage of apoptosis, PI can enter and stain the cell. After staining, the cell population was analyzed by BD FACS Array system. The viable cells were negative of either Annexin V-FITC or PI staining, which was shown in Q3; the early apoptotic cells were positive of Annexin V-FITC but negative of PI staining, which was shown in Q4; the late apoptotic or dead cells were positive of both staining, which was shown in Q2. The percentage of positive cells in each population was plotted in the graphs.

Results

Figure 8A:
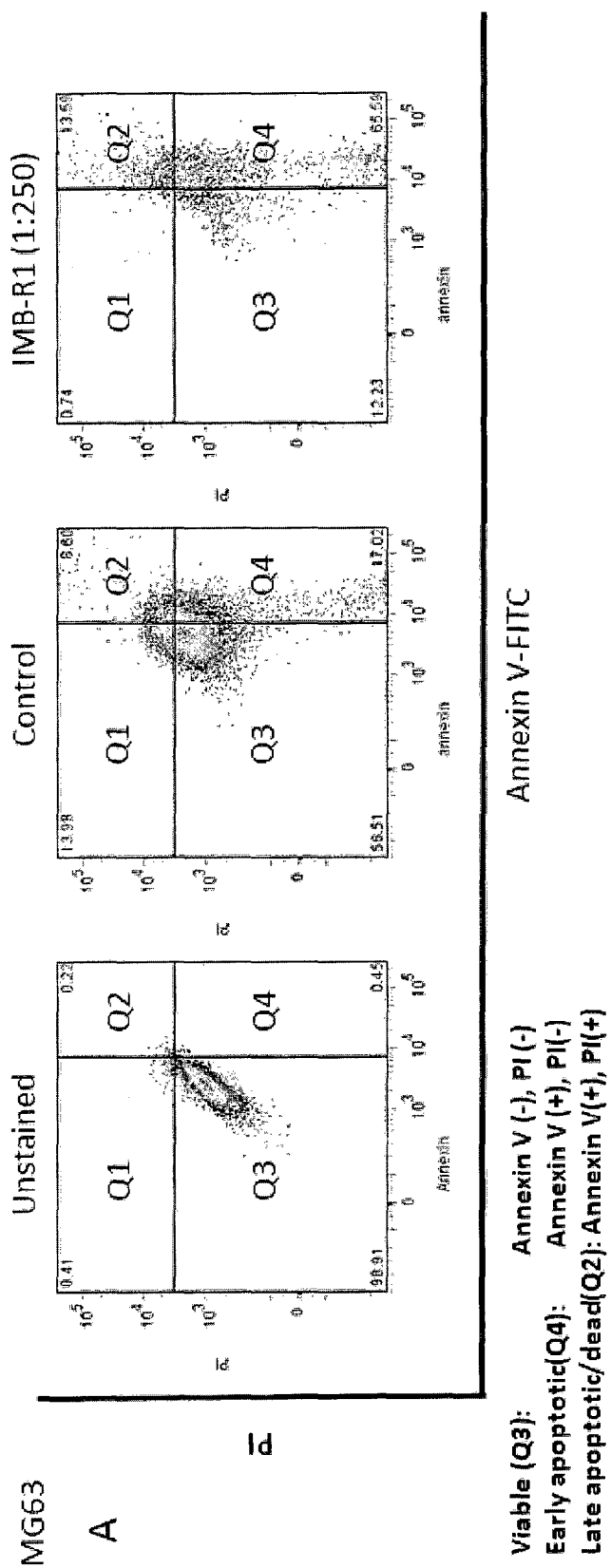
FIG. 8. (A) Analysis of Annexin V-PI staining as an indicator of apoptosis in MG63 cells. (B) Bar graphs showing percentage of viable vs. apoptotic cells and percentage cells in early vs. late stage apoptosis in control MG63 cells and MG63 cells treated with IMB-R1. (C) Analysis of Annexin V-PI staining as an indicator of apoptosis in MDA-MB-468 and T47D cells. (D) Analysis of Annexin V-PI staining as an indicator of apoptosis in hFOB and MCF10A cells.
Figure 8B:
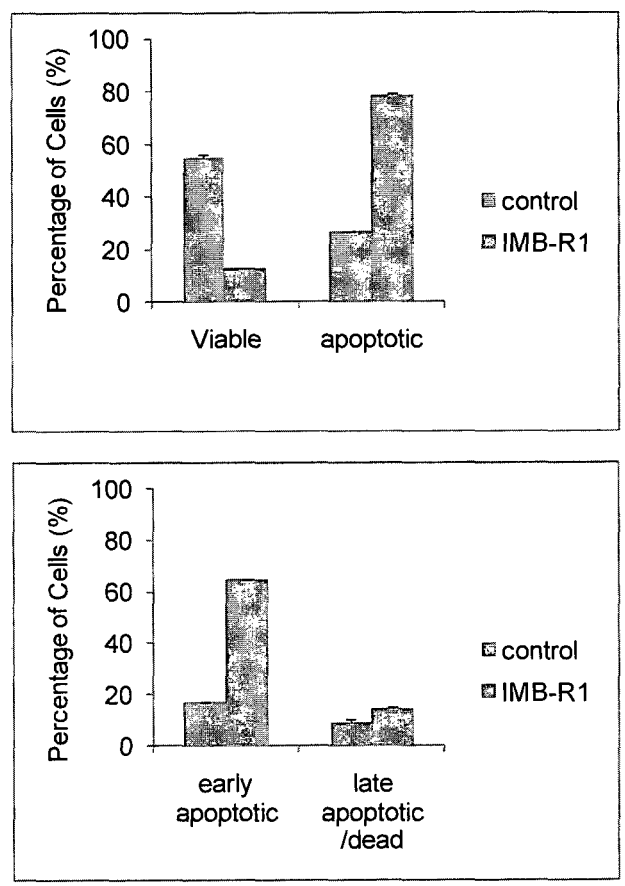

MG63 cells without any staining were used as the negative control and for gating purpose. Since they were not stained, the whole population was expected to appear within Q3. The control cells were MG63 treated with rabbit IgG. Comparing the diagram of the control cells with that of the IMB-R1 treated cells, we clearly observed a shift of the population from left (viable) to right (apoptotic) (FIG. 8A). The percentage of cells were then plotted as bar graph and shown in (FIG. 8B). MG63 treated with IMB-R1 reduced the sub-population of viable cells from 55% to 13%, while increased the sub-population of apoptotic cells from 26% to 79%. When we zoomed into the apoptotic population, we found that IMB-R1 increased early apoptotic cells by 3.8 fold while late apoptotic cells by 1.6 fold.

Example 9

IMB-R1 Increased Caspase 3 Activity

We further examined the effect of IMB-R1 on Caspase 3 activity using an assay kit from Biovision. Caspase 3 is activated at the early stage of apoptosis, so it is used as a common marker of apoptosis. Staurosporine, known as the inducer of caspase 3 activity, was used in this assay as the positive control. We first treated MG63 cells with increasing dose of staurosporine for 24 hours to determine the working dose.

Results

Figure 8C:
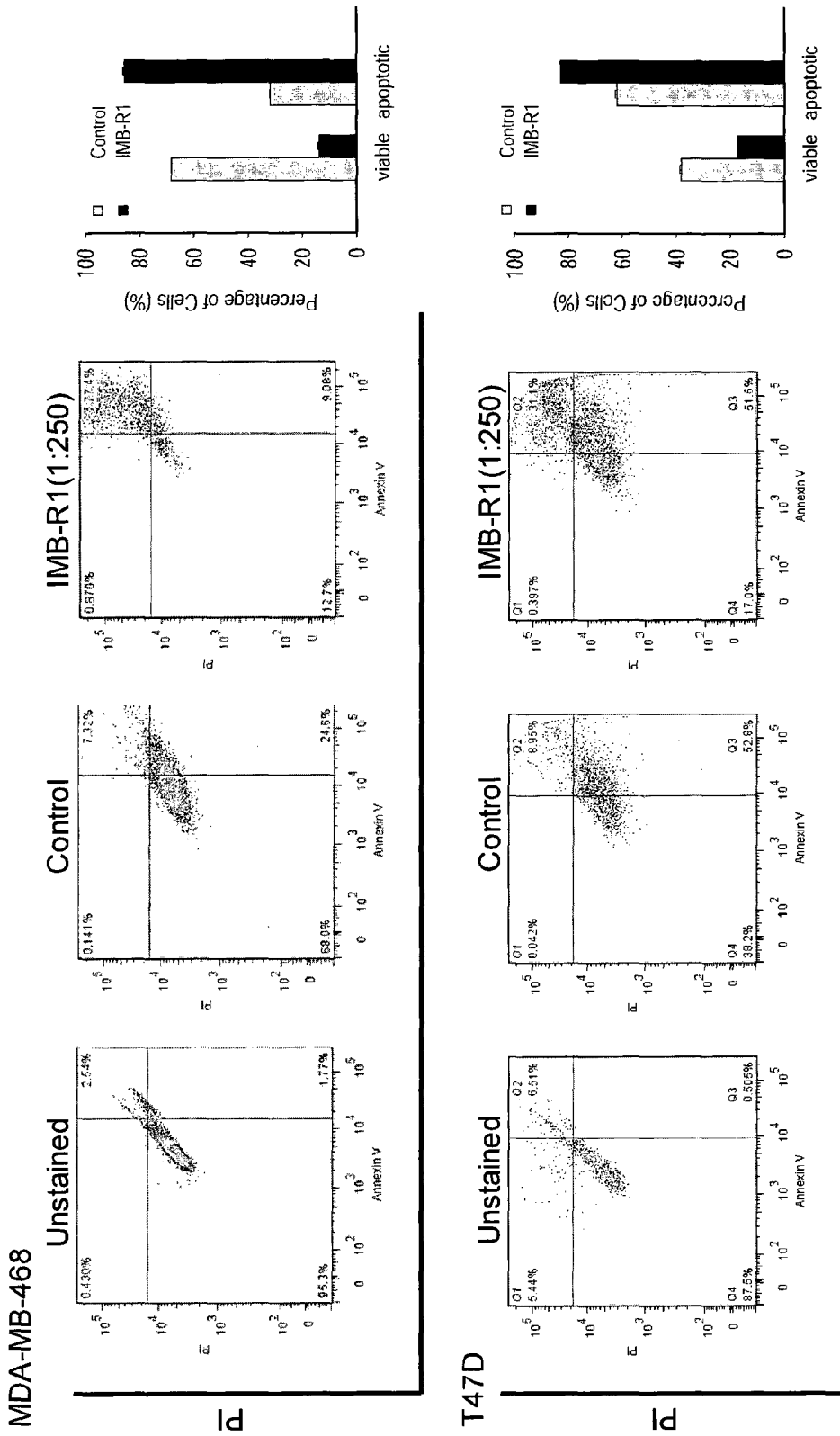
Figure 8D:
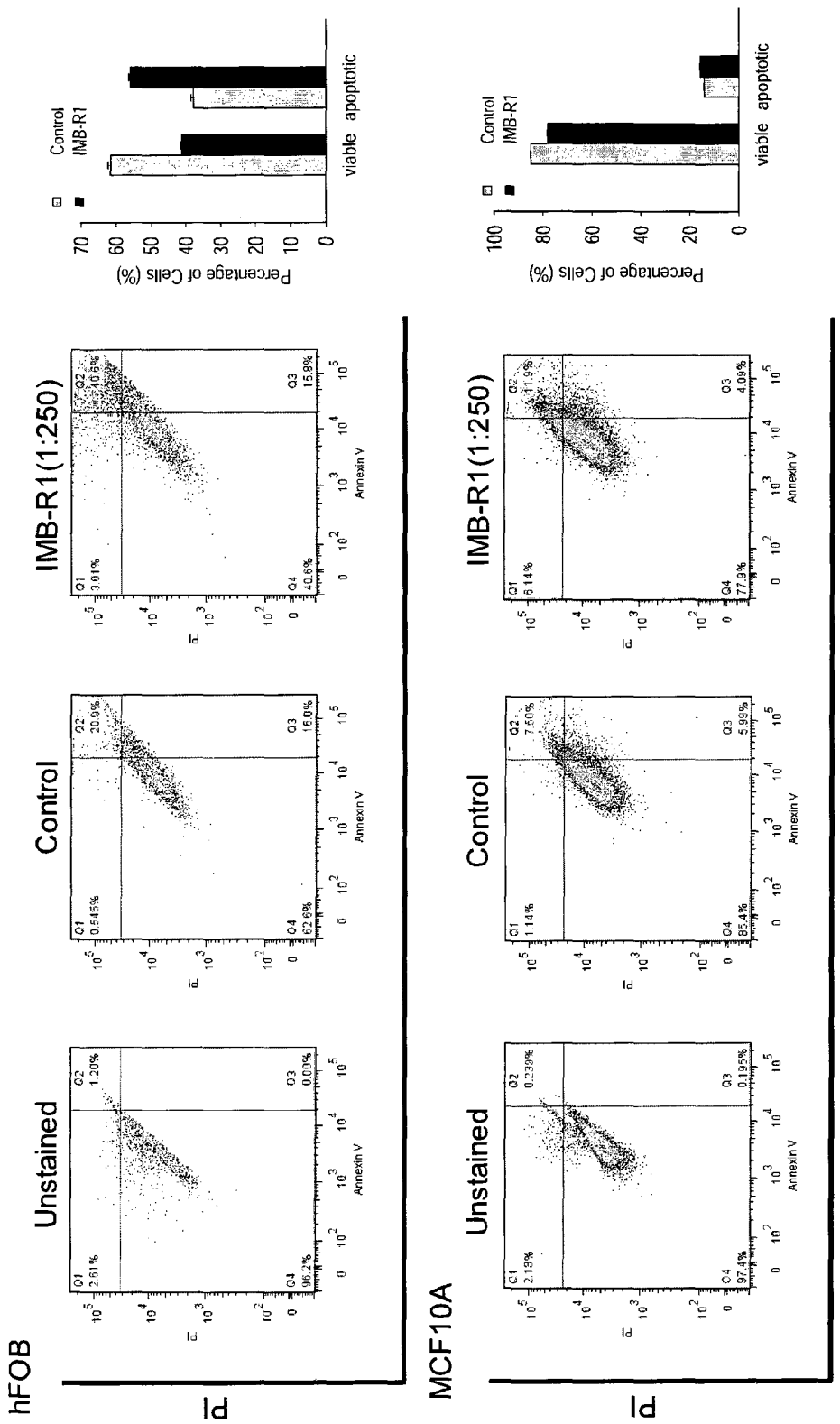
Figure 9A:
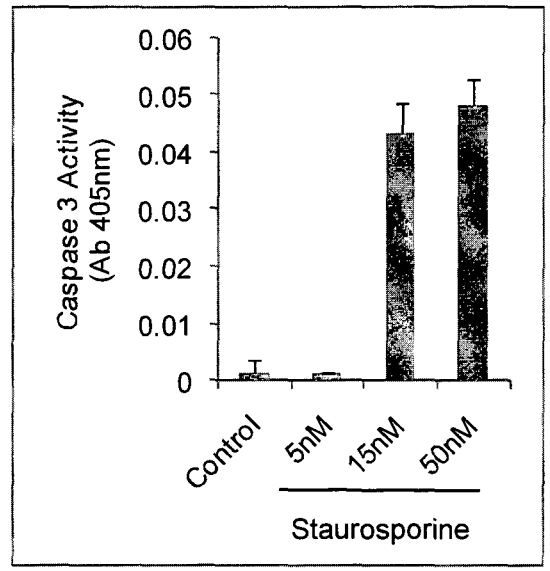
FIG. 9. Graphs showing the effect of IMB-R1 on Caspase 3 activity in MG63 cells.
Figure 9B:
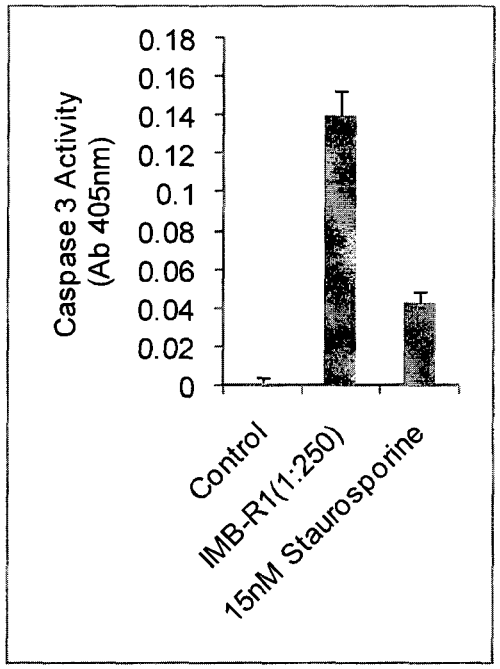

As shown in FIG. 9A, 15 nM staurosporine was sufficient to activate Caspase 3 and was chosen as the working dose for MG63 cells. IMB-R1 dramatically activated Caspase 3 at 1 in 250 dilution and was several folds more potent than 15 nM Staurosporine (FIG. 9B). Therefore, together with the data in FIG. 8, we demonstrated that IMB-R1 strongly induces apoptosis of MG63 cells.

Next we examined whether IMB-R1 induced apoptosis in the breast cancer cells. We tested it in two lines MDA-MB468 and T47D. We treated them with 1:250 dilution of IMB-R1 or equal volume of rabbit IgG for 24 hours and then stained the cells with Annexin V-FITC and PI.

Results: As shown in FIG. 8C, IMB-R1 induced a shift of the population from left (viable) to right (apoptotic) in these two breast cancer cell lines. IMB-R1 reduced the sub-population of viable MDA-MB468 from 68.0% to 13.5%, while increased the sub-population of apoptotic cells from 31.8% to 85.4%. In parallel, T47D treated with IMB-R1 lost the sub-population of viable cells from 38.1% to 17.0%, when more cells underwent apoptosis (from 61.8% to 82.7%).

We have previously noted that bone tissue appeared to be more sensitive to IMB-R1 than breast tissue. Therefore, we also examined how hFOB and MCF10A, the normal cells in each tissue, responded to the apoptotic activity of IMB-R1. These cells were also treated with same dose of IMB-R1 as above for 24 hours.

Result: As shown in FIG. 8D the viable hFOB was reduced by IMB-R1 from 61.6% to 41.2%, while apoptotic cells were simultaneously raised from 37.8% to 55.7%. In contrast, the viability of MCF10A was barely affected at this dose of IMB-R1. Therefore, IMB-R1 is more toxic to bone than to mammary gland. Taken the data in Slide 9-11 together, IMB-R1 caused 4.2 folds of cell death in osteosarcoma cells (MG63), 1.5 folds in normal osteoblasts (hFOB), 2.2-5 folds in breast cancer cells (MDA-MB468 and T47D), and no cell death in normal mammary cells (MCF10A), compared with no IMB-R1 treatment. It means IMB-R1 is more toxic to cancer cells than to normal cells, making it a good candidate as anti-cancer therapeutics for further development.

Example 10

IMB-R1 Affected Tumor Repressors and Apoptotic Proteins

Next we analyzed the effect of IMB-R1 on proteins involved in apoptosis or tumor progression by Western Blotting. Cells were treated with IMB-R1 (1:250 dilution) for 48 hours and the protein lysate were prepared with Laemmli buffer. The blot for actin was used to show the equal loading of total proteins. We also extracted RNA from the above-treated cells and determined the effect of IMB-R1 on the transcription (mRNA level) of the key molecules of the above using Taqman Realtime QPCR.

Figure 10A:
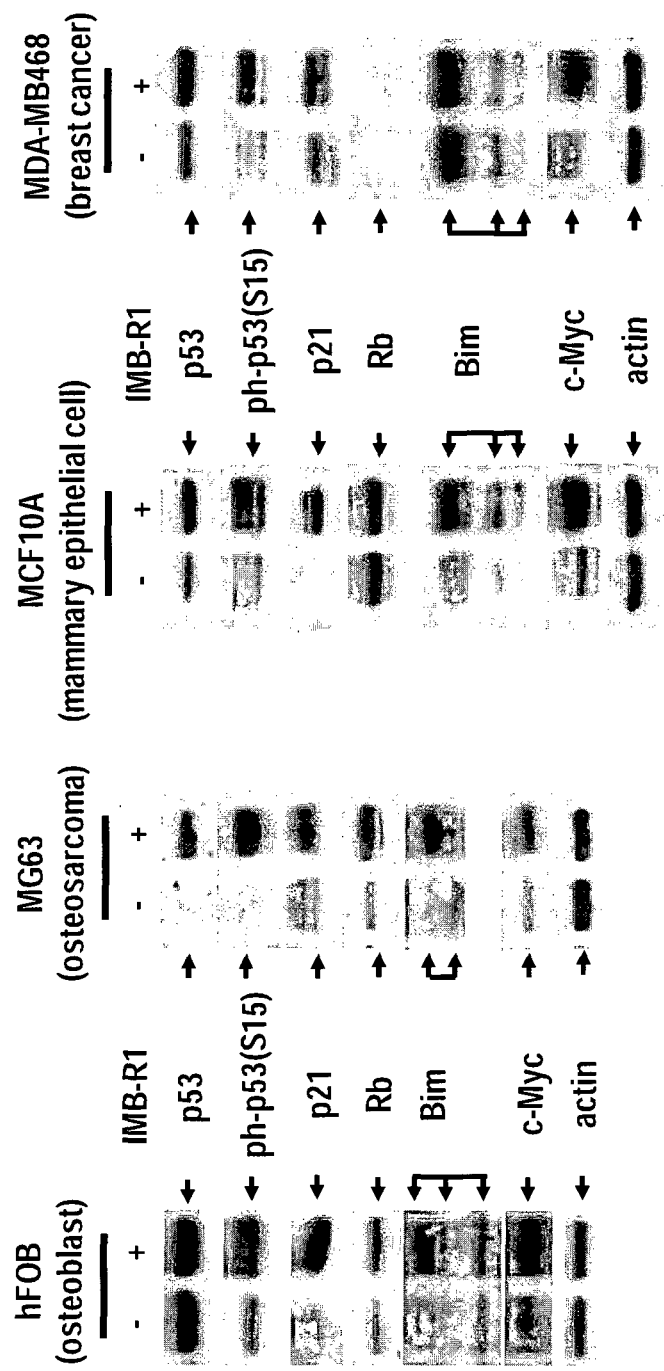
FIG. 10. (A) Western blot showing effect of IMB-R1 on expression of protein markers in hFOB, MG63, MCF10A and MDA-MB468 cells. (B) Graphs showing effect of IMB-R1 on mRNA expression for p53, p21, c-Myc and Rb in MG63 cells.
Figure 10B:
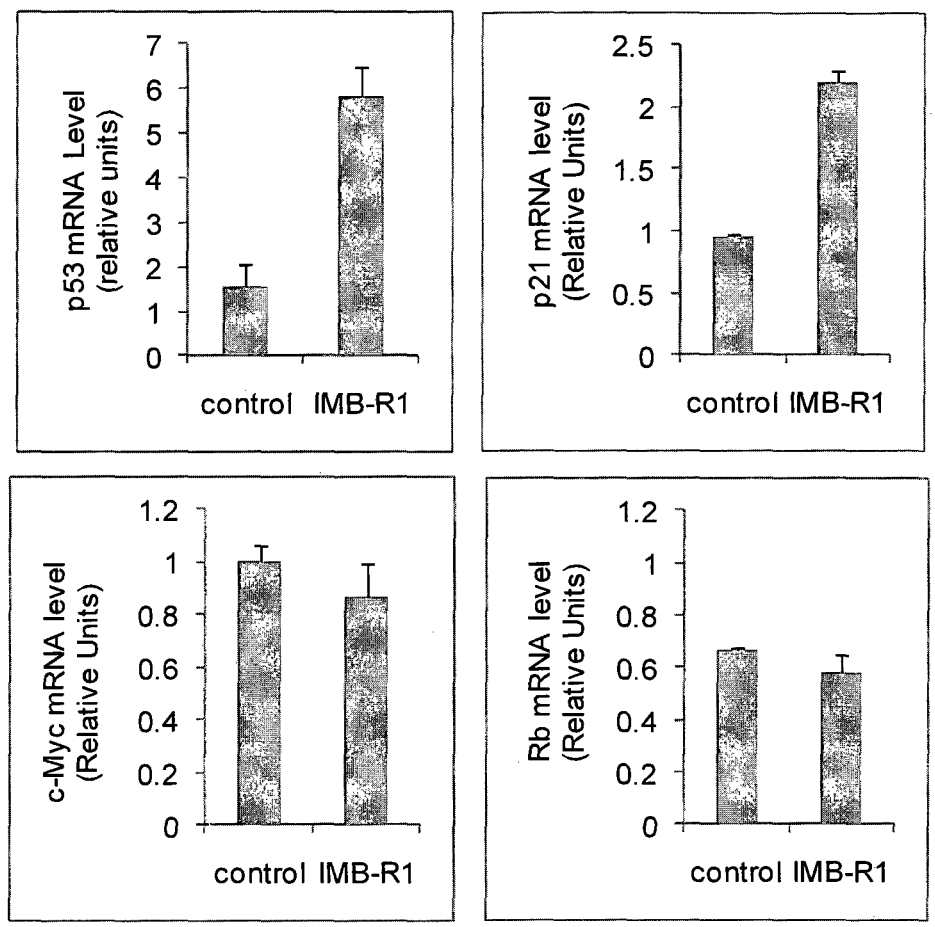

Results:

IMB-R1 treatment significantly increased the protein level of tumor suppressor p53 in MG63, MCF10A and MDA-MB468, but not that in hFOB. However, it increased the phosphorylation of p53 in all four cell types, suggesting that IMB-R1 activated p53. p53 is the key molecule that controls the progression of apoptosis, and is often inactivated during tumor development. The cell cycle inhibitor p21 is also one target gene of p53. It was up-regulated by IMB-R1 in all cells tested, which is consistent with the activation of p53 observed (FIG. 10B). Another important tumor suppressor is the retinoblastoma protein (Rb), which was increased by IMB-R1 in hFOB and MG63, but not in MCF10A. It was not expressed in MDA-MB468. Rb appeared to be one target protein of IMB-R1 in bone tissue but not in the breast tissue. IMB-R1 also potently increased Bim, a pro-apoptotic protein, in hFOB, MG63 and MCF10A, but minimally in MDA-MB468. Notably, c-Myc, of which the important role in apoptosis has been focussed recently, was universally increased by IMB-R1. The effects of IMB-R1 on these proteins involved in apoptosis and tumorigenesis suggested that IMB-R1 promoted apoptosis ad could be used to antagonize tumor growth.

Example 11

IMB-R1 Blocked FGF2 Stimulated MG63 Cell Growth

Figure 11A:
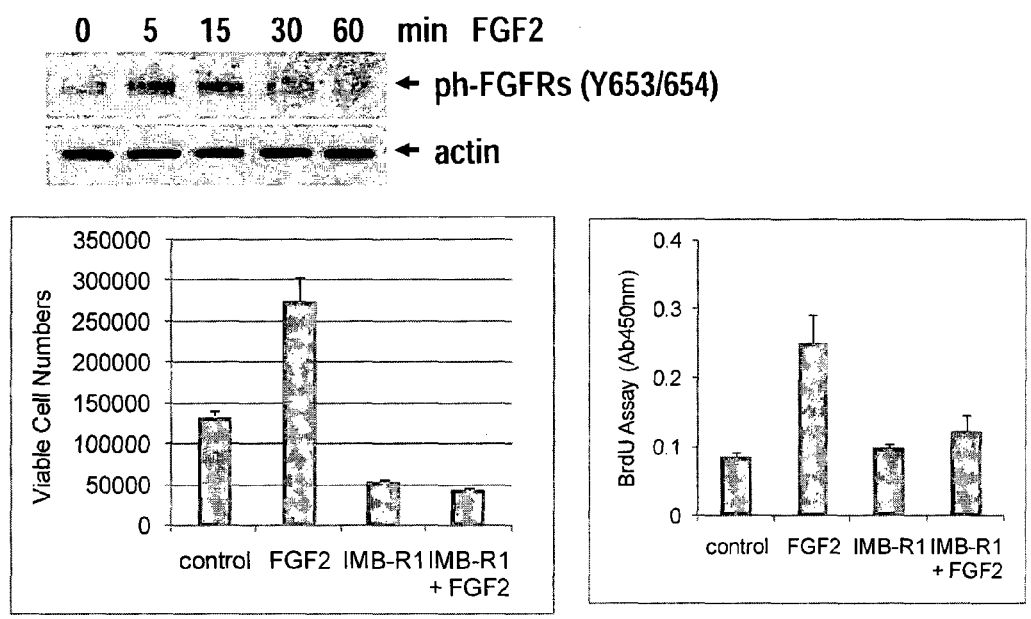
FIG. 11. (A) Western blot showing effect of FGF2 on phosphorylation of FGFRs in MG63 cells. Graphs showing effect of FGF2 and IMB-R1 on cell proliferation in MG63 cells. (B) Analysis of Annexin V-PI staining as an indicator of apoptosis in MG63 cells, with and without IMB-R1 and FGF2. (C) Graph showing percentage of viable and apoptotic MG63 cells following treatment with FGF2 and/or IMB-R1. (D) Graph showing Caspase 3 activity in MG63 cells following treatment with FGF2 and/or IMB-R1.
Figure 11B:
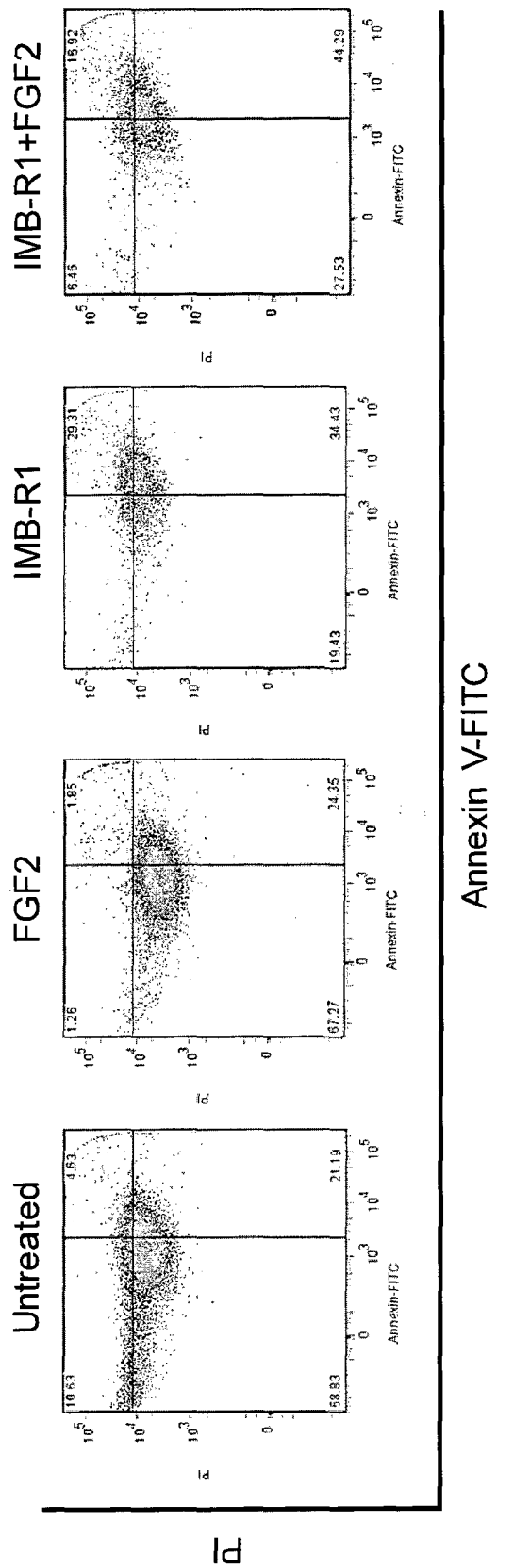
Figure 11C:
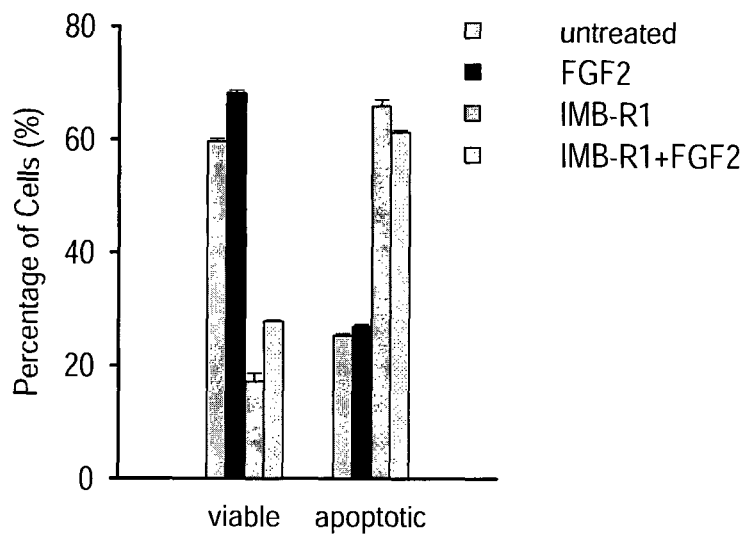

The previous data showed that IMB-R1 inhibited FGF2/FGFR1 signalling. We next examined whether FGF2 regulated cell apoptosis and IMB-R1 blocked its effect. MG63 cells were treated with IMB-R1 (1:250) 1 hour before FGF2 (20 ng/ml). 24 hours later, cells were harvested and stained with Annexin-PI. Thereafter, cells were analysed by flow cytometry (FIG. 11B). The percentage of positive cells in each population was plotted in the graphs (FIG. 11C). We further examined the effect of IMB-R1 and FGF2 on Caspase 3 activity using the assay kit from Biovision. Caspase 3 is activated at the early stage of apoptosis, so it is used as a common marker of apoptosis. The dose of reagents and the time point chosen were same to those in Annexin-PI staining assay.

Figure 11D:
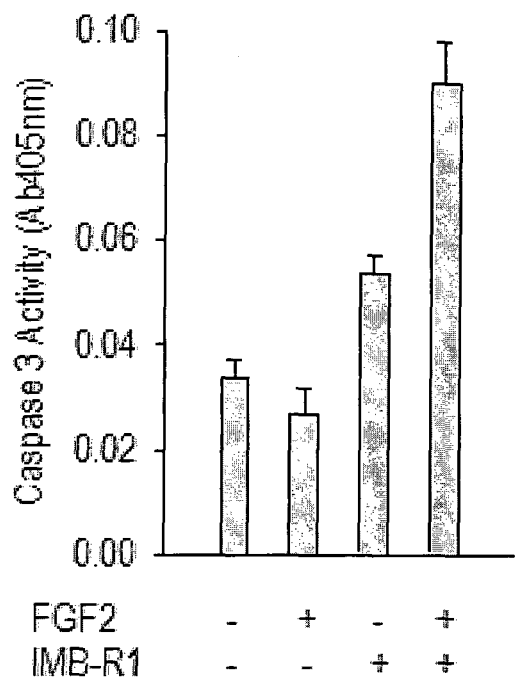

Result: FIGS. 11 (B) and (C): FGF2 reduced the amount of late apoptotic cells and increased viable population, showing that FGF2 protected cell against apoptosis, especially targeting late apoptotic cells. In the presence of IMB-R1, FGF2 treated population contained 14 folds more late apoptotic cells and 1.9 folds more early apoptotic cells compared with cells treated only with FGF2, therefore IMB-R1 blocked the protection of FGF2 on the cells. The reduced level of late apoptotic cells in the presence of IMB-R1 and FGF2 compared with IMB-R1 treatment alone suggested that IMB-R1 did not completely block FGF2 activity. This might be due to the dosages of these two reagents. FIG. 11(D), FGF2 slightly decreased caspase 3 activity, again suggesting that early apoptosis might not be the primary target of FGF2. IMB-R1 increased caspase 3 activity, similar to the previous observation (in 1st filing). The combined treatment of IMB-R1 and FGF2 induced even higher level of caspase 3 activity, showing that FGF2 could not improve cell survival in the presence of IMB-R1. The higher amount of early apoptotic cells may be the result of more cells shifting from late apoptosis to early apoptosis due to the leakage of FGF2 activity, which is similar to what we have seen in FIG. 11(C). In summary, IMB-R1 was able to inhibit the positive FGF2 effect on cell survival.

FGF2 is one of the most studied FGF ligands that activate FGFR1 signalling. Since IMB-R1 neutralized FGFR1 signalling, we examined whether it also inhibited FGF2 stimulated cellular effects.

MG63 cells were deprived of serum for 48 hours and stimulated with 20 ng/ml FGF2 for 5 to 60 minutes (FIG. 11 Western blot). The cells were then lysed and the protein samples were prepared for Western Blotting to detect the phosphorylation of FGFRs.

Results 20 ng/ml FGF2 was able to induce an abundant increment of phosphorylated FGFRs as early as 5 minutes and the level sustained until 15 minutes and started to decline. This data demonstrated that the dose of FGF2 was sufficient to activate downstream signalling. Therefore we used this dose for the following assays.

MG63 cells were treated with 20 ng/ml FGF2, IMB-R1 (1:250 dilution), or pretreated with IMB-R1 1 hour before addition of FGF2. Cells without the above treatments were the control. After 2 days, the viable cell numbers were counted using GUAVA system as mentioned before.

Results

FGF2 was able to increase the cell proliferation by 1.9 folds, while in the presence of IMB-R1 the proliferative effect of FGF2 was completely diminished (FIG. 11). IMB-R1 alone potently reduced the cell number, which is consistent with the previous data. This result demonstrated that IMB-R1, as an FGFR1 neutralizing antibody, was capable of blocking the activity of FGF2.

Example 12

IMB-R1 Inhibited FGF2 Stimulated ERK Activation

ERKs are the major signalling pathways that are phosphorylated and activated by FGF2 in many cells. Here we first examined if FGF2 also activated ERKs in MG63.

The cells were deprived of serum for 2 days and stimulated with 20 ng/ml FGF2 for 5 to 60 minutes. The cells were then lysed and the protein samples were prepared for Western Blotting to detect the phosphorylation of ERKs.

Results

Figure 12:
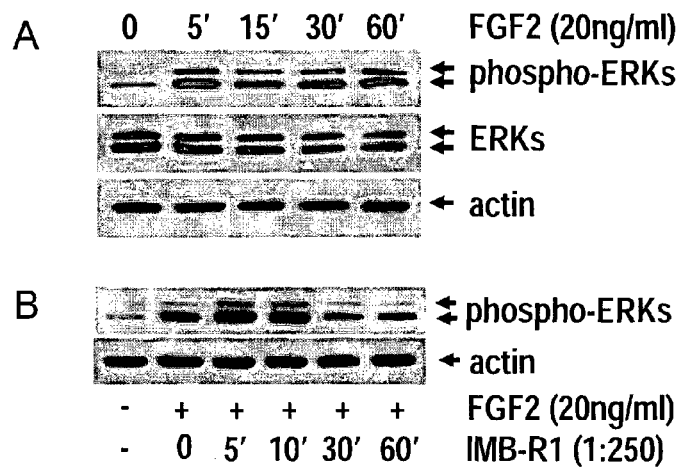
FIG. 12. (A) Western blot showing effect of FGF2 on ERK phosphorylation in MG63 cells. (B) Western blot showing effect of IMB-R1 on FGF2 induced phosphorylation of ERKs in MG63 cells.

FGF2 was able to induce an abundant increment of phosphorylated ERKs as early as 5 minutes and the level was well sustained until after 60 minutes (FIG. 12A).

We next examined the effect of IMB-R1 on FGF2 stimulated ERK activity. The cells were again deprived of serum for 2 days and stimulated with 20 ng/ml FGF2 for 5 minutes, or pretreated with IMB-R1 for various durations (5, 10, 30, or 60 minutes) before the FGF2 stimulation. The cells were then lysed and the protein samples were prepared for Western Blotting to detect the phosphorylation of ERKs.

Results

The pretreatment with IMB-R1 was able to inhibit FGF2 dependent ERK activation, if given long enough time (at least 30 minutes) to allow IMB-R1 to take effect (FIG. 12B).

Example 13

ERK Activity was Required for FGF Dependent MG63 Cell Growth

Our data had showed that IMB-R1 inhibited FGF2 stimulated ERK activity as well as cell growth and survival, suggesting ERK mediated FGF2 stimulated cell growth and survival. To verify this, we examined whether FGF2 stimulated MG63 cell growth could be affected by U0126, a MEK inhibitor (MEK is the upstream kinase that activates ERKs).

Cells were first treated with increasing doses of U0126 for 48 hours. The viable cell numbers were then analysed by GUAVA system. Next, cells were treated with 20 ng/ml FGF2 in the presence or absence of the optimal dose of U0126 determined from the first assay, before the cell counting was performed.

Figure 13A:
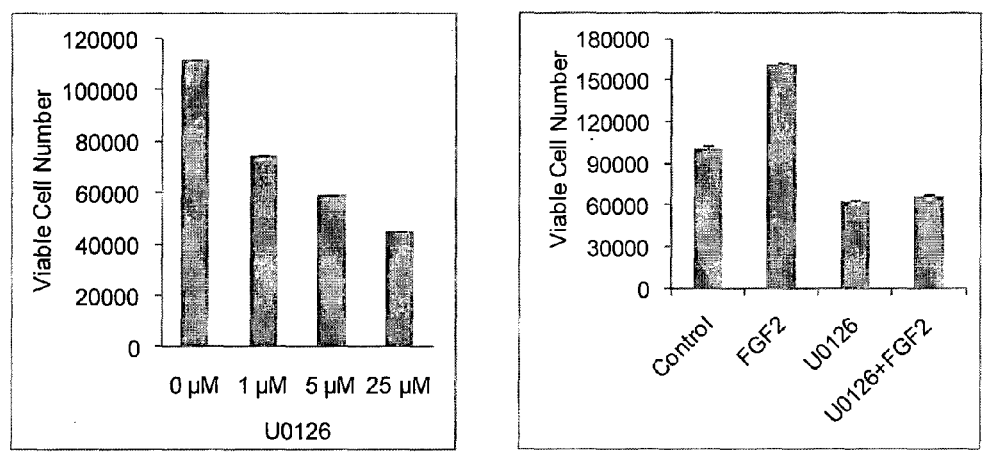
FIG. 13. (A) Graphs showing effect of U0126 on growth of MG63 cells and FGF2 stimulated MG63 cell growth. (B) Analysis of Annexin V-PI staining as an indicator of apoptosis in MG63 cells, in response to treatment with U0126.

U0126 dose-dependently inhibited MG63 cell growth and at 25 µM, it approximately reduced cell number to 50% of that of cells without U0126 treatment (FIG. 13A). 25 µM U0126 was sufficient to completely suppressed the FGF2 stimulated cell growth (FIG. 13A). Thus we concluded that ERK pathway was required for FGF2 stimulated MG63 proliferation.

Cells were treated with 25 µM U0126 for 24 hours before the apoptosis of the cells was analysed by Annexin-PI staining.

Figure 13B:
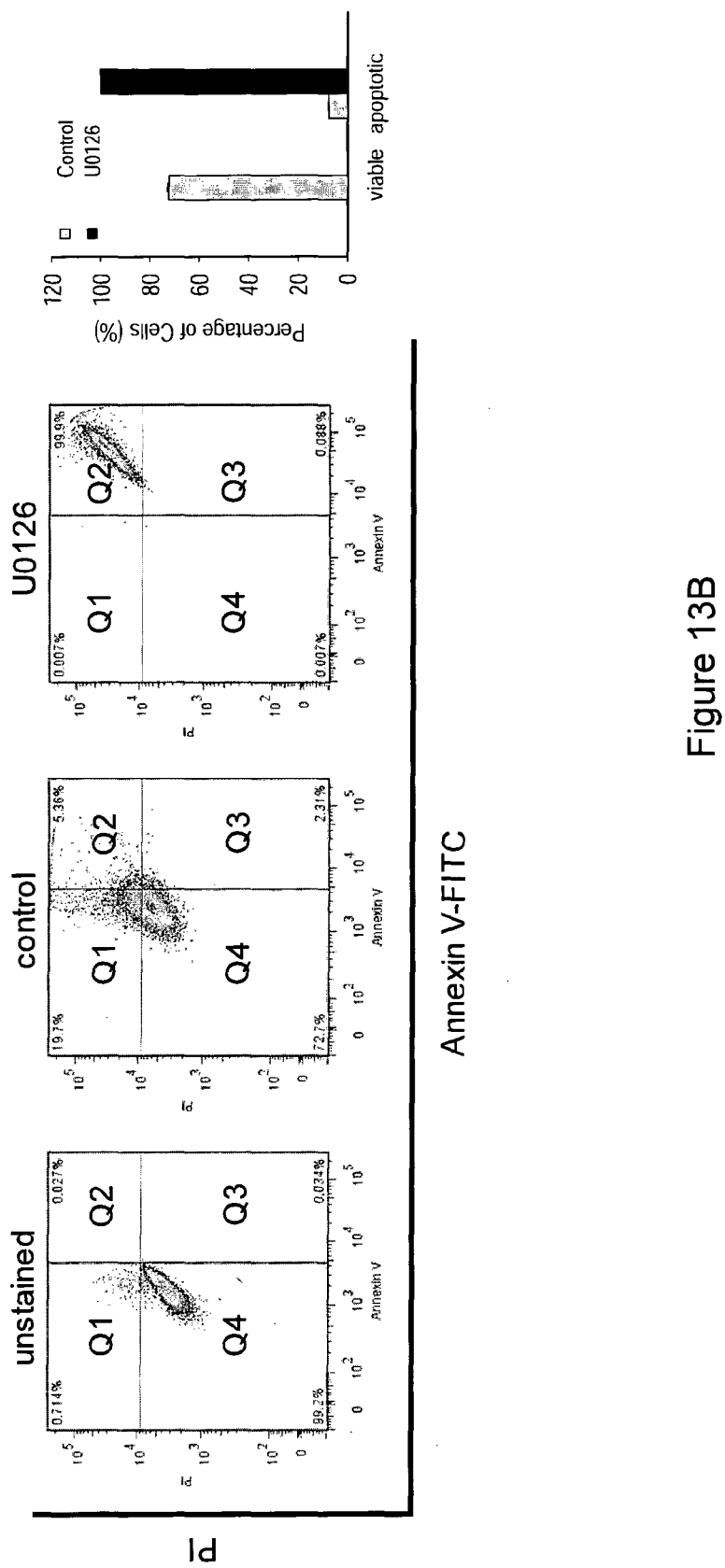

U0126 dramatically diminished viable cells (from 72.3% to less than 1%) while increased cell apoptosis (from 7.49% to nearly 100%) (FIG. 13B). Thus we concluded that ERK pathway was required for FGF2 stimulated MG63 growth and survival.

Example 14

Fibroblast growth factor receptor 1 (FGFR1) is found to be overexpressed and expressed abundantly in breast cancer and osteosarcoma cell lines. This provides a potential therapy for breast cancer and osteosarcoma via inhibition of FGFR1. A polyclonal antibody, IMBR1 has been raised against FGFR1. IMBR1 upon binding to FGFR1 inhibits Erk signaling pathway downstream of FGFR1. Treatment of cancer cell lines with IMBR1 result in decrease cell viability. However, the effect of IMBR1 on p54 is unknown. Thus, it is unclear whether observed decreased cell viability is due to necrosis or apoptosis. In this Example, the effect of IMBR1 on various tumour suppressor proteins and proteins involved in apoptotic pathway were investigated. Breast cancer and osteosarcoma cells treated with IMBR1 have increased protein level of p53, a key mediator of apoptosis. IMBR1 treatment also increases protein level of various tumour suppressors and pro-apoptotic protein. Thus, IMBR1 treatment leads to apoptosis which decreases cell viability. This suggest that FGFR1 signalling in breast cancer and osteosarcoma cell lines prevents activation of apoptotic pathway and is crucial for cell viability.

Introduction

Deregulated Fibroblast Growth Factor Receptor (FGFR) Signaling in Cancer

In cancer, several mechanisms cause excessive FGFR signalling resulting in malignant growth. The four main mechanisms are: (1) upregulated FGFR expression, (2) mutations or chromosomal rearrangements in FGFR encoding genes leading to FGFR with altered signaling activities, (3) increased expression of FGF and (4) damage to FGFR signaling pathway. Deregulated FGFR signaling leads to excessive activation of mitogenic, anti-apoptosis and angiogensesis signaling pathway which promotes malignant growth. (Haugsten et al., 2010) However, there is no current drug in the market which targets FGFR1 specifically (Turner and Grose, 2010).

FGFR Structure

Figure 16:
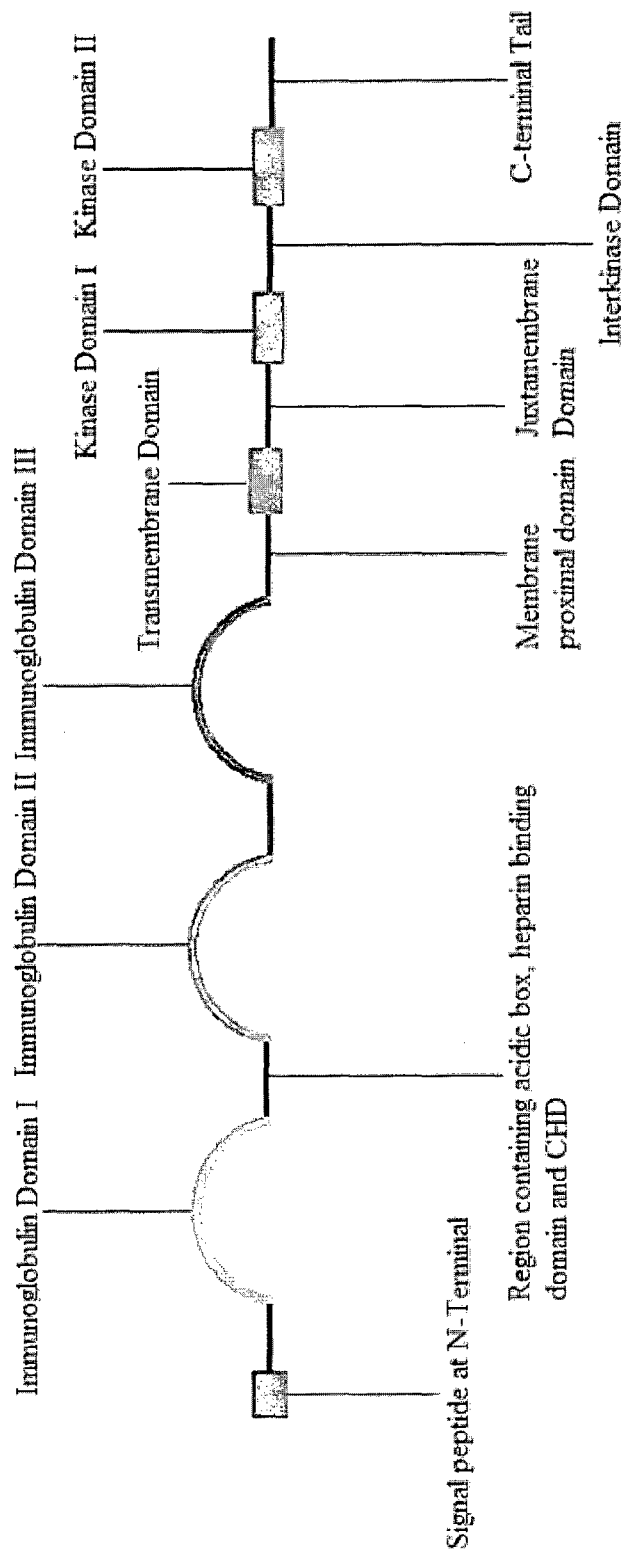
FIG. 16. Diagram illustrating general structure of FGFR. (Adapted from Groth and Lardelli, 2002)

FGFRs are encoded by five distinct genes resulting in five families of FGFR termed FGFR1-5. FGFR1-4 shared 55% to 72% homology in amino acid sequence while FGFR5 is the most distantly related member with approximately 30% in amino acid homology (Johnson and Williams, 1993; Kim et al., 2001; Sleeman et al., 2001). FGFR1-4 consists of an extracellular region, transmembrane domain and intracellular region. The extracellular region consists of an N-terminal signal peptide and three immunoglobulin-like (Ig) domains (Johnson and Willianms, 1993). The acidic box domain consists of eight acidic amino acid residues, a heparin-binding region and cell adhesion molecule homology domain located between IgII and IgIII (Kan et al., 1991; Doherty and Walsh, 1996). (FIG. 16).

Alternative splicing of mRNA results in a isoform containing all three Ig domains or β isoform which contains only IgII and IgIII. FGFR1 and FGFR2 exist in both isoforms while FGFR3 and FGFR4 exist only in a isoform. Alternative splicing at C-terminal end of IgIII in FGFR1-3 generates receptors with IgIIIb or IgIIIc domains and determine ligand binding specificity. In addition, an IgIIIa isoform of FGFR1, which is secreted can also be generated (Johnson, 1990; Johnson and Williams, 1993).

FGFR Signaling Pathway

FGFR signaling regulates crucial cellular process such as proliferation, survival and differentiation (Turner and Grose, 2010). Eighteen functionally defined fibroblast growth factors (FGF) can bind FGFR and heparin sulfate proteoglycans (HSPG). Upon ligand binding, a 2:2:2 FGF-FGFR-HSPG ternary complex on the cell surface is formed (Schlessinger et al., 2000). This complex stabilizes receptor dimerization and promote FGFR trans-phosphorylation which occurs in three discrete stages. Firstly, tyrosine (Y) residue Y653 in the kinase domain activation loop is phosphorylated leading to 50 to 100 fold increase of kinase activity. Secondly, Y583, Y463 Y766 and Y585 are phosphorylated to provide docking sides for recruitment of proteins containing Src homology 2 (SH2) and phosphotyrosine-binding domain (PTB). Lastly, another kinase domain activation loop residue Y654 is phosphorylated leading to another 500 to 1000 fold increase in kinase activity and subsequent phosphorylation of FGFR substrate (Furdui et al., 2006).

Phosphorylation of tyrosine residues lead to activation of several downstream intracellular signaling pathways. Fibroblast growth factor receptor substrate 2 (FRS2) is recruited to phosphorylated Y766 via SH2 domain-containing adapter protein B (Shb) (Cross et al., 2002). FRS2 is then phosphorylated which leads to recruitment of growth factor receptor-bound protein 2 (GRB2) which in turn recruits both son of sevenless homolog 1 (SOS1) and GRB2-associated-binding protein 1 (GAB1) (Ong et al., 2001). GAB1 activates phosphoinositide-3 kinase (PI3K) via binding to regulatory subunit. This activates AKT-dependent anti-apoptotic pathway (Altomare and Testa, 2005) SOS1 activates RAS GTPases which in turn activates effector protein. These effector proteins in turn activate downstream signaling pathways. (Rhee, 2001; Downward, 2003). These downstream pathways in turn promote cell cycle progression and cell survival. This is achieved by antagonizing activities of pro-apoptotic proteins Bcl-2-like protein 11 (BIM) and Bcl-2-associated death promoter (BAD) and prevent expression of BIM by phosphorylating transcription factor forkhead box O3a (FOXO3a) leading to nuclear exclusion (Datta et al., 1997; Ley et al., 2003). Both pathways also promote expression of pro-survival proteins B-cell lymphoma-extra large (BCL-XL) (Balmanno and Cook, 2009).

Phosphorylation of Y766 also leads to recruitment and phosphorylation of phospholipase C (Landgren et al., 1998). This results in hydrolysis of phosphatidylinositol-4,5-bisphonate which generate two second messengers, diacyglycerol and inositol (1,4,5)-triphosphate (Ins (1,4,5) P3). Ins (1,4,5)

P3 binds to Ins (1,4,5) P3 receptors which are Ca2+ channels on endoplasmic reticulum. This releases Ca2+ from endoplasmic reticulum into the cytosol. Released Ca2+ promotes activation of Ca2+ dependent protein kinases such as protein kinase C for further downstream signaling (Rhee, 2001).

A polyclonal antibody, IMBR1 which binds to FGFR1 was developed. Based on previous work by Ling et al. (unpublished results), IMBR1 exert effect on FGFR1 signaling pathway by inhibiting FGF2 stimulated FGFR1 activation Erk signaling pathway. In this Example, the effects of IMBR1 on cell viability and the signaling mechanisms involved were investigated.

Materials and Methods
Cell Culture

MCF-10A, a human mammary epithelial cell line was maintained in Dulbecco's Modified Eagle's medium with glucose concentration of 4500 mg/L (DMEM; Invitrogen, USA) supplemented with 5% horse serum (Invitrogen, USA), 20 ng/ml epidermal growth factor (Peprotech, USA), 0.5 mg/ml hydrocortisone (Sigma™, USA), 100 ng/ml cholera toxin (Sigma, USA), 10 μg/ml insulin (Sigma, USA) and 1% Penicillin/Streptomycin mix (Invitrogen, USA).

T47D, a human ductal breast epithelial cell line was maintained in Roswell Park Memorial Institute 1640 (RPMI-1640; Invitrogen, USA) medium supplemented with 10% fetal calf serum (FCS; Thermo Fisher Scientific, USA) and 1% Penicillin/Streptomycin mix (Invitrogen, USA).

MDA-MB-468, a human mammary adenocarcinoma cell line was maintained in DMEM with glucose concentration of 4500 mg/L (Invitrogen, USA) and supplemented with 10% FCS (Thermo Fisher Scientific, USA), 2 mM L-glutamine (Invitrogen, USA) and 1% Penicillin/Streptomycin mix (Invitrogen, USA).

OS-1, a human primary osteosarcoma cell line was a gift from Dr Suresh Nathan, National University Singapore (Nathan et al., 2009) and maintained in DMEM with glucose concentration of 1000 mg/L (Invitrogen, USA) supplemented with 10% FCS (Thermo Fisher Scientific, USA), 15 mM HEPES (BSF, Singapore) and 1% Penicillin/Streptomycin mix (Invitrogen, USA).

Saos-2, a human epithelial-like osteosarcoma cell line was maintained in McCoy's 5a Modified Media (Sigma, USA) supplemented with 15% FCS (Thermo Fisher Scientific, USA) and 1% Penicillin/Streptomycin mix (Invitrogen, USA).

hOS, a human osteosarcoma cell line was maintained in Minimal Essential Media 10370 (Invitrogen, USA) supplemented with 10% FCS (Thermo Fisher Scientific, USA)), 2 mM L-glutamine (Invitrogen, USA) and 1% Penicillin/Streptomycin mix (Invitrogen, USA).

All cell lines except OS-1 were obtained from American Type Culture Collection and kept at 5% CO2 at permissive temperature of 37° C.

Cell Treatment

Old media was first removed and 3 ml of fresh media added. IMBR1 and rabbit IgG were added to achieve desired dosage. PD166866 (Sigma-Aldrich, USA) and SU5402 (Merck, Germany) were dissolved in dimethyl sulfoxide (DMSO; Sigma-Aldrich, USA) and added to master mix of media to achieve desired concentration. Additional DMSO was added such that total volume of chemicals added was constant.

Western Blot

Cells were grown in 6 cm dish with 3 ml of media at a seeding density of 20,000 cells/cm$^2$, except for MDA-MB-468 which was seeded at a density of 100,000 cells/cm$^2$. Cells were lysed with laemmli buffer (Sigma-Aldrich, USA) and transferred to pre-chilled tubes. Cells were kept on ice throughout extraction process.

Protein was denatured at 95° C. for 5 minutes and separated out by molecular weight on NuPage Novex 4-12% Bis-Tris Mini Gels (Invitrogen, USA) at 180V for 1 hour.

Protein was blotted onto nitrocellulose membrane (Bio-Rad, USA). Primary antibodies used were: p53 (Santa Cruz, USA), p21 (BD Pharmingen, USA), retinoblastoma protein (Rb), phosphorylated Rb (pRb), c-Myc, phosphorylated p53 (Ser15) (Phospho-p53), Bcl-XL, phosphorylated Forkhead box O3a (phospho-FoxO3a) (Ser318/321) and Bcl-2-like protein 11 (Bim). All primary antibodies were purchased from Cell Signaling, USA unless otherwise stated.

Prior to this, membrane was blocked at room temperature in 5% bovine serum albumin (BSA; Bio-Rad, USA) or 5% milk in Tris (Invitrogen, USA) buffer [Sodium chloride (Sigma, USA), Tween-20 (Bio-Rad, USA)] at 4° C. Nitrocellulose membrane strip corresponding to actin region was blocked overnight and incubated for 1 hour with anti-actin primary antibodies at room temperature (Chemicon, USA). Goat-anti-mouse (Jackson Immunoresearch, USA) and goat-anti-rabbit (Jackson Immunoresearch, USA) horseradish peroxidase (HRP) conjugated secondary antibodies were used to detect primary antibodies. Protein bands were visualized with LumiGLO Chemiluminescent Substrate system (KPL, USA) and LumiGLO Reserve Chemiluminescent Substrate kit (KPL, USA). Bands were normalized to housekeeping protein actin. Densitometry was performed using QuantityOne software (Bio-Rad, USA).

Quantitative Real Time Polymerase Chain Reaction (qRT-PCR)

Cells were grown in 6-well plate with 3 ml of media at a seeding density of 20,000 cells/cm$^2$, except for MDA-MB-468 which were seeded at a density of 100,000 cells/cm$^2$. RNA was extract and purified using NucleoSpin RNA II kit (Macherey-Nagel, Germany) as per manufacturer's instructions. Complementary cDNA were synthesized from RNA using SuperScript VILO cDNA Synthesis Kit (Invitrogen, USA) as per manufacturer's instructions. qRT-PCR was performed on ABI 7500 Fast Real Time PCR machine using TaqMan Fast Universal PCR Master Mix (Applied Biosystems, Carlsbad, Calif., USA). The following probes purchased from ABI, USA were used to measure mRNA relative expression level: FGFR1, FGFR2, FGFR3, FGFR4 and Glyceraldehyde 3-phosphate dehydrogenase (GAPDH). Samples were heated to 95° C. for 2 minutes, and 45 cycles of heating at 95° C. for 3 seconds, 60° C. for 30 seconds. Triplicates were performed and mRNA expression levels were normalized to GAPDH mRNA levels. Relative expression units (REU) were calculated with the following formula:

$$\tfrac{1}{2}^x.$$

Quantification of Viable Cells Via GUAVA

Cells were grown in 24-well plate with 500 μl of media at a seeding density of 20,000 cells/cm$^2$, except for MDA-MB-468 which were seeded at a density of 100,000 cells/cm$^2$. Each well of cells were then collected via trypsinization with 200 μl of trypsin-EDTA (Invitrogen, USA) and neutralized with 200 μl of media. 1 μl of GUAVA Viacount Flex dye (Guava Technologies, USA) was added to each well. Quantification of viable cells were performed as per manufacturer's instructions.

Enzyme-Linked Immunosorbent Assay (ELISA)

Enzyme Immuno-assay plate (Nalgene-Nunc, USA) was coated overnight at 4° C. with 0.5 μg/ml of goat anti-human IgG-Fc (Jackson Immunoresearch, USA). Plate was blocked with 5% BSA (Bio-Rad, USA) in Dulbecco's Phosphate Buffered Saline (DPBS; BSF, Singapore) and then incubated with 100 ng/ml of FGFR1b, FGFR1c, FGFR2c and FGFR3c. Plate was then incubated with IMBR1 or rabbit IgG as control at various dilutions. Triplicates were performed for each dilution. Goat-anti-rabbit HRP conjugated antibodies (Jackson Immunoresearch, USA) were then used to detect binding of IMBR1 and rabbit IgG to FGFR. Plate was developed with TMB Substrate Kit (Thermo Fisher Scientific, USA) and absorbance measured by Wallac Victor microplate reader (Perkinelmer, USA) at 450 nm. Plates were washed in between incubation by 0.05% Tween-20 (Bio-Rad, USA) in DPBS (BSF, Singapore).

Results

FGFR Expression in Breast Cancer and Osteosarcoma Cell Lines

To determine the mRNA REU of FGFR1, FGFR2, FGFR3 and FGFR4, qRT-PCR was performed. The cell lines used are human mammary epithelial cell line MCF-10A which functions as a control, breast cancer cell lines T47D, MCF-7, MDA-MB-231, MDA-MB-468 and osteosarcoma OS-1. Housekeeping gene GAPDH was used for normalization.

Figure 17A:
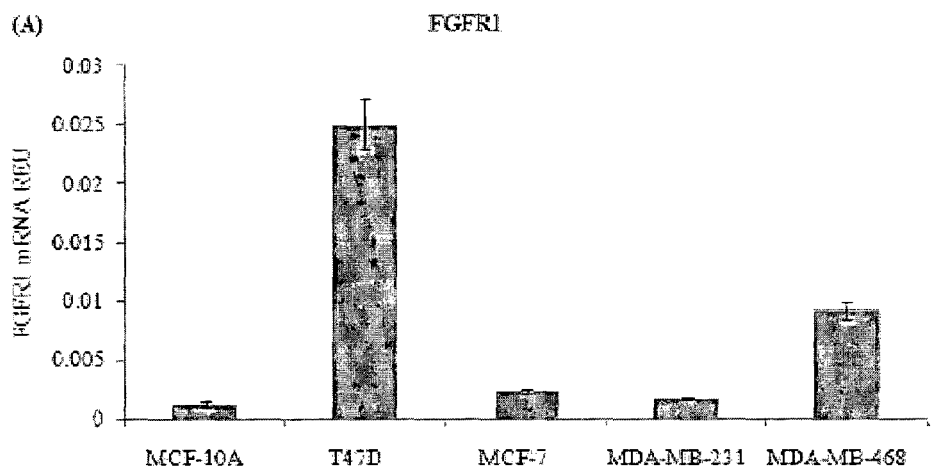
FIG. 17. Graphs showing mRNA level of FGFR in breast cancer and osteosarcoma cell lines. A. mRNA level of FGFR1, B. mRNA level of FGFR2, C. mRNA level of FGFR3, D. mRNA level of FGFR4 in human mammary epithelial cell MCF-10A., breast cancer cells T47D, MCF-7, MDA-MB-231, MDA-MB-468. E. Comparison of FGFR1, FGFR2, FGFR3 and FGFR4 mRNA level in MCF-10A and breast cancer cell lines. F. mRNA level of FGFR1, FGFR2, FGFR3 and FGFR4 in osteosarcoma cell line OS-1.
Figure 17B:
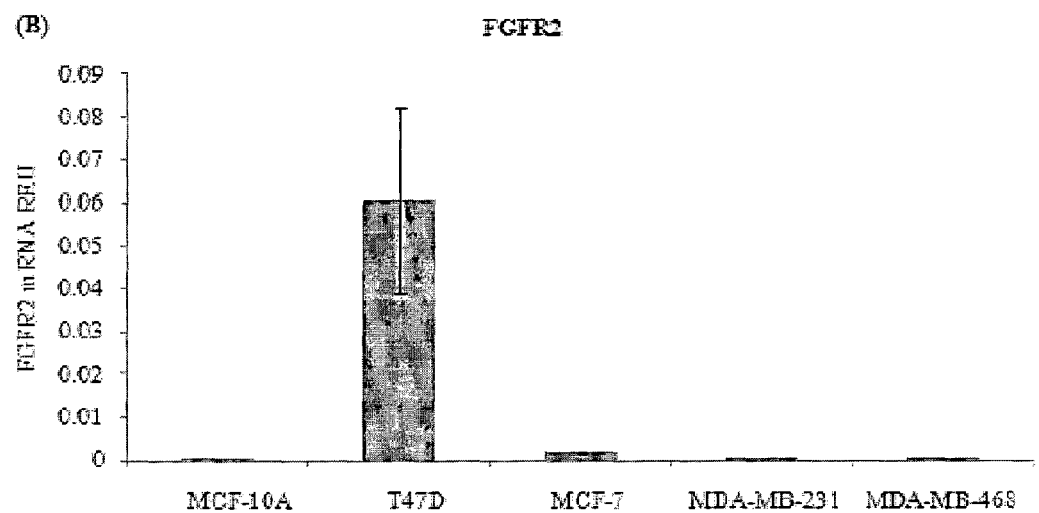
Figure 17C:
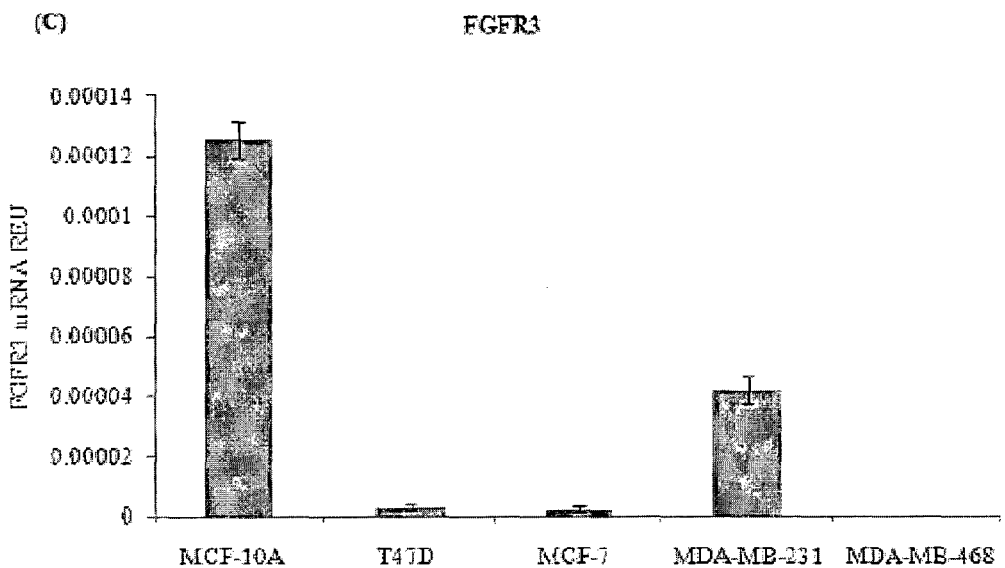
Figure 17D:
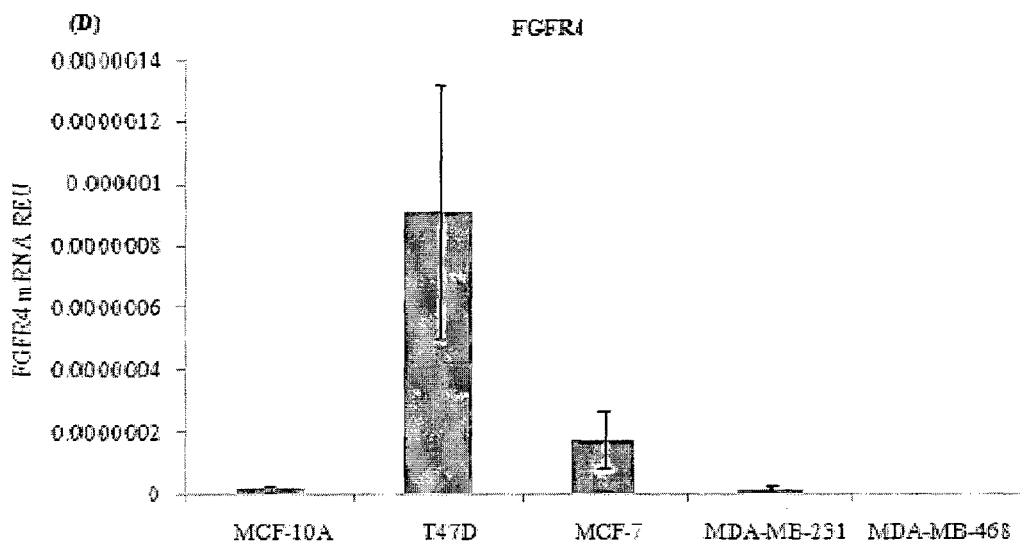

Among the four FGFRs, only FGFR1 was overexpressed in all breast cancer cell lines. FGFR1 mRNA level was higher in all breast cancer cell lines compared to MCF-10A (FIG. 17A). This suggested an increased level of FGFR1 mRNA in breast cancer cell lines. In contrast, FGFR2 was only overexpressed in T47D and MCF-7 (FIG. 17B), FGFR3 was not overexpressed in breast cancer cell lines (FIG. 17C) and FGFR4 was only overexpressed in T47D and MCF-7 (FIG. 17D). Thus, only FGFR1 was overexpressed in all breast cancer cell lines.

Figure 17E:
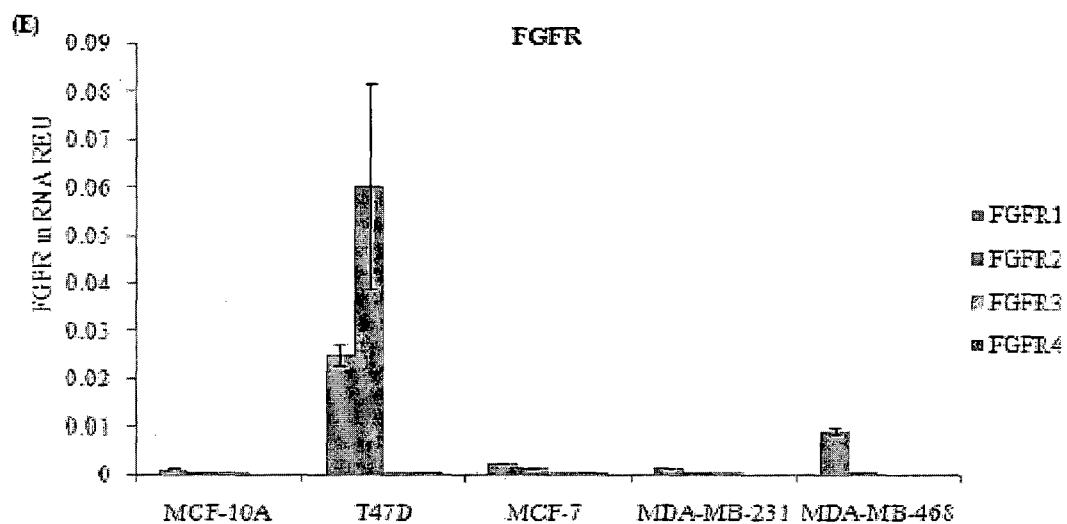

Within a cell, only FGFR1 was expressed in abundance in all breast cancer cell lines except for T47D. FGFR1 mRNA REU was higher than FGFR2, FGFR3, FGFR4 mRNA REU in MCF-7, MDA-MB-231 and MDA-MB-468 (FIG. 17E). Thus, only FGFR1 was expressed in abundance across breast cancer cell lines.

Figure 17F:
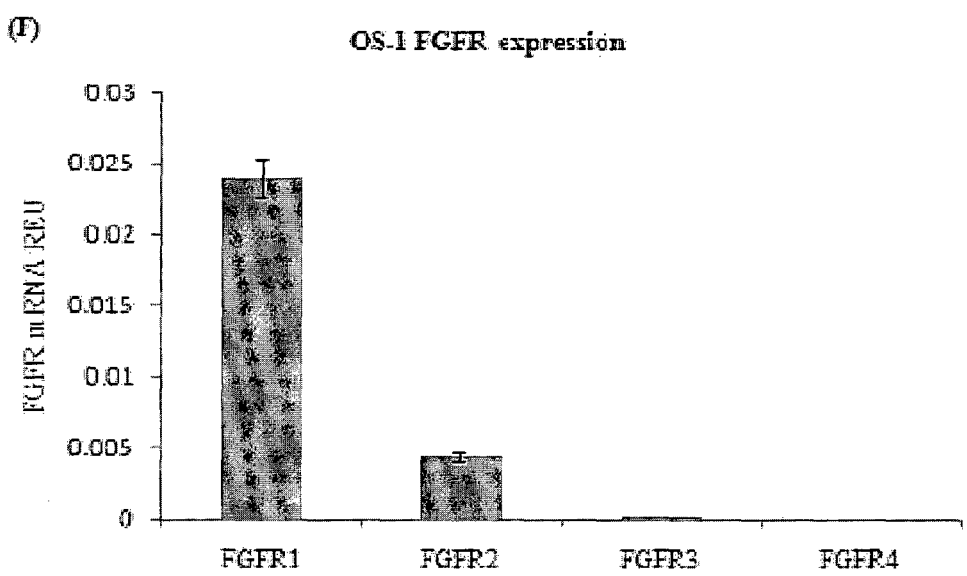

In OS-1, FGFR1 was expressed in abundance. FGFR1 mRNA REU was 0.024 while FGFR2 mRNA REU was 0.004, FGFR3 and FGFR4 mRNA REU were negligible (FIG. 17F). Thus only FGFR1 was expressed in abundance in primary osteosarcoma cell line OS-1.

Effect of PD166666 and SU5402 on Osteosarcoma Cell Viability

To determine the effect of inhibiting FGFR1 signaling on cell viability in osteosarcoma cells, Saos-2 and hOS were treated with varying concentrations of FGFR tyrosine kinase inhibitors PD166866 (Panek et al., 1998) and SU5402 (Mohammadi et al, 1997). The control groups of respective cell lines were treated with equivalent volume of DMSO, as DMSO is the vehicle for both chemical inhibitors. Cell viability was measured via GUAVA and fold change calculated to compare changes in number of cells after two day treatment and number of cells plated. A fold change greater than one indicated an increase in number of cells while a fold change less than one indicated a decrease in number of cells compared to number of cells plated.

Figure 18A:
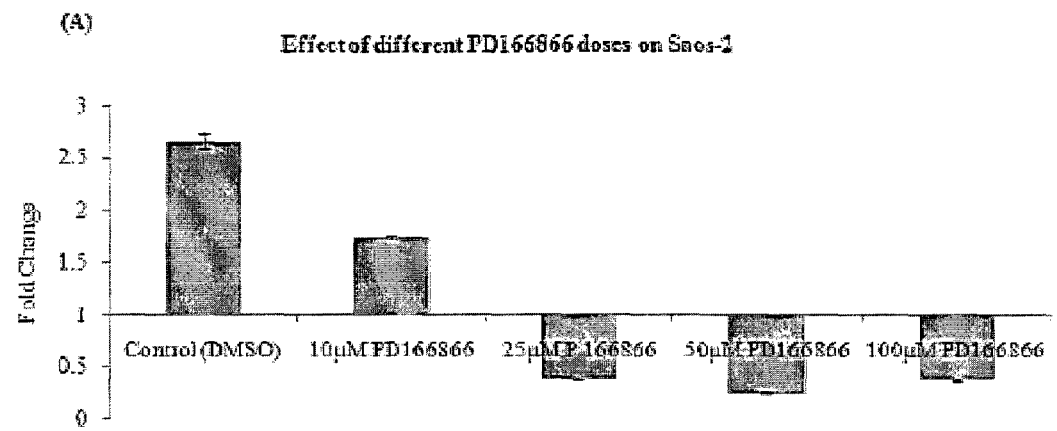
FIG. 18. Graphs showing Effect of PD166866 and SU5402 on cell growth in osteosarcoma. A. Effect of PD166866 on Saos-2. B. Effect of SU5402 on Saos-2. C. Effect of PD 166866 on hOS. D. Effect of SU 5402 on hOS.
Figure 18B:
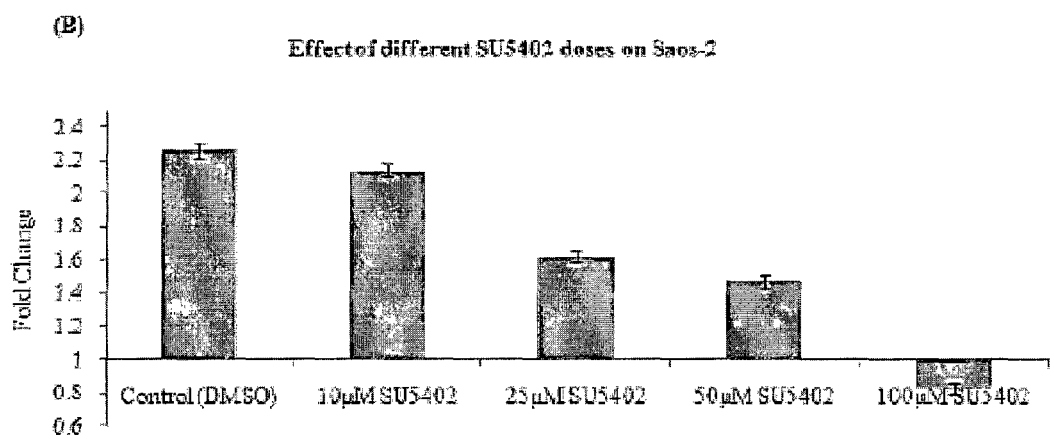
Figure 18C:
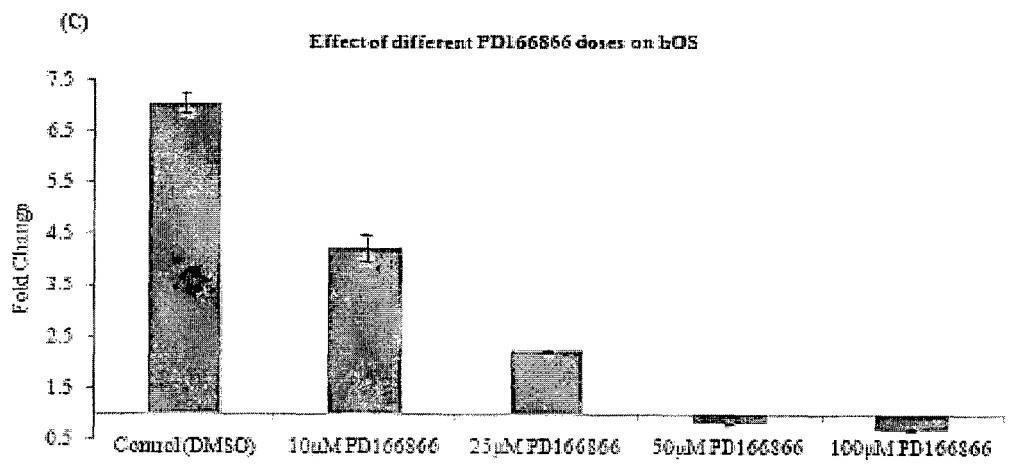

In Saos-2 and hOS, two day treatment with PD166866 resulted in a decrease in number of cells in a dose dependent manner. In Saos-2, fold change of control group was 2.6 while for PD166866 treatment, fold change ranged from 1.7 for 10 μM of PD166866 to 0.4 for 100 μM of PD166866 (FIG. 18A). In hOS, fold change of control group was 7.0 while for PD166866 treatment, fold change ranged from 4.2 for 10 μM of PD166866 to 0.7 for 100 μM of PD166866 (FIG. 18C).

Thus, compared to control, number of viable Saos-2 and hOS cells decreased upon FGFR signaling inhibition by PD166866.

Figure 18D:
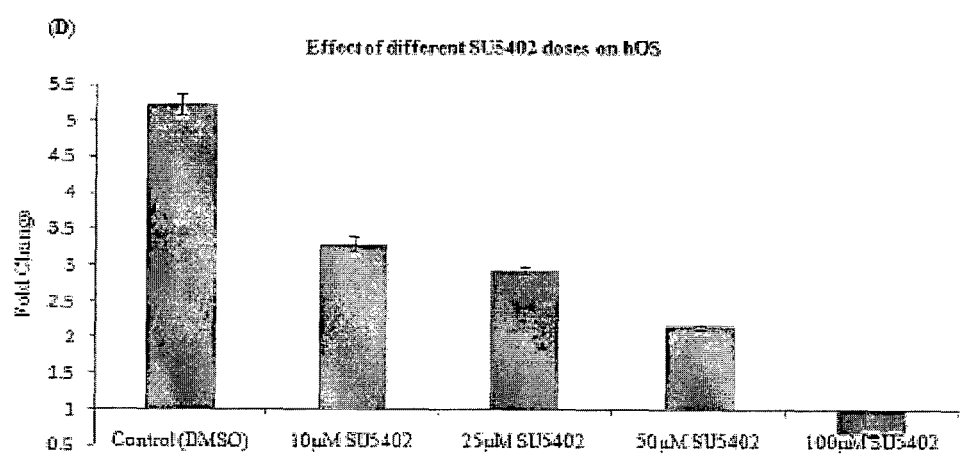

Two day treatment with SU5402 in Saos-2 and hOS also resulted in a decrease in number of viable cells in a dose dependent manner. In Saos-2, fold change of control group was 2.3 while for SU5402 treatment, fold change ranged from 2.14 for 10 μM of SU5402 to 0.9 for 100 μM of SU5402 (FIG. 18B). In hOS, fold change of control group was 2.3 while for SU5402 treatment, fold change ranged from 5.2 for 10 μM of SU5402 to 0.6 for 100 μM of SU5402 (FIG. 18D). Thus, compared to control treated, number of viable Saos-2 and hOS cells decreased upon FGFR signaling inhibition by SU5402. Taken together, this suggested that inhibition of FGFR signaling affect osteosarcoma cell viability.

Binding Specificity of IMBR1

To determine the binding affinity and specificity of IMBR1, sandwich ELISA was performed. Absorbance level corresponds to binding level of IMBR1. An increased in IMBR1 binding would enable more goat-anti-rabbit HRP conjugated antibody to be bound. This would produced an increase in absorbance level with addition of developing agent. Data obtained was combined with data obtained by Ling et al. (unpublished results).

FGFR1, 2 and 3 have splice variants "b" and "c". First, the ELISA plates were coated with goat anti-human IgG-Fc (Jackson ImmunoResearch Labs), followed by blocking with 2% BSA. The plates were next incubated with 100 ng/ml FGFRs isoforms conjugated with Fc fragment or control human IgG, and then incubated with various concentrations of IMB-R1 or normal rabbit IgG as the control. Thereafter, the bound antibodies were detected with HRP conjugated goat anti-rabbit IgG (Jackson ImmunoResearch Labs) and visualized by TMB substrate. The developed color was measured using Victor3 multiplate reader at wavelength 450 nm. The raw data were normalized by the readings of the control wells. The higher the reading indicated higher affinity of IMB-R1 to the FGFRs.

Figure 19:
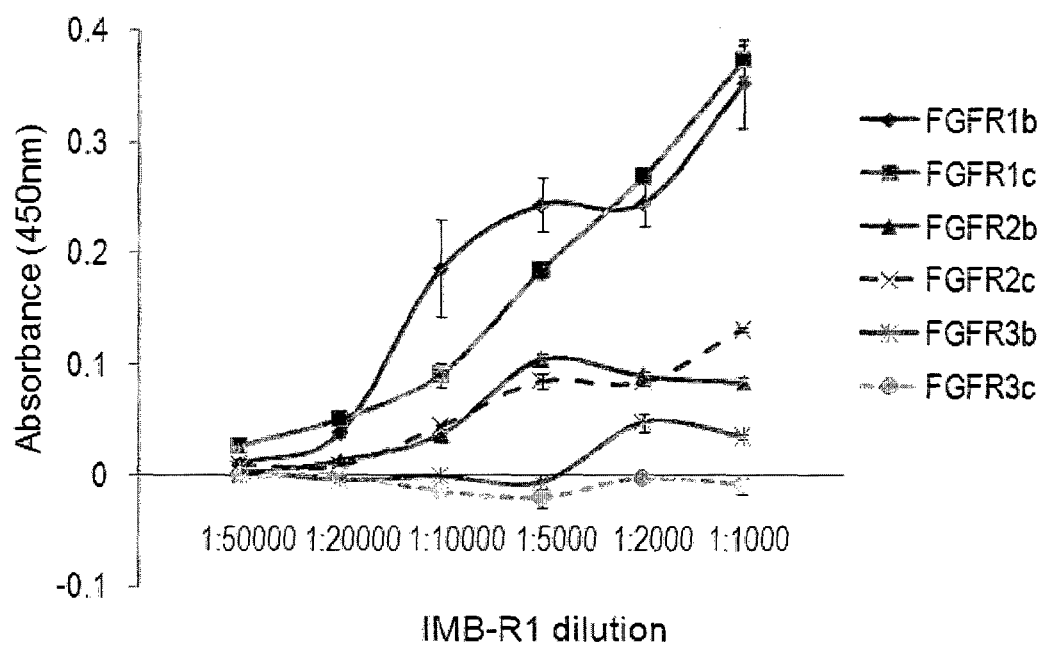
FIG. 19. Graph showing binding specificity of IMBR1. IMBR1 binds to FGFR1b and FGFR1c in a dose dependent manner.

Results suggested that IMBR1 binds to FGFR1b and FGFR1c with higher affinity then FGFR2c and FGFR3c. When FGFR1b and FGFR1c was used, absorbance ranged from 0.01 to 0.35 and 0.03 to 0.37 respectively. In contrast, when FGFR2c and FGFR was used, absorbance was below 0.100 except for FGFR2c with IMBR1 1:1000 dilution which had an absorbance of 0.14. (FIG. 19).

Results also suggested that IMBR1 binds specifically to FGFR1b and FGFR1c. Absorbance increase with decrease in IMBR1 dilution. For FGFR1b, absorbance increase from 0.01 to 0.35 when IMBR1 dilution was decrease within a range of 1:50000 to 1:1000. Similarly, with FGFR1c, absorbance increase from 0.03 to 0.37 when IMBR1 dilution was decrease within a range of 1:50000 to 1:1000. (FIG. 19).

The affinity of IMB-R1 to FGFR1b or FGFR1c was dose-dependently increased and the absorbance at 450 nm reached approximately 0.36 in the case of FGFR1 isoforms at 1:1000 dilution. However, the affinity of IMB-R1 to FGFR2 (absorbance is about 0.11) or FGFR3 (absorbance is ≤0.05) fluctuated around the low level. The affinity of IMB-R1 to FGFRs is at the ratio of: FGFR1:FGFR2:FGFR3=29:8:1. Clearly, IMB-R1 showed a significantly higher affinity to FGFR1 than to the other two FGFRs.

Effect of IMBR1 on Saos-2 Cell Viability

To determine the effect of IMBR1 on cell viability, GUAVA was performed after two day treatment with varying amount of IMBR1 or rabbit IgG as control. Rabbit IgG was used as control as IMBR1 is raised in rabbit. Half maximal inhibitory constant (IC50) was then determined.

Figure 20:
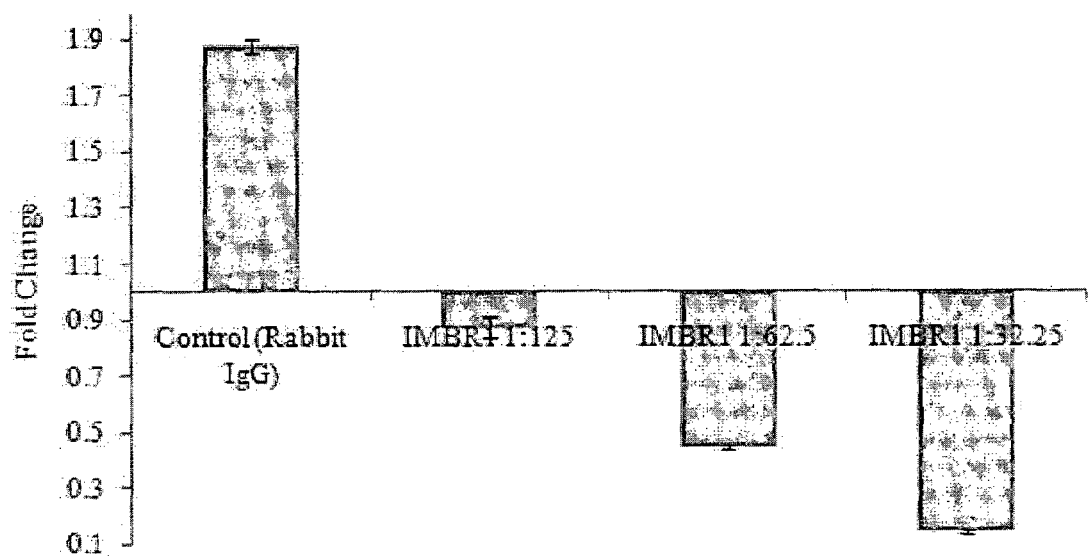
FIG. 20. Graph showing Effect of IMBR1 on Saos-2 cell growth.
Figure 21A:
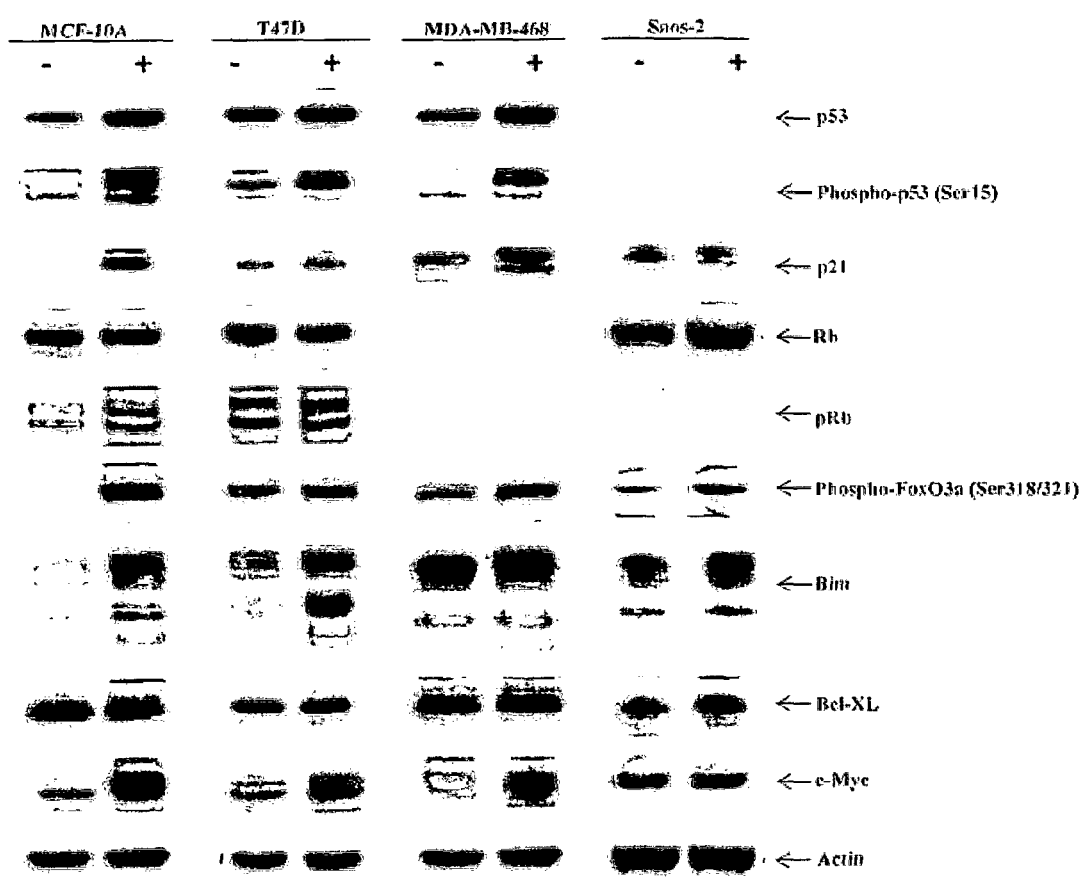
FIG. 21. Effect of IMBR1 on tumour suppressor protein and apoptotic regulators. A. Western blot of control (−) and IMBR1 treated (+) non-cancer cell lines, breast cancer cell lines and osteosarcoma cell lines. B. Graphs showing Densitometry readings of Western blots.
Figure 21B:
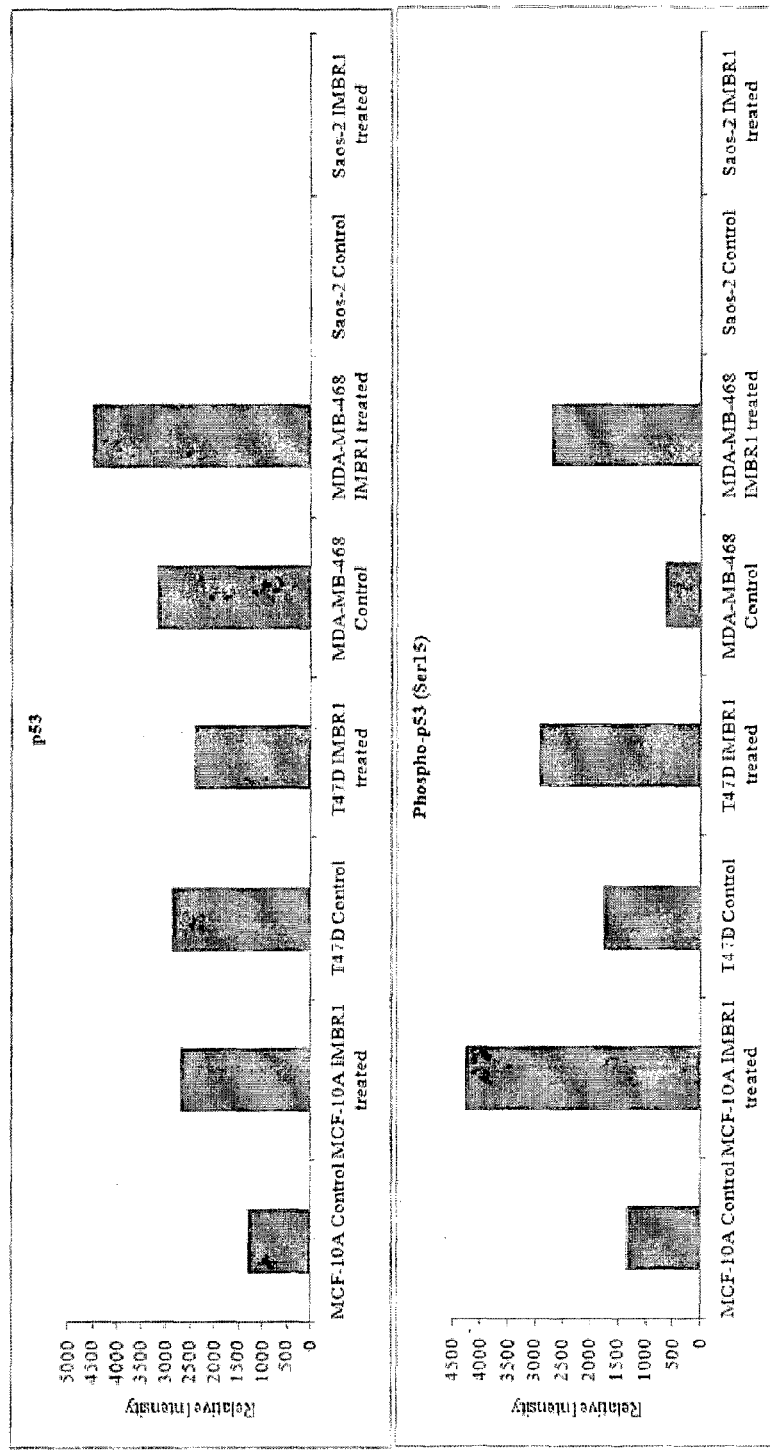
Figure 21B:
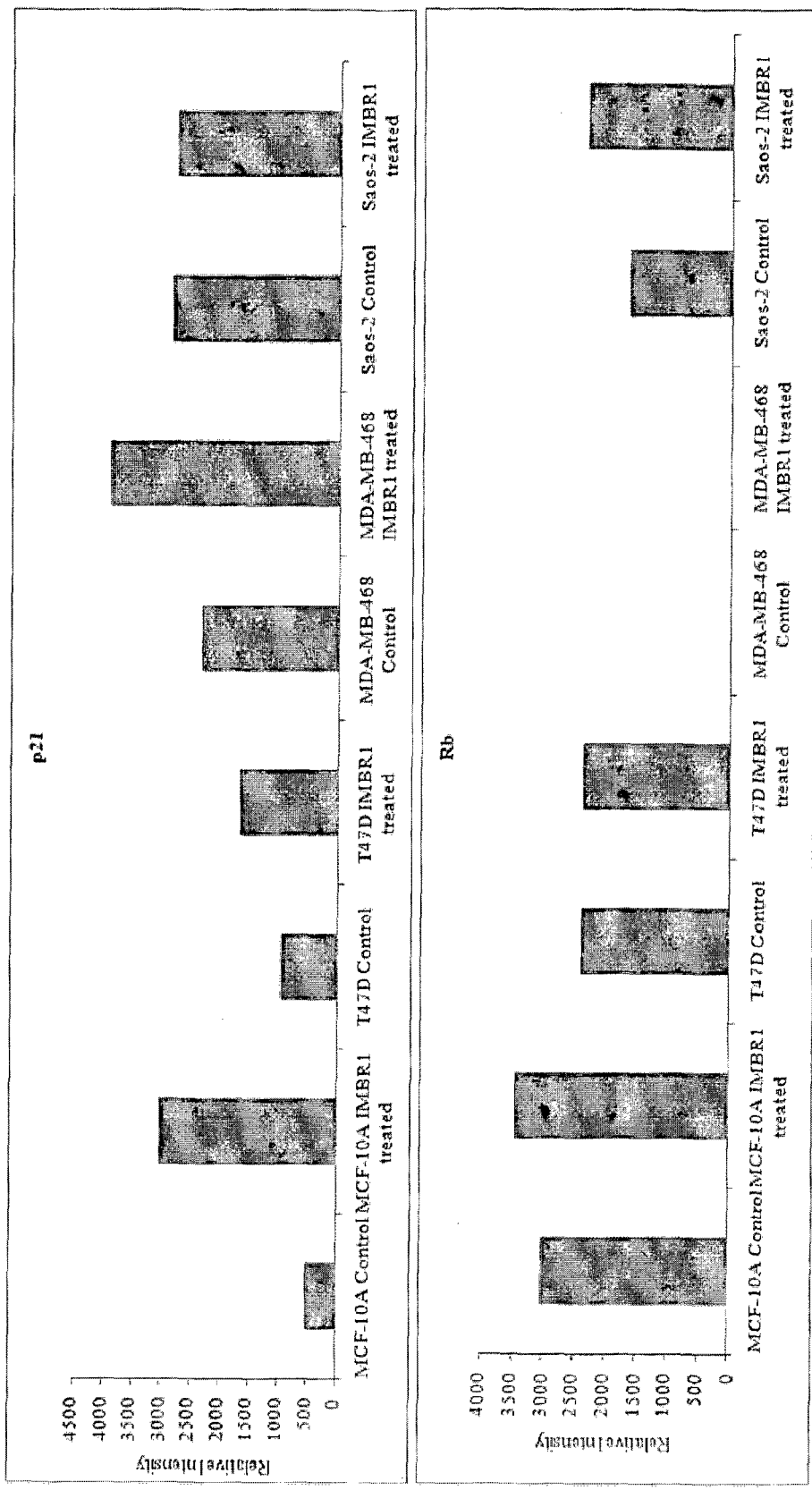
Figure 21B:
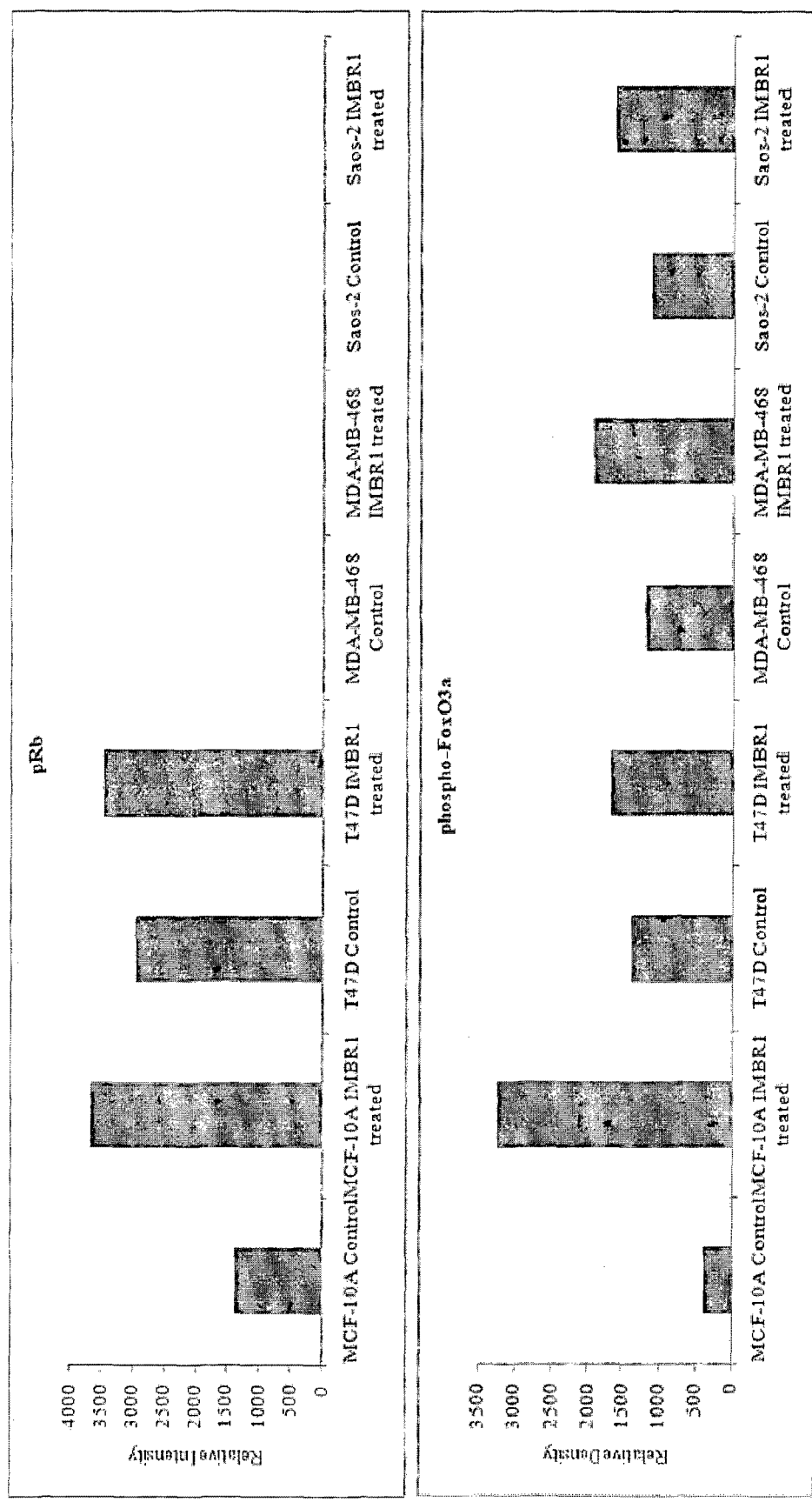
Figure 21B:
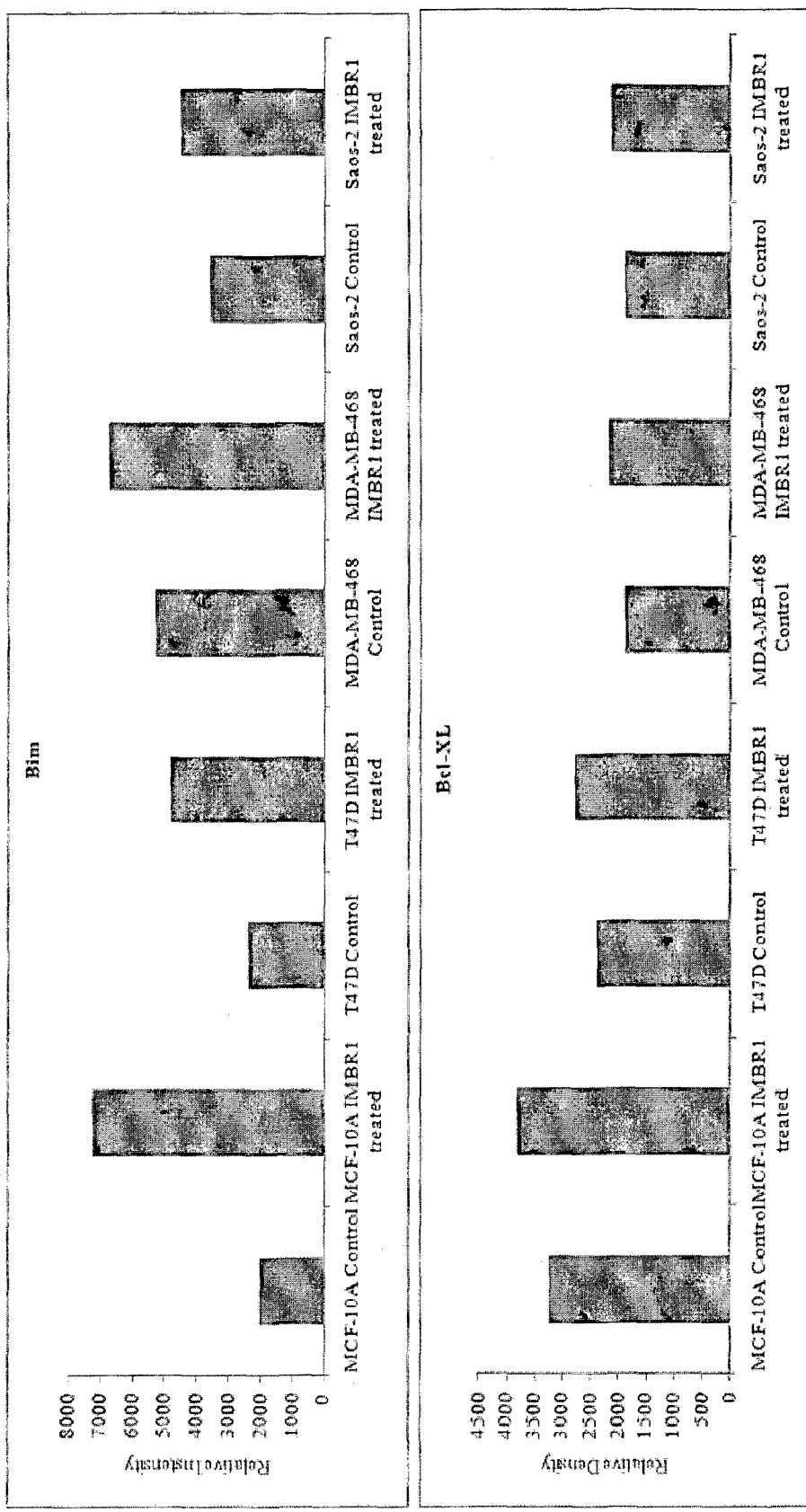
Figure 21B:
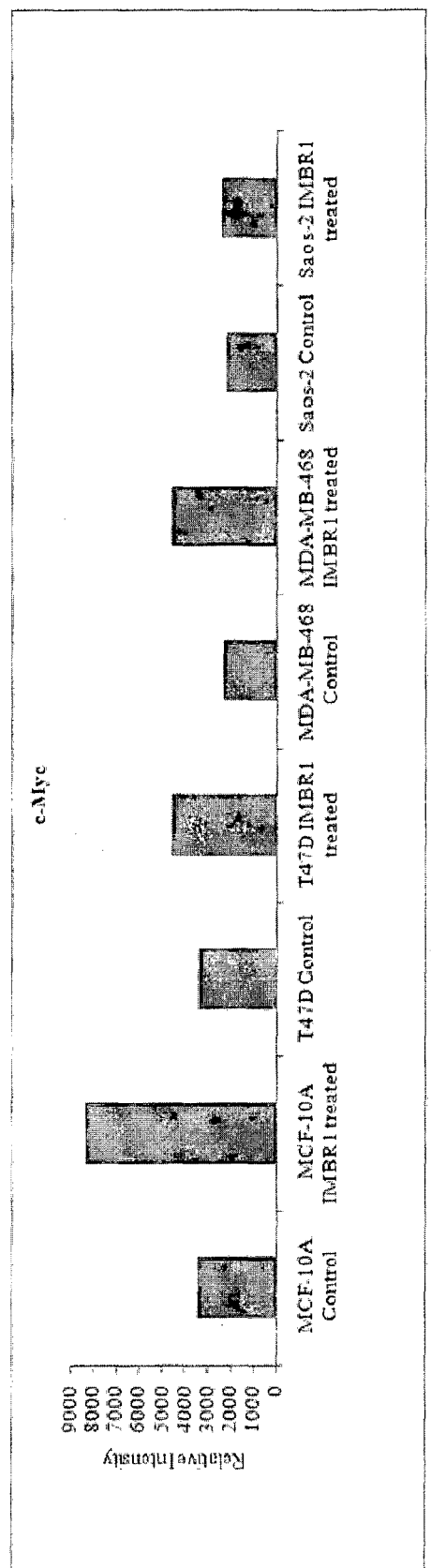

In Saos-2, IMBR1 treatment resulted in a decrease in number of cells in a dose dependent manner. Fold change upon control treatment was 1.8 and decreased in tandem with increasing amount of IMBR1 treatment used to 0.14 with IMBR1 dilution of 1:32.25 (FIG. 20). This suggested that IMBR1 decrease cell viability in a dose dependent manner.

IC50 for Saos-2 was determined to be 1:125 dilution of IMBR1 and used for subsequent experiments. $IC_{50}$ for other cell lines used were determined previously by Ling et al. (unpublished results).

Effect of IMBR1 on Tumour Suppressors and Proteins Involved in Apoptotic Pathway To determine whether necrosis or apoptosis was induced by IMBR1 treatment, Western blot was performed after two day treatment of IMBR1 at $IC_{50}$ or rabbit IgG as control. Rabbit IgG was used as control as IMBR1 was raised in rabbit. Protein levels of various tumours suppressors and proteins involved in apoptotic pathway were determined. A band of higher intensity indicate a protein present in relatively higher level compared and vice versa. Densitometry was subsequently performed to quantitatively compare bands intensity. A higher densitometry reading indicates a relatively higher level of protein and vice versa. Human mammary epithelial cell lines MCF-10A was used to determine effect of IMBR1 on normal mammary tissue. Breast cancer cell lines T47D and MDA-MB-468 and osteosarcoma OS-1 cell line were used to determine potential effects on breast cancer and osteosarcoma respectively. Actin, a housekeeping protein, was used as a loading control.

IMBR1 treated MCF-10A, T47D and MDA-MB-468 cells were observed to have increased levels of p53 protein level compared to control. p53 protein was not detected in Saos-2 which was consistent with previous report of Saos-2 being p53 null (Kubbutat et al., 1997) (FIG. 21). Increased p53 protein level suggest an increased level of p53 activity. Thus phosphorylated p53 at Serine 15 (phospho-p53) and p21 was probed for IMBR1 treated MCF-10A, T47D and MDA-MB-468 cells were observed to have increased levels of both phospho-p53 and p21 protein compared to control (FIG. 21). In Saos-2, no obvious difference in p21 protein level between IMBR1 and control treated was observed (FIG. 21). Phospho-p53 was not probed for in Saos-2 as Saos-2 was p53 null.

The effect of IMBR1 on Rb and pRb protein level was next investigated. IMBR1 treated MCF-10A and Saos-2 cells were observed to have increased levels of Rb protein compared to control treated. In contrast, similar amounts of Rb protein was observed in both IMBR1 and control treated T47D cells. Rb was not detected in MDA-MB-468 which was consistent with previous report of MDA-MB-468 being Rb null (Lee et al., 1988). IMBR1 treated MCF-10A and T47D were observed to have increased level of pRb protein compared to control. Due to time limitations of the project, Saos-2 was not probed for pRb. (FIG. 21)

The effect of IMBR1 on phospho-FoxO3a and target gene Bim was then investigated. IMBR1 treated MCF-10A, T47D, MDA-MB-468 and Saos-2 were observed to have increased levels of both phospho-FoxO3a and Bim protein compared to control treated.

The effects of IMBR1 on c-Myc and target gene Bcl-XL was next investigated. Increased levels of both c-Myc and Bcl-XL protein were observed in all cell lines upon IMBR1 treatment (FIG. 21).

Discussion

FGFR1 is Universally Overexpressed and Expressed Abundantly

Data obtained suggest that FGFR1 is universally overexpressed in breast cancer cell lines and expressed abundantly compared to other FGFR in a cell. This observation is similar to previous experiments by Ling et al. (unpublished data).

Abundant expression of FGFR1 suggested that FGFR1 is crucial to cancer cell proliferation and survival. Inhibition of FGFR1 activity could affect cancer cell viability and tumour growth. Thus FGFR1 maybe a potential therapeutic target.

Universal overexpression of FGFR1 in breast cancer cell lines suggested that deregulated FGFR1 is common in breast cancer. FGFR1 inhibitors could thus be useful for a broad group of patients. In addition, FGFR1 mRNA level is lower in MCF-10A which is derived from human mammary epithelial cell line. Thus targeting FGFR1 may have less side effects on normal host mammary tissue.

In OS-1, a primary osteosarcoma cell line, FGFR1 is expressed abundantly compared to other FGFR. Previous experiments by Ling et al. (unpublished results) also show that FGFR1 is expressed abundantly and universally overexpressed in osteosarcoma cell lines.

In addition, FGFR1 is also overexpressed and expressed abundantly at protein level in breast cancer and osteosarcoma cell lines (Ling et al., unpublished results).

Taken together, FGFR1 could be a potential therapeutic target for breast cancer and osteosarcoma cell lines. However, further work may be required to determine expression of FGFR in non-cancer cell lines.

PD166866 and SU5402 decrease breast cancer and osteosarcoma cell line viability Treatment of osteosarcoma cell lines with these two compounds results in decreased cell viability. This suggested that inhibition of FGFR activation and downstream signaling affect cell proliferation and survival. Thus targeting FGFR signaling may be a potential anti-cancer therapy.

However, both PD166866 and SU5402 are not suitable therapeutic agents. SU5402 is not specific for FGFR1 and binds to other receptors which causes potential side effects (Grand et al., 2004). PD166866 does not strongly induce apoptosis or necrosis, and is of limited therapeutic use (Ishibe et al., 2005). Thus, there is a need to develop a compound which is both highly specific for FGFR1 and strongly induce apoptosis or necrosis. IMBR1 was then developed to meet this need.

Observed Effects of IMBR1 is Due to Specific Binding of FGFR1b and FGFR1c

Sandwich ELISA results suggested that IMBR1 binds specifically to FGFR1b and FGFR1c and with higher affinity compared to FGFR2c and FGFR3c. Absorbance produced with FGFR1b and FGFR1c is consistently higher at each IMBR1 dilution compared to FGFR2c and FGFR3c. This suggest that IMBR1 has a higher binding affinity for FGFR1b and FGFR1c. Absorbance level increased in tandem with decreased IMBR1 dilution with FGFR1b and FGFR1c. This suggest that IMBR1 bind specifically to FGFR1b and FGFR1c.

This suggest that effects observed in cell line upon IMBR1 treatment is due to IMBR1 binding to FGFR1b and FGFR1c. However, FGFR family consists of other isoforms. Thus further work is required to determined whether IMBR1 binds to other members of FGFR family.

IMBR1 Affects Cell Viability

GUAVA results suggest that IMBR1 results in a decrease in cell viability in a dose dependent manner and is thus specific. However, decrease cell viability could be due to either necrosis or apoptosis. Thus, the effects of IMBR1 on p53, a key initiator of apoptosis was subsequently investigated.

Effect of IMBR1 on p53 and p21 p53 is a tumour suppressor protein which initiates apoptosis (Ko and Prives, 1996). Phosphorylation of p53 activates p53 transcription activity and increase p53 half-life by preventing binding of MDM2 to p53 which promotes p53 degradation (Lakin and Jackson, 1999).

Activated p53 acts as a transcription factor to promote expression of several genes, among which is p21 (El-Deiry et al., 1993). p21 binds to G1/S-Cyclin dependent kinase (Cdk) and S-Cdk resulting in inhibition of kinase activity and prevent entry into S-phase (Harper et al., 1995).

As expected, IMBR1 treated cells had increased p53 protein level. This suggest an increased p53 activity and half-life. This was further supported by the corresponding increase in phospho-p53 protein level. This suggest that IMBR1 treatment activates p53 signaling pathway.

A possible mechanism for increased p53 protein level in IMBR1 treated cells could be effect of IMBR1 on Akt signaling protein. Phosphorylation of Akt results in Akt activation (Datta et al., 1997). Activation of Akt upon FGFR signaling pathway result in Akt mediated phosphorylation of MDM2. Phosphorylated MDM2 translocate to the nucleus and bind to p53 resulting in p53 degradation (Mayo and Donner et al., 2001). Inhibition of FGFR signaling with IMBR1 may prevent Akt mediated phosphorylation of MDM2 and subsequent MDM2 inhibition of p53. The observed increased in p53 protein level and phosphorylated p53 with IMBR1 treatment could be due to inhibition of downstream Akt activity.

As expected, IMBR1 treated cells displayed increased level of p21 protein compared to untreated cells. This suggests that p53 is activated, leading to increase of p21 protein. Thus lending further that IMBR1 treatment lead to the activation of p53 which lead to p53 upregulation of p21.

Taken together, this suggest that IMBR1 not only induced apoptosis but also halts cell cycle progression via upregulation of p21. However further work needs to be done to lend further support to p53 activation by IMBR1. qRT-PCR could be performed to determine whether p21 is upregulated at transcription level. Effect of IMBR1 on Akt activity can be investigated by performing a Western Blot for phosphorylated Akt.

Effect of IMBR1 on c-Myc and Bcl-XL c-Myc is a transcription factor with tumour suppressor function via suppression of anti-apoptotic protein Bcl-XL (Eischen et al., 2001). Bcl-XL mediates anti-apoptotic function by maintaining the integrity of outer mitochondria membrane to prevent the release of cytochrome c which activates downstream apoptotic pathway (Harris and Thompson, 2000). Bcl-XL may also inactivate pro-apoptotic protein Bax via heterodimerization (Minn et al., 1999).

As expected, IMBR1 treated cells displayed increased level of c-Myc protein. This suggest that IMBR1 treatment led to activation of c-Myc signaling pathway. This was in turn expected to suppress transcription of Bcl-XL gene, leading to decrease Bcl-XL protein level. However, contrary to expectation, there was an increase in Bcl-XL. This suggests that IMBR1 activation of c-Myc signaling pathway does not augment cell death via suppression of Bcl-XL gene transcription. The pro-apoptotic effect of Bcl-XL could be compensated by activity of other apoptotic protein, thus leading to overall decrease in viable cells.

In addition, c-Myc may augment p53 activity. Previous experiments in mouse embryo fibroblast demonstrated that c-myc induce the expression of p19ARF protein; p14ARF in humans (Zindy et al., 1998). p19ARF binds to MDM2, preventing MDM2 from binding to p53 and promoting p53 degradation (Pomerantz et al., 1998). Human p14ARF was also subsequently demonstrated to promote MDM2 degradation (Zhang et al., 1998). Increase in c-Myc upon IMBR1 treatment could lead to increase p19ARF protein level which stabilize p53 and contribute to increased p53 activity.

Taken together, this suggest that c-Myc may be activated with IMBR1 treatment. Future work may be performed to determine the effect of IMBR1 on p19ARF protein level which will shed light on effect of increased c-Myc protein level.

Effects of IMBR1 on Rb and pRb

Retinoblastoma protein (Rb) is a tumour suppressor which prevents excessive cell proliferation. Hypophosphorylated Rb is active and binds E2F, a transcription factor to inhibit cell cycle progression. When cells are about to undergo cellular division, G1-Cdk accumulates and phosphorylates Rb. Hyperphosphorylated Rb are inactivated and dissociates from E2F and subsequently targeted for degradation (Nevins, 2001). E2F is released and enters the nucleus to promote transcription of S-phase genes for cell cycle progression. However, E2F-1 promotes p53 dependent apoptosis. This is via E2F-1 promotion of p19ARF transcription. p19ARF binds to MDM2 to prevent MDM2 promoted degradation of p53 (Qin et al., 1994).

As expected, IMBR1 treated MCF-10A and Saos-2 treated cells displayed increased level of Rb. This suggested that IMBR1 treatment lead to increase level of Rb protein which inhibit cell cycle progression. However, upon IMBR1 treatment in T47D cell, no increase in Rb was observed. This could be due to cellular context of T47D.

Contrary to expectations, IMBR1 treatment result in increased levels of pRb protein in MCF-10A and T47D. A potential explanation could be that Rb is phosphorylated and degraded to release E2F-1. This in turn lead to stabilization of p53 and augment p53-dependent apoptosis.

The presence of two distinct bands suggests that pRb is differentially phosphorylated in terms of phosphorylation level or sites. Previous experiments demonstrate that phosphorylation of Rb at different sites is required for Rb binding to different protein domains (Knudsen and Wang, 1996). Extrapolating, differential phosphorylation of Rb may result in varying binding ability to E2F family members. Thus in T47D, the increase in slower migrating species of pRb may lead to lower binding ability to E2F-1 leading to release of E2F-1 to promote p19ARF transcription. This in turn promotes p53 dependent apoptosis resulting in cell death observed. However, differential phosphorylation of Rb is not observed in IMBR1 treated MCF-10A cells. This suggest that non-cancer and cancer cells respond differently to IMBR1, which may account for lower cell death observed in non-cancer cells.

In addition, increase in slower migrating species of pRb in T47D could be due to increased phosphorylation. Increased phosphorylation may retard migration. c-Myc promotes the transcription of Cdk4 gene (Hermeking et al., 2000). Cyclin D in complex with Cdk4 phosphorylates pRb. Increased c-Myc protein level may result in increased Cdk4 transcription and Cdk4 protein level. This could result in increased pRb phosphorylation and an increase in slower migrating species of pRb.

However, p53 dependent apoptosis may not be heavily dependent on Rb effect on E2F-1 and p19ARF. MDA-MB-468 cell line also displayed significant increase in cell death with IMBR1 treatment despite being Rb null. This suggest that additional mechanisms may be present to augment p53 dependent death or that Rb effect on p53 dependent apoptosis may not be very significant. In addition, Saos-2 cell line displayed increased Rb protein level upon IMBR1 treatment, indicating that E2F-1 may not be released while displaying significant increase in cell death with treatment.

This suggests that IMBR1 induced apoptosis in Saos-2 may not be dependent on Rb effect on E2F-1 and p19ARF.

Thus, Rb effect on E2F-1 and p19ARF may not have a very significant effect and that the effect of IMBR1 on Rb differs between cancer cell lines.

Effect of IMBR1 on FoxO3a and Bim

Forkhead box O3 (FoxO3a) is a transcription factor with tumour suppressor functions. FoxO3a upregulates the expression of various pro-apoptotic protein including Bim and downregulates anti-apoptotic protein (Sunters et al., 2003; Skurk et al., 2004). FGFR1 signaling activates downstream Akt/PKB which result in FoxO3a phosphorylation. Phospho-FoxO3a activity is inhibited and translocated out of the nucleus (Brunet et al., 1999). Thus binding of IMBR1 to FGFR1 was expected to decrease FGFR1 signaling which would lead to decrease phosphorylation of FoxO3a and increase Bim protein level.

The observed slight increase in phospho-FoxO3a could be due to cross talk between p53 pathway and FoxO3a. p53 induces the expression of serum/glucocorticoid-inducible kinase 1 (SGK1) which phosphorylates FoxO3a. Phospho-FoxO3a is inhibited and translocate out of the nucleus (You et al., 2004). Nuclear FoxO3a inhibits p53 transcriptional activity (You et al., 2006). The observed slight increase in phospho-FoxO3a could be induced by p53 pathway to stabilize p53 transcription activity.

Increased Bim protein level could be due to FoxO3a promotion of Bim gene expression. This suggested that sufficient level of active FoxO3a could still remain in the nucleus despite p53 induced phosphorylation. To verify this, qRT-PCR and Western Blot could be performed to determine mRNA and protein level of FoxO3a regulated genes. These gene are PUMA, Bax (You et al., 2006) and FLICE-inhibitory protein (Skurk et al., 2004).

IMBR1 May Cause Potential Side Effects

Effect of IMBR1 on tumour suppressors and proteins involved in apoptotic pathway in MCF-10A was observed to be similar to IMBR1 effect on breast cancer and osteosarcoma cell lines. This suggests that IMBR1 may also affect normal host tissue, resulting in side effects.

Conclusion

Inhibition of FGFR1 signaling via IMBR1 results in activation of p53 pathway, increased protein level of tumour suppressor and increased protein level of pro-apoptotic protein. This suggests that FGFR1 signaling in cancer prevents activation of apoptotic pathway and activation of tumour suppressor proteins which puts a brake on rapid proliferation. Thus FGFR1 signaling contributes to cancer cell survival and proliferation.

Based on experiments performed in this Example and from previous experiments performed in the Examples described above. IMBR1 was deemed to be a potential anti-cancer therapy which targets FGFR1.

Abbreviations for Example 14

The following is a list of abbreviations (in alphabetical order) used in Example 14:
BCL-XL—B-cell lymphoma-extra large
BIM—Bcl-2-like protein 11
DMSO—Dimethyl sulfoxide
ELISA—Enzyme-linked immunosorbent assay
FGF—Fibroblast Growth Factor
FGFR—Fibroblast Growth Factor Receptor
FoxO3a—Forkhead box O3a
FRS2—Fibroblast growth factor receptor substrate 2
GAB1—GRB2-associated-binding protein 2
GAPDH—Glyceraldehyde 3-phosphate dehydrogenase
GRB2—Growth factor receptor-bound protein 2
HRP—Horseradish peroxidase
HSPG—Heparin sulfate proteoglycans
IC50—Half maximal inhibitory constant
Ig—Immunoglobulin-like
Ins (1,4,5) P3—inositol (1,4,5)-triphosphate
phospho-FoxO3a—phosphorylated Forkhead box O3a
phospho-p53—phosphorylated p53 at Serine15
pRb—phosphorylated Retinoblastoma protein
PI3K—Phosphoinositide-3 kinase
PTB—Phosphotyrosine-binding domain
qRT-PCR—Quantitative Real Time Polymerase Chain Reaction
Rb—Retinoblastoma protein
REU—Relative expression units
Shb—SH2 domain-containing adaptor protein B
SOS—Sons of sevenless homolog
SH2—Src homology 2
Y—Tyrosine

REFERENCES FOR EXAMPLE 14

Altamore, D. A. and Testa, J. R., 2005. Pertubations of the Akt signalling pathway in human cancer. Oncogene 24, 7455-7464.

Balmanno, K. and Cook, S. J., 2009. Tumour cell survival signalling by the ERK1/2 pathway. Cell Death Differ 16, 368-377.

Brunet, A., Bonni, A., Zigmond, M. J., Lin, M. Z., Juo, P., Su, L. S., Anderson, M. J., Arden, K. C., Blenis, J., Greenberg, M. E., 1999. Akt promotes cell survival by phosphorylating and inhibiting a forkhead transcription factor. Cell 96, 857-868.

Datta, S. R., Dudek, H., Tao, X., Masters, S., Fu, H., Gotoh, Y., Greenber, M. E., 1997. Akt phosphorylation of Bad couples survival signals to the cell-intrinsic death machinery. Cell 91, 231-241.

Doherty, P. and Walsh, F. S., 1996. CAM-FGF receptor interactions: a model for axonal growth. Mol Cell Neurosci 8, 99-111.

Downward, J., 2003. Targeting RAS signalling pathways in cancer therapy. Nat. Rev. Cancer 3, 11-22

Eischen, C. M., Woo, D., Roussel, M. F., Cleveland., J. L., 2001. Apoptosis Triggered by Myc-Induced Suppression of Bcl-XL or Bcl-2 Is Bypassed during Lymphomagenesis. Mol Cell Bio 21, 5063-5070.

El-Deiry, W. S., Tokino, T., Velculescu, V. E., Levy, D. B., Parsons, R., Trent, J. M., Lin, D., Mercer, W. E., Kinzler, K. W., Vogelstein, B., 1993. WAF1, a Potential Mediator of p53 Tumor Suppression. Cell 75, 817-825.

Furdui, C. M., Lew, E. D., Schlessinger, J., Anderson, K. S., 2006. Autophosphorylation of FGFR1 Kinase is Mediated by a Sequential and Precisely Ordered Reaction. Mol Cell 21, 711-717.

Grand., E. K., Chase., A. J., Health, C., Rahemtulla, A., Cross, N. C. P., 2004. Targeting FGFR3 in multiple myeloma: inhibition of t (4;14)-positive cells by SU5402 and PD173074. Leukemia 18, 962-966

Groth, C and Lardelli, M, 2002. The structure and function of vertebrate Fibroblast Growth Factor Receptor. Int. J. Dev. Biol 46, 393-400.

Harper, J. W. Adami, G. R., Wei, N., Keyomarsi, K., Elledge, 1993. The p21 Cdk-Interacting Protein Cip1 is a Potent Inhibitor of G1 Cyclin-Dependent Kinases. Cell 75, 805-816.

Harper, J. W., Elledge, S. J., Keyomarsi, K., Dynlacht, B., Tsai, L. H., Zhang, P., Dobrowolski, S., Bai, C., Connell- Crowley, L., Swindell, E., 1995. Inhibition of Cyclin-dependent Kinases by p21. Mol Bio Cell 6, 387-400.

Harris, M. H. and Thompson, C. B., 2000. The role of the Bcl-2 family in the regulation of outer mitochondrial membrane permeability. Cell Death Differ 7, 1182-1191.

Haugsten, E. M., Wiedlocha, A., Olsnes, S., Wesche, J., 2010. Roles of Fibroblast Growth Factor Receptors in Carcinogenesis. Mol Cancer Res 8, 1439-1452.

Hermeking, H., Rago, C., Schuhmacher, M., Li, Q., Barett, J. F., Obaya, A. J., O'Connell. B. C., Mateyak, M. K., Tam, W., Kohluber, F., Dang, C. V., Sedivy, J. M., Eick, D., Vogelstein, B., Kinzler, K. W., 2000. Identification of CDK4 as a target of c-MYC. PNAS 97, 2229-2234.

Ishibe, T., Nakayama, T., Aiyama, T., Nishijo, K., Shibata, K. R., Shima, Y., Nagayama, S., Katagiri, T., Nakamura, Y., Nakamura, T., Toguchida., J., 2005. Disruption of Fibroblast Growth Factor Signal Pathway Inhibits the Growth of Synovial Sarcomas: Potential Application of Signal Inhibitors to Molecular Target Therapy. Clin Cancer Res 11, 2702-2712.

Johnson, D. E., Lee, P. L., Lu, J., Williams, L. T., 1990. Diverse forms of a receptor for acidic and basic fibroblast growth factors. Mol Cell Biol 10, 4728-36.

Kan, M., Wang, F., Xu, J., Crabb, J. W., Hou, J., McKeehan, W. L., 1991. An essential heparin-binding domain in the fibroblast growth factor receptor kinase. Science 259, 1918-21.

Knudsen, E. S. and Wang, J. Y. J., 1996. Differential Regulation of Retinoblastoma Protein Function by Specific Cdk Phosphorylation Sites. J Biol Chem 271, 8313-8320.

Kubbutat, M. H. G., Jones, S>N., Vousden, K. H., 1997. Regulation of p53 stability by Mdm2. Nature 387, 299-303.

Kim, I., Moon, S., Yu, K., Kim, U., Koh, G Y., 2001. A novel fibroblast growth factor receptor-5 preferentially expressed in the pancreas. Biochim Biophys Acta 1518, 152-6.

Ko, L. J. and Prives, C., 1996. p53: puzzle and paradigm. Genes Dev 10, 1054-1072.

Lakin, N. D. and Jackson, S. P., 1999. Regulation of p53 in response to DNA damage. Oncogene 18, 7644-7655.

Landgren, E., Klint, P., K, Yokote., Claesson-Welsh, L., 1998. Fibroblast growth factor receptor-1 mediated chemotaxis independently of direct SH2-domain protein binding. Oncogene 17, 283-291

Lee, E. Y. H. P, Shew, J. Y., Bookstein, R., Scully, P., Lee, W. H., 1988. Inactivation of the Retinoblastoma Susceptibility Gene in Human Breast Cancers. Science 241, 218-221.

Ley, R., Balmanno, K., Hadfield., K., Westom, C., Cook, S. J., 2003. Activation of the ERK1/2 Signaling Pathway Promotes Phosphorylation and Proteasome-dependent Degradation of the BH3-only Protein, Bim. J Biol Chem 278, 18811-18816.

Mayo, L. D. and Donner, D. B., 2001. A phosphatidylinositol3-kinase/Akt pathway promotes translocation of Mdm2 from the cytoplasm to the nucleus. Proc. Natl. Acad. Sci. USA 98, 11598-11603.

Minn, A. J., Kettlun, C. S., Liang, H., Kelelkar, A., Heider, M. G. V., Chang, B. S., Fesik, S. W., Fill, M., Thompson, C. B., 1999. Bcl-XL regulates apoptosis by heterodimerization-dependent and -independent mechanism. EMBO 18, 632-643.

Mohammadi, M., McMahon, G., Sun, L., Tang, C., Hirth, P., Yeh, B. K., Hubbard, S. R., Schlessinger, J., 1997. Structures of the Tyrosine Kinase Domain of Fibroblast Growth Factor Receptor in Complex with Inhibitor. Science 276, 955-950.

Nathan, S. S., Pereira, B. P., Zhou, Y., Gupta., A., Dombrowski, C., Soong, R., Pho, R. W. H., Stein, G. S., Salto-Tellex, M., Cool, S. M., van Wijnen, W. J., 2009. Elevated expression of Runx2 as a key parameter in the etiology of osteosarcoma. Mol Bio Rep 36, 153-158.

Nevins, J. R., 2001. The Rb/E2F pathway and cancer. Hum. Mol. Genet. 10, 699-703.

Panek, R. L., Iu, G. H., Dahring, W. K., Batley, B. L., Connolly, C., Hamby, J. M., Brown, K. J., 1998. In Vitro Biological Characterization and Antiangiogenic Effects of PD 1668666, a Selective Inhibitor of the FGF-1 Receptor Tyrosine Kinase. J Pharmacol Exp Ther 286, 569-577.

Pomerantz, J., Schreiber-Agus, N., Liegeois, N. J., Silvermam, A., Alland, L., Chin, L., Potes, J., Chen, K., Orlow, I., Lee, H. W., Cordon-Cardo, C., DePhino, R. A., 1998. The Ink4a Tumor Suppressor Gene Product, p19ARF, Interacts with MDM2 and Neutralizes MDM2's Inhibition of p53. Cell 92, 713-723.

Prendergast, G. C., 1999. Mechanism of apoptosis by c-Myc. Oncogene 18, 2867-2897.

Rhee, S. G., 2001. Regulation of phosphoinositoide-specific phospholipase C. Annu Rev Biochem 70, 281-312

Qin, X., Livingston, D. M., Kaelin, W. G., Adams, P. D., 1994. Deregulated transcription factor E2F-1 expression leads to S-phase entry and p53 mediated apoptosis. PNAS 91, 10918-10922.

Schlessinger, J., Plotnikov, A. N., Ibrahimi, O. A., Eliseenkova, A. V., Yeh, B. K., Yayon, A., Linhardt, R. J., Mohammadi, M., 2000. Crystal Structure of a Ternary FGF-FGFR-Heparin Complex Reveals a Dual Role for Heparin in FGFR Binding and Dimerization. Mol Cell 6, 743-750.

Skurk, C., Maatz, H., Kim, H., Yang, J., Abid, M. R., Aird, W. C., Walsh, K., 2004. The Akt-regulated Forkhead Transcription Factor FOXO3a Controls Endothelial Cell Viability through Modulation of the Caspase-8 Inhibitor FLIP. J Biol Chem 279, 1513-1525.

Sleeman, M., Fraser, J., McDonald, M., Yuan, S., White, D., Grandison, P., Kumble, K., Watson, J. D., Munson, J. G., et al., 2001. Identification of a new fibroblast factor receptor, FGFR5. Gene 271, 171-82.

Sunters, A., de Mattos, S. F., Stahl, M., Brosens, J. J., Zoupoulidou, G., Saunuder, C. A., Coffer, P. J., Medema, R. H., Coombes, R. C., Lam, E. W. F., 2003. FoxO3a Transcriptional Regulation of Bim Controls Apoptosis in Paclitaxel-treated Breast Cancer Cell Lines. J Biol Chem 278, 49795-49805.

Turner, N. and Grose, R., 2010. Fibroblast growth factor signalling: from development to cancer. Nat Rev Cancer 10, 116-129.

You, H., Jang, Y., You-ten, A. I., Okada, H., Liepa, J., Wakeham, A., Zaugg, K., Mak, T. W., 2004. p53-dependent inhibition of FKHRL1 in response to DNA damage through protein kinase SGK1. PNAS 101, 14057-14062.

Zhang, Y., Xiong, Y., Yarbrough, W. G., 1998. ARF promotes MDM2 degradation and stabilizes p53: ARF-INK4a locus depletion impairs both the Rb and p53 tumor suppressor pathways. Cell 92, 725-734.

Zindy, F., Eischen, C. M., Randle, D. H., Kamijo, T., Cleveland, J. L., Sherr, C. J., Roussel, M. F., 1998. Myc signalling via the ARF tumor suppressor regulates p53-dependent apoptosis and immortalization. Genes Dev 12, 2424-2433.

Example 15

IMB-R1 is a polyclonal anti-sera which contains other components in the rabbit sera, including proteins or other antibodies, though the specific antibody desired is in much higher concentration. We have purified the specific antibody from two batches of the sera containing IMB-R1 using affinity chromatography, using the following protocol.

1. Prepare the Peptide Antigen to Immunize the Rabbits

Peptide CSSSEEKETDNTKPNR was synthesized and coupled to KHL so it becomes KHL-C-SSSEEKETDNTKPNR 2. Immunization of the Rabbit:

New Zealand White rabbits are used for the immunisation protocol.

| Phase | Procedure | Description of used procedure | Time of realisation |
|---|---|---|---|
| 1 | 1$^{st}$ injection of antigen | Rabbit immunised using 250 micrograms of antigen (KHL-C-SSSEEKETDNTKPNR) | Day 1 (after delivery of peptide and coupling) |
| 2 | 2$^{nd}$ injection of antigen | Rabbit immunised using 250 micrograms of antigen | Day 19-21 |
| 3 | Sera after 2$^{nd}$ injection | Collection of sera after 2$^{nd}$ injection of antigen | Day 26-28 |
| 4 | Testing sera | Testing of the sera after 2$^{nd}$ injection using dot-blot. | Day 29-30 |
| 5 | 3$^{rd}$ injection of antigen | Rabbit immunised using 250-500 micrograms of antigen - based on rabbit response after 2$^{nd}$ injection | Day 49-51 |
| 6 | Sera after 3$^{rd}$ injection | Collection of sera after 3$^{rd}$ injection of antigen | Day 56-58 |
| 7 | Testing sera | Testing of the sera after 2$^{nd}$ injection using dot-blot. | Day 59-61 |
| 8 | 4$^{th}$ injection of antigen | Rabbit immunised using 250-500 micrograms of antigen - based on rabbit response after 2$^{nd}$ injection | Day 79-81 |
| 9 | Termination of rabbit | Final collection of 50-80 ml of rabbit sera | Day 86-88 |

3. Affinity Purification of 20 Ml of Best Responding Sera:

Day 1:
a) Wash Pierce 6× Reactigel beads (Cat. #20259) (0.5 ml) in an eppendorf tubes (to exchange the acetone), with 0.1 M Sodium Borate buffer (pH 9.0). This is optional as the peptide coupling can occur even in the presence of acetone.
b) Add 5 mg of peptide (1-5 mg) to the beads and make up the volume to 1.5 ml with the Borate buffer.
c) Mix peptide and beads overnight with rotation at room temperature.

Day 2:
d) Spin the beads, remove the supernatant and add 1 ml of 1M Tris-HCl (pH 8.8) and mix throughout the day.
e) Wash away residual peptide very well [about 10-15 washes in PBS-Tween-20 (0.1%) depending upon the volume of each wash].
f) Add the beads (containing from 1-5 mg of coupled peptide) to a 50 ml tube containing up to 50 ml of serum and mix overnight.

Day 3
g) Spin down the beads and keep the serum.
h) Wash the beads with PBS-Tween-20 (0.1%), transfer the beads to an eppendorf tube, then add 1 ml of 0.1M Glycine (pH 2.5) for 30 minutes to elute the IgG.
j) Remove the supernatant (1 ml) and add it to 0.15 ml of 1.5 M Tris-HCl (pH 8.8) to neutralize the acid.
k) Add another 1 ml of 0.1M Glycine (pH 2.5) to the beads and mix beads for 30 minutes.
l) Repeat step k) again 3 more times.
m) Run a 10 or 12% SDS gel of 10 μl of each fraction to see in which fractions the IgG came off. They usually are fractions 1, 2, and 3.
n) Measure the Ig concentration using Bio-Rad Protein Assay (standard curve is done by using bovine gamma globulin). The beads can be reused.

Reapply the 1× used serum to the beads and repeat the purification steps to see if all the IgG adsorbed from the serum.

The two batches used were called 74 and 75 and the affinity purified IMB-R1 from them were named 74-1.3 and 75-1.5. The effect of these antibodies on the growth of MG63 cells were examined by GUAVA EasyCyte flow cytometry system. Briefly, cells were treated with 8 ug/ml rabbit IgG (as vehicle control), 74-1.3 or 75-1.5 or IMB-R1 (1:250 dilution) for 48 hrs before the viable cell numbers were measured by GUAVA system.

Figure 24:
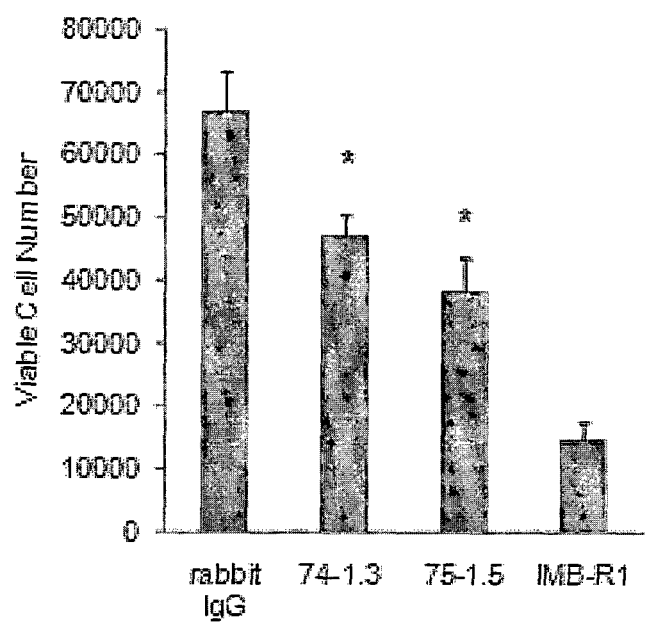
FIG. 24. Graph showing inhibition of cell growth by affinity purified IMB-R1.

Results: At 8 ug/ml, 75-1.5 induced 47% inhibition of cell growth, while 75-1.5 reduced cell growth by 30%. IMB-R1 served as the positive control (FIG. 24). Therefore, the affinity purified IMB-R1 is able to inhibit MG63 cell growth, similar to our previously reported effect of non-purified IMB-R1, which strongly suggested that the ability of IMB-R1 to kill cancer cells is due to its specific anti-FGFR1 activity but not any other non-relevant components in the rabbit sera.

Example 16

Figure 25:
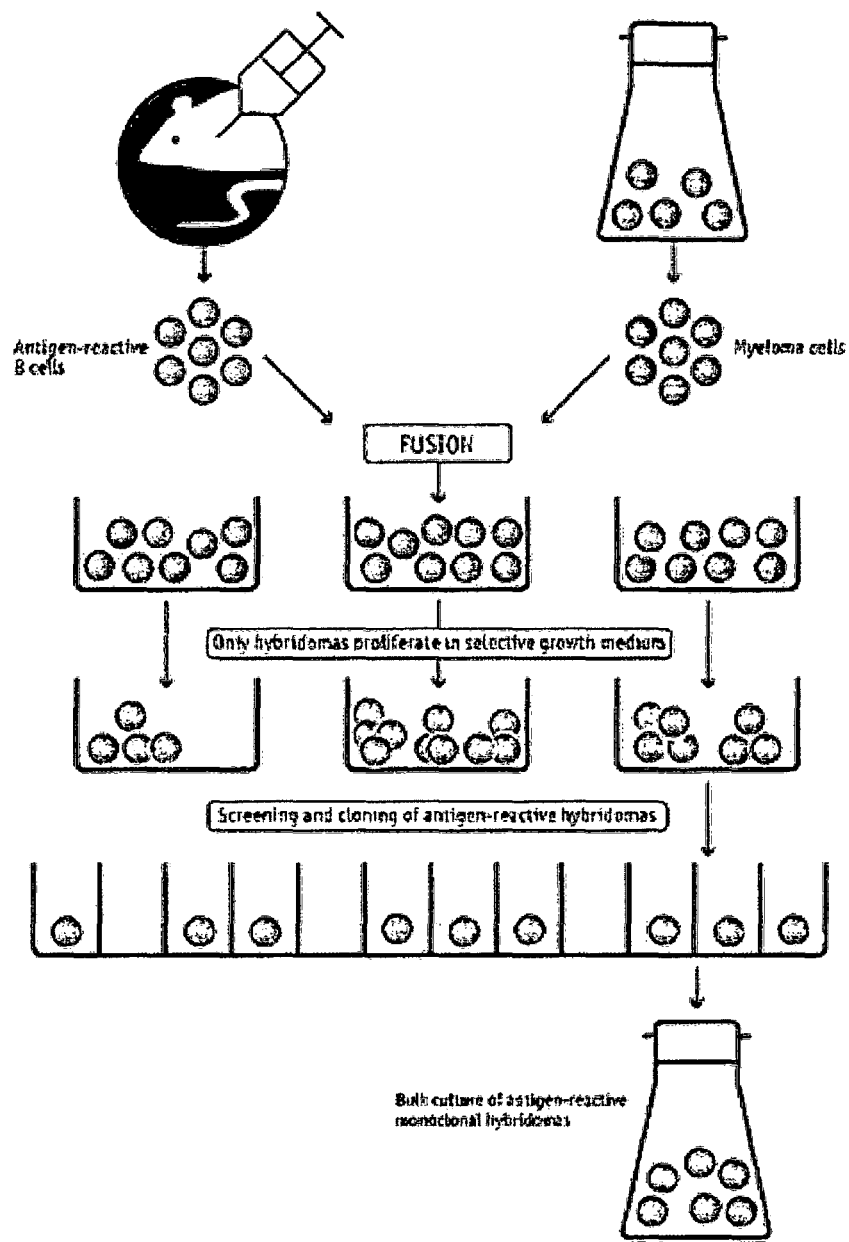
FIG. 25. Diagram illustrating the making of monoclonal IMB-R1 (IMBR1 mAb).

The data described above has shown that the polyclonal IMB-R1 is able to potently neutralize (antagonize) FGFR1 signaling and induce cancer cell death. Therefore we further developed a monoclonal antibody against the same antigen peptide (SSSEEKETDNTKPNR) as that of IMB-R1 using the protocol described below (and as shown in FIG. 25).

1. Prepare the Peptide Antigen to Immunize the Mouse

Peptide CSSSEEKETDNTKPNR was synthesized and coupled to KHL so it becomes KHL-C-SSSEEKETDNTKPNR which was used as the antigen.

2. Immunization of the Mice

BALB/C mice were used for the immunisation protocol.
Freund's Adjuvant, Complete (from SIGMA, F5881)
Freund's Adjuvant, Incomplete (from SIGMA, F5506)
For each protein we used 4 mice.

Immunisation Protocol
1) First injection—day 1: intraperitoneal injection of 10-50 mg of the antigen (KHL-C—SSSEEKETDNTKPNR) (in complete Freund's adjuvants).

2) Second injection—day 21: intraperitoneal injection of 10-50 mg of the antigen (in incomplete Freund's adjuvants).
3) Third injection—day 42: intraperitoneal injection of 10-50 mg of the antigen (in incomplete Freund's adjuvants).
4) Fourth injection—day 45: intraperitoneal injection of 10 mg of the antigen (in PBS).
5) Fifth injection—day 46: intraperitoneal injection of 10 mg of the antigen (in PBS).
6) Fusion—day 47.

3. Fusion Protocol

Preparation 1—Culture Media

Culture Media

| | |
|---|---|
| D-MEM Medium1000 mg/L glucose (SIGMA, D6046) | 400 mL |
| Penicillin & Streptomycin (PNS) (Gibco, 15140), 1% | 5 mL |
| FBS (Biochrom, S0115), 10% | 50 mL |
| 200 nM Glutamine (Gibco, 25030), 1% | 5 mL |

Fusion Media (w/o FBS)

| | |
|---|---|
| D-MEM Medium1000 mg/L glucose (SIGMA, D6046) | 450 mL |
| Penicillin & Streptomycin (PNS) (Gibco, 15140), 1% | 5.5 mL |

Selection AH Media (SIGMA A9666)

| | |
|---|---|
| D-MEM Medium1000 mg/L glucose (SIGMA, D6046) | 400 mL |
| Penicillin & Streptomycin (PNS) (Gibco, 15140), 1% | 5 mL |
| FBS (Biochrom, S0115), 20% | 100 mL |
| 200 nM Glutamine (Gibco, 25030), 1% | 5 mL |
| Lyophilized AH (Azaserine-Hypoxanthine, 50x, γ-irradiated, Sigma A9666), 1x 1 vial | |

Polyethylene Glycol 1500 (PEG 1500, 50% w/v, Roche, 10783641001)

Preparation 2—SP2 Cells (One Week Before Fusion to have Enough Well-Growing Cells) Prepare SP2 Cells in Culture Media Fusion Remove spleen from mice to sterile Petri. Rinse with Fusion media.
Poke the spleen with needle many times & wash out the splenocytes with needle pointing sideways. Scratch the spleen to release more splenocytes.
Do NOT disturb the media & allow the large particles to settle down & transfer as much of the media with splenocytes (avoiding the large particles) to a 50 mL falcon tube.
Meanwhile prepare the SP2 (myeloma cells)—transfer to Fusion media.
Spin down splenocytes from media, at 1000 rpm for 10 min (under such conditions at all times unless specified).
After the spin, remove supernatant till a tiny drop of media is left with the cell pellet, gently tapped the tube to loosen the cell pellet.
Wash once with 35 mL of fresh Fusion media gently & ensure that all cells are well resuspended.
Spin for 10 min at 1000 rpm.
Remove supernatant until a tiny drop of media is left & gently tap the cell pellet. Mix the myeloma cells and splenocytes by the ratio of 5 splenocytes:1 myeloma SP2 cells in 40 ml of Fusion media in falcon tube.
Spin for 7 min at 1200 rpm.
Remove as much supernatant as possible and tap to loosen pellet in solution.
Add 0.8 mL of PEG (for 1 fusion), to fused resuspended and mixed myeloma cells and splenocytes slowly drop by drop.
Add 10 mL of Fusion media slowly drop by drop.
Add another 10 mL of Fusion media.
Spin for 6 min at 1000 rpm.
Remove Fusion media & resuspend the cell pellet in 50 mL of AH media.
Plate 50 □l of fusion cells per well in 96 well plate and add 50 □l of AH media to each well.
Start the screening of fusion at day 10 or 11.

3. After screening, the hybridoma clones 6D10 and 6E5 were chosen as the positive clones and their isotypes were determined as IgG1, Kappa. They were re-cloned and purified as mouse IgG1. The protocol to purify these mouse IgG1 from mouse ascites is the standard High Salt method described in the book "Antibodies: a laboratory manual" by Edward Harlow and David Lane (1988), page 311.

Protocol:
1) Add 1/10 volume of 1.0M sodium borate (pH8.9) to the ascites and then check the pH. This is to adjust the concentration of NaCl to 3.3M.
2) Pass the above solution of antibody through a protein A bead column. The monoclonal antibody in ascites is estimated to be 1-10 mg/ml. The capacity of protein A beads to bind to IgG1 is expected to be 5 mg/ml.
3) Thereafter, the beads are washed with 10 volumes of 3.0M NaCl, 50 mM sodium borate (pH8.9). Repeat the washing one more time.
4) Elute the IgG from the column with 100 mM glycine (pH3.0). Adjust the pH of the elutes to neutral pH by 1M Tris (pH8.0). Avoid bubbling or frothing when handling the solutions.
5) Determine the IgG concentration by absorbance at 280 nm (1 OD=0.8 mg/ml).

By following this approach we have now purified two clones 6D10 and 6E5 and their isotypes were determined as IgG. The monoclonal antibodies have great potential as an anti-cancer therapy because they are more specific than small-molecule inhibitors, and they work on the cell surface which does not require the therapeutic reagents to enter into cells.

To examine whether IMB-R1 mAbs has specificity for FGFR1 but not other FGFRs, we used ELISA assays. FGFR1, 2 and 3 have splice variants "b" and "c". The "c" splice form exhibits responsiveness to more FGF ligands than the "b" slice form, especially in the cases of FGFR2 and FGFR3. First, ELISA plates were coated with goat anti-human IgG-Fc (Jackson ImmunoResearch Labs), followed by blocking with 2% BSA. The plates were next incubated with 100 ng/ml FGFR isoforms conjugated with Fc fragment or control human IgG, and then incubated with various concentrations of IMB-R1 mAb clone 6D10 or 6E5, or normal mouse IgG as the control. Thereafter, the bound antibodies were detected with HRP conjugated goat anti-mouse IgG (Jackson ImmunoResearch Labs) and visualized by TMB substrate. The developed color was measured using Victor$^3$ multiplate reader at wavelength 450 nm. The raw data were normalized by the readings of the control wells. The higher the reading indicated higher affinity of IMB-R1 mAb to the FGFRs.

Figure 26:
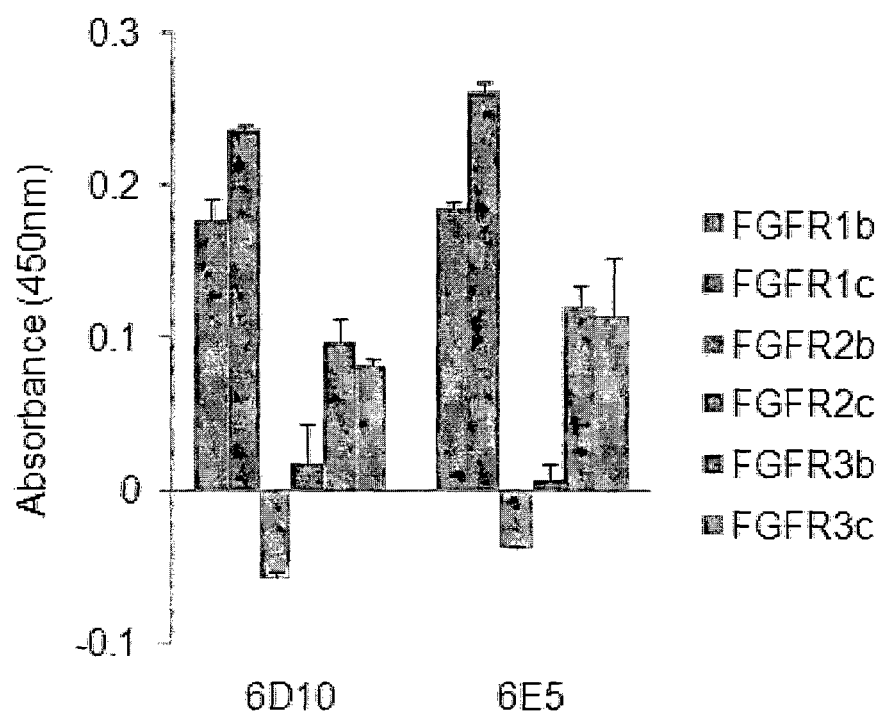
FIG. 26. Graph showing that IMBR1 mAb clones (6D10 and 6E5) preferentially bind to FGFR1.

As shown in FIG. 26, IMB-R1 mAbs bind to FGFR1 and FGFR3 but not FGFR2. The affinity of IMB-R1 mAb to FGFR1 was higher than FGFR3. Clone 6D10 and 6E5 have higher affinity to FGFR1c than FGFR1b. Approximately, the affinity of 6D10 to FGFRs is at the ratio of: FGFR1:FGFR2:FGFR3=35:1:15; while the affinity of 6D10 to FGFRs is: FGFR1:FGFR2:FGFR3=38:1:20. IMB-R1 mAbs have a higher affinity to FGFR1 than to the other two FGFRs.

To verify the IMB-R1 mAbs indeed bind to the cell surface, we incubated live (without fixation) MG63 cell suspension with 6D10 or 6E5 followed by Alexa 488 conjugated anti-mouse antibody and then analyzed the cell surface staining by flow cytometry. We tested the purified IMB-R1 mAbs, and also IMB-R1 and two commercial FGFR1 monoclonal antibodies from R&D (MAB765) and Santa Cruz (SC-57130). The concentration of IMB-R1 was 1:200, while all monoclonal antibodies were at 2 µg/ml. Control cells were stained with isotype control. Histogram was plotted.

Figure 27:
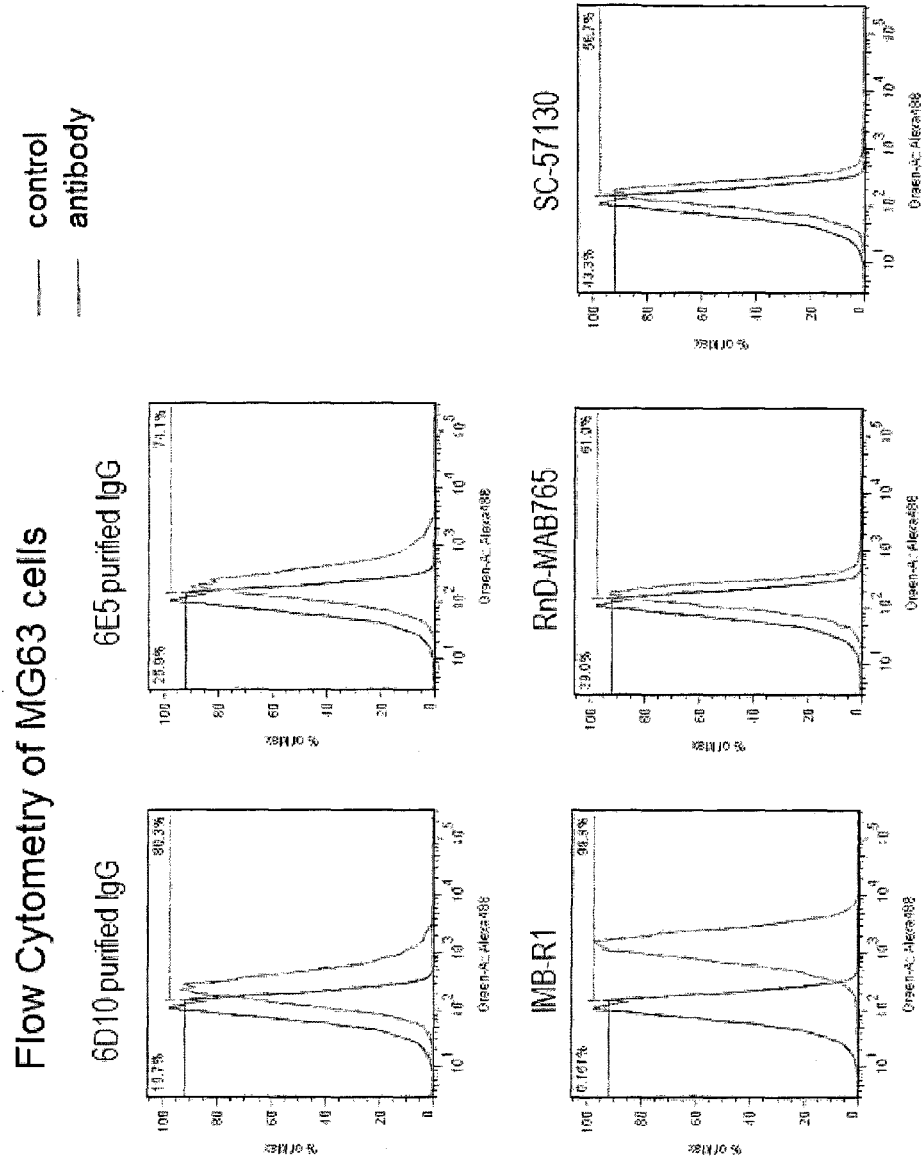
FIG. 27. Figure showing that IMBR1 mAb clones bind to the cell surface. RnD-MAB765 and SC-57130 are commercial monoclonal antibodies of FGFR1 from R&D systems and Santa Cruz, respectively.
Figure 28:
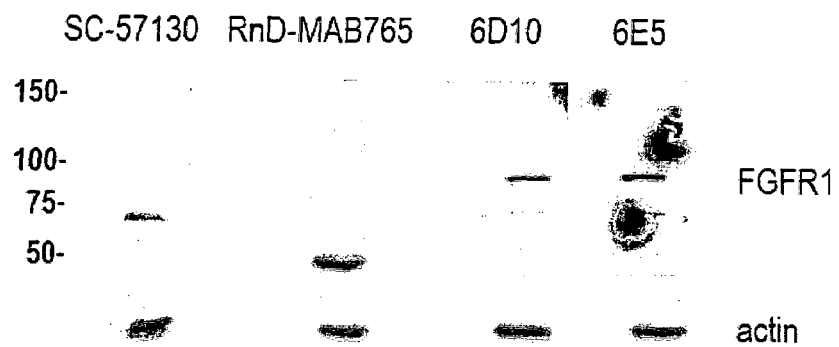
FIG. 28. Figure showing binding of IMBR1 mAb clones to denatured protein (MG63 total cell lysate).

As shown in FIG. 27, the shift of the antibody of interest from the control indicated positive staining. IMB-R1 showed strong positive staining on cell surface. Both 6D10 and 6E5 were also able to bind to cell surface. The two commercial antibodies bound to cell surface weakly.

Previous data in ELISA and flow cytometry demonstrated IMB-R1 mAbs were able to recognize the epitopes in native condition. We next examined whether they worked well in recognizing denatured protein. We denatured 20 ug MG63 cell lysate and performed SDS-PAGE and Western Blotting using 6D5 and 6E5 at 1 ug/ml. The two commercial antibodies were included for comparison.

As shown in FIG. 28, 6D10 and 6E5 identically recognized an intense protein bands at about 90 kDa, and a faint band at around 75 kDa. SC-57130 also recognized the latter band. MAB765 detected a band at lower molecular weight which was around 50 kDa. The human FGFR1 protein has 820 amino acids and the molecular weight is approximately 75 kDa. With the often post-translational modification—glycosylation, the predicted molecular weight on SDS-PAGE is usually 75-100 kDa. Therefore, the bands detected by 6D10/6E5 and SC-57130 were most likely full-length FGFR1.

The effect of IMB-R1 mAbs on cell growth was studied and compared with IMB-R1. MG63 and MDA-MB468 cells were treated with 2 or 20 µg/ml IMB-R1 mAbs or IMB-R1 at 1:125 dilution for 3 days. Rabbit IgG and mouse IgG were the vehicle control for IMB-R1 and IMB-R1 mAbs, respectively. The viable cells were counted by GUAVA Viacount system. The statistics was done by Student's t test. P<0.05 was considered as significantly different.

Figure 29:
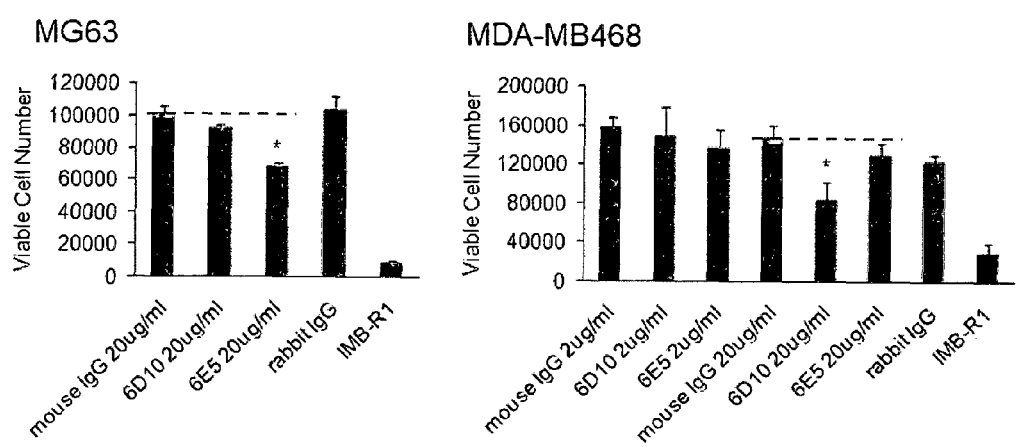
FIG. 29. Graphs showing that IMBR1 mAb clones inhibited cell growth.

As shown in FIG. 29, 20 µg/ml 6E5 reduced MG63 cell growth by 31.5%, while 6D10 slightly reduced the cell numbers but without statistical significance. While in the case of MDA-MB468, 6D10 at 20 µg/ml inhibited cell growth by 42.8% but 6E5 did not affect cell growth significantly. The data showed that IMB-R1 mAbs were able to inhibit the cancer cell growth. The more significant inhibition might be observed upon applying higher dosage. However, different mAbs showed different effectiveness in different cells. Unlike IMB-R1 which is a polyclonal antibody recognizing multiple epitopes on the antigen, monoclonal antibody only recognize one single epitope. That can be why IMB-R1 is able to recognize FGFR1 in different cells, but one monoclonal IMB-R1 might not be able to do that if its epitope is masked in certain cells but another monoclonal IMB-R1 can recognize because it recognizes a different epitope.

The invention claimed is:

1. A method of treating a cancer in a subject in need of treatment, the method comprising administering an FGFR1 antibody to the subject, wherein the FGFR1 antibody binds FGFR1 at an epitope consisting of an amino acid sequence having less than 20 amino acids and at least 8 contiguous amino acids of the amino acid sequence SSSEEKETDNTKPNR [SEQ ID NO:2], and wherein cells in the cancer express FGFR1 on the cell surface.

2. A method of treating a cancer in a subject in need of treatment, the method comprising administering an FGFR1 antibody to the subject, wherein the FGFR1 antibody binds to FGFR1, and is capable of binding to the peptide SSSEEKETDNTKPNR [SEQ ID NO:2], wherein the epitope for the FGFR1 antibody consists of all or part of the amino acid sequence SSSEEKETDNTKPNR [SEQ ID NO:2], and wherein cells in the cancer express FGFR1 on the cell surface.

3. A method of treating a cancer according to claim 1 wherein the FGFR1 is human FGFR1 having the amino acid sequence of SEQ ID NO:1 or an amino acid sequence having at least 60% sequence identity to SEQ ID NO:1.

4. A method of treating a cancer according to claim 1 wherein the treatment involves induction of programmed cell death in cells expressing FGFR1.

5. A method of treating a cancer according to claim 1 wherein the cancer is a sarcoma or a carcinoma.

6. An in vitro method of causing cell death in cancerous cells, the method comprising contacting cancerous cells in vitro with an FGFR1 antibody that binds to FGFR1, and is capable of binding to the peptide SSSEEKETDNTKPNR [SEQ ID NO:2], wherein the epitope for the FGFR1 antibody consists of all or part of the amino acid sequence SSSEEKETDNTKPNR [SEQ ID NO:2], and wherein the cancerous cells express FGFR1 on the cell surface.

7. The method of claim 6 wherein the cancerous cells are sarcoma or carcinoma cells.

8. The method of claim 6 wherein the method involves the induction of programmed cell death in the cancerous cells.

9. A method of treating a cancer according to claim 2 wherein the FGFR1 is human FGFR1 having the amino acid sequence of SEQ ID NO:1 or an amino acid sequence having at least 60% sequence identity to SEQ ID NO:1.

10. A method of treating a cancer according to claim 2 wherein the treatment involves induction of programmed cell death in cells expressing FGFR1.

11. A method of treating a cancer according to claim 2 wherein the cancer is a sarcoma or a carcinoma.

12. A method of treating a cancer according to claim 1, wherein the FGFR1 antibody binds FGFR1 at an epitope having at least 80% sequence identity to the amino acid sequence SSSEEKETDNTKPNR [SEQ ID NO:2].

13. A method of treating a cancer according to claim 1, wherein the FGFR1 antibody binds FGFR1 at an epitope consisting of the amino acid sequence SSSEEKETDNTKPNR [SEQ ID NO:2].

14. A method of treating a cancer according to claim 2, wherein the FGFR1 antibody binds FGFR1 at an epitope having at least 80% sequence identity to the amino acid sequence SSSEEKETDNTKPNR [SEQ ID NO:2].

15. A method of treating a cancer according to claim 2, wherein the FGFR1 antibody binds FGFR1 at an epitope consisting of the amino acid sequence SSSEEKETDNTKPNR [SEQ ID NO:2].

16. The method of claim 6, wherein the FGFR1 antibody binds FGFR1 at an epitope having at least 80% sequence identity to the amino acid sequence SSSEEKETDNTKPNR [SEQ ID NO:2].

17. The method of claim 6, wherein the FGFR1 antibody binds FGFR1 at an epitope consisting of the amino acid sequence SSSEEKETDNTKPNR [SEQ ID NO:2].

* * * * *

SEQUENCE LISTING

```
<160> NUMBER OF SEQ ID NOS: 9

<210> SEQ ID NO 1
<211> LENGTH: 822
<212> TYPE: PRT
<213> ORGANISM: Homo sapiens

<400> SEQUENCE: 1

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Ser Ser Ser Glu Glu Lys Glu Thr Asp Asn Thr
    130                 135                 140

Lys Pro Asn Arg Met Pro Val Ala Pro Tyr Trp Thr Ser Pro Glu Lys
145                 150                 155                 160

Met Glu Lys Lys Leu His Ala Val Pro Ala Ala Lys Thr Val Lys Phe
                165                 170                 175
```

-continued

```
Lys Cys Pro Ser Ser Gly Thr Pro Asn Pro Thr Leu Arg Trp Leu Lys
                180                 185                 190

Asn Gly Lys Glu Phe Lys Pro Asp His Arg Ile Gly Gly Tyr Lys Val
            195                 200                 205

Arg Tyr Ala Thr Trp Ser Ile Ile Met Asp Ser Val Val Pro Ser Asp
        210                 215                 220

Lys Gly Asn Tyr Thr Cys Ile Val Glu Asn Glu Tyr Gly Ser Ile Asn
225                 230                 235                 240

His Thr Tyr Gln Leu Asp Val Val Glu Arg Ser Pro His Arg Pro Ile
                245                 250                 255

Leu Gln Ala Gly Leu Pro Ala Asn Lys Thr Val Ala Leu Gly Ser Asn
            260                 265                 270

Val Glu Phe Met Cys Lys Val Tyr Ser Asp Pro Gln Pro His Ile Gln
        275                 280                 285

Trp Leu Lys His Ile Glu Val Asn Gly Ser Lys Ile Gly Pro Asp Asn
        290                 295                 300

Leu Pro Tyr Val Gln Ile Leu Lys Thr Ala Gly Val Asn Thr Thr Asp
305                 310                 315                 320

Lys Glu Met Glu Val Leu His Leu Arg Asn Val Ser Phe Glu Asp Ala
                325                 330                 335

Gly Glu Tyr Thr Cys Leu Ala Gly Asn Ser Ile Gly Leu Ser His His
            340                 345                 350

Ser Ala Trp Leu Thr Val Leu Glu Ala Leu Glu Arg Pro Ala Val
            355                 360                 365

Met Thr Ser Pro Leu Tyr Leu Glu Ile Ile Tyr Cys Thr Gly Ala
        370                 375                 380

Phe Leu Ile Ser Cys Met Val Gly Ser Val Ile Val Tyr Lys Met Lys
385                 390                 395                 400

Ser Gly Thr Lys Lys Ser Asp Phe His Ser Gln Met Ala Val His Lys
                405                 410                 415

Leu Ala Lys Ser Ile Pro Leu Arg Arg Gln Val Thr Val Ser Ala Asp
            420                 425                 430

Ser Ser Ala Ser Met Asn Ser Gly Val Leu Leu Val Arg Pro Ser Arg
        435                 440                 445

Leu Ser Ser Ser Gly Thr Pro Met Leu Ala Gly Val Ser Glu Tyr Glu
        450                 455                 460

Leu Pro Glu Asp Pro Arg Trp Glu Leu Pro Arg Asp Arg Leu Val Leu
465                 470                 475                 480

Gly Lys Pro Leu Gly Glu Gly Cys Phe Gly Gln Val Val Leu Ala Glu
                485                 490                 495

Ala Ile Gly Leu Asp Lys Asp Lys Pro Asn Arg Val Thr Lys Val Ala
            500                 505                 510

Val Lys Met Leu Lys Ser Asp Ala Thr Glu Lys Asp Leu Ser Asp Leu
        515                 520                 525

Ile Ser Glu Met Glu Met Met Lys Met Ile Gly Lys His Lys Asn Ile
        530                 535                 540

Ile Asn Leu Leu Gly Ala Cys Thr Gln Asp Gly Pro Leu Tyr Val Ile
545                 550                 555                 560

Val Glu Tyr Ala Ser Lys Gly Asn Leu Arg Glu Tyr Leu Gln Ala Arg
                565                 570                 575

Arg Pro Pro Gly Leu Glu Tyr Cys Tyr Asn Pro Ser His Asn Pro Glu
            580                 585                 590
```

```
Glu Gln Leu Ser Ser Lys Asp Leu Val Ser Cys Ala Tyr Gln Val Ala
            595                 600                 605

Arg Gly Met Glu Tyr Leu Ala Ser Lys Cys Ile His Arg Asp Leu
        610                 615                 620

Ala Ala Arg Asn Val Leu Val Thr Glu Asp Asn Val Met Lys Ile Ala
625                 630                 635                 640

Asp Phe Gly Leu Ala Arg Asp Ile His His Ile Asp Tyr Tyr Lys Lys
                645                 650                 655

Thr Thr Asn Gly Arg Leu Pro Val Lys Trp Met Ala Pro Glu Ala Leu
            660                 665                 670

Phe Asp Arg Ile Tyr Thr His Gln Ser Asp Val Trp Ser Phe Gly Val
                675                 680                 685

Leu Leu Trp Glu Ile Phe Thr Leu Gly Gly Ser Pro Tyr Pro Gly Val
            690                 695                 700

Pro Val Glu Glu Leu Phe Lys Leu Leu Lys Glu Gly His Arg Met Asp
705                 710                 715                 720

Lys Pro Ser Asn Cys Thr Asn Glu Leu Tyr Met Met Met Arg Asp Cys
                725                 730                 735

Trp His Ala Val Pro Ser Gln Arg Pro Thr Phe Lys Gln Leu Val Glu
            740                 745                 750

Asp Leu Asp Arg Ile Val Ala Leu Thr Ser Asn Gln Glu Tyr Leu Asp
                755                 760                 765

Leu Ser Met Pro Leu Asp Gln Tyr Ser Pro Ser Phe Pro Asp Thr Arg
            770                 775                 780

Ser Ser Thr Cys Ser Ser Gly Glu Asp Ser Val Phe Ser His Glu Pro
785                 790                 795                 800

Leu Pro Glu Glu Pro Cys Leu Pro Arg His Pro Ala Gln Leu Ala Asn
            805                 810                 815

Gly Gly Leu Lys Arg Arg
            820

<210> SEQ ID NO 2
<211> LENGTH: 15
<212> TYPE: PRT
<213> ORGANISM: Homo sapiens

<400> SEQUENCE: 2

Ser Ser Ser Glu Glu Lys Glu Thr Asp Asn Thr Lys Pro Asn Arg
1               5                   10                  15

<210> SEQ ID NO 3
<211> LENGTH: 18
<212> TYPE: PRT
<213> ORGANISM: Homo sapiens

<400> SEQUENCE: 3

Lys Met Glu Lys Lys Leu His Ala Val Pro Ala Ala Lys Thr Val Lys
1               5                   10                  15

Phe Lys

<210> SEQ ID NO 4
<211> LENGTH: 820
<212> TYPE: PRT
<213> ORGANISM: Homo sapiens
```

```
<400> SEQUENCE: 4

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
        275                 280                 285

Lys His Ile Glu Val Asn Gly Ser Lys Ile Gly Pro Asp Asn Leu Pro
    290                 295                 300

Tyr Val Gln Ile Leu Lys Thr Ala Gly Val Asn Thr Thr Asp Lys Glu
305                 310                 315                 320

Met Glu Val Leu His Leu Arg Asn Val Ser Phe Glu Asp Ala Gly Glu
                325                 330                 335

Tyr Thr Cys Leu Ala Gly Asn Ser Ile Gly Leu Ser His His Ser Ala
            340                 345                 350

Trp Leu Thr Val Leu Glu Ala Leu Glu Glu Arg Pro Ala Val Met Thr
        355                 360                 365

Ser Pro Leu Tyr Leu Glu Ile Ile Ile Tyr Cys Thr Gly Ala Phe Leu
    370                 375                 380

Ile Ser Cys Met Val Gly Ser Val Ile Val Tyr Lys Met Lys Ser Gly
385                 390                 395                 400

Thr Lys Lys Ser Asp Phe His Ser Gln Met Ala Val His Lys Leu Ala
                405                 410                 415
```

```
Lys Ser Ile Pro Leu Arg Arg Gln Val Thr Val Ser Ala Asp Ser Ser
            420                 425                 430

Ala Ser Met Asn Ser Gly Val Leu Leu Val Arg Pro Ser Arg Leu Ser
        435                 440                 445

Ser Ser Gly Thr Pro Met Leu Ala Gly Val Ser Glu Tyr Glu Leu Pro
    450                 455                 460

Glu Asp Pro Arg Trp Glu Leu Pro Arg Asp Arg Leu Val Leu Gly Lys
465                 470                 475                 480

Pro Leu Gly Glu Gly Cys Phe Gly Gln Val Val Leu Ala Glu Ala Ile
                485                 490                 495

Gly Leu Asp Lys Asp Lys Pro Asn Arg Val Thr Lys Val Ala Val Lys
            500                 505                 510

Met Leu Lys Ser Asp Ala Thr Glu Lys Asp Leu Ser Asp Leu Ile Ser
        515                 520                 525

Glu Met Glu Met Met Lys Met Ile Gly Lys His Lys Asn Ile Ile Asn
    530                 535                 540

Leu Leu Gly Ala Cys Thr Gln Asp Gly Pro Leu Tyr Val Ile Val Glu
545                 550                 555                 560

Tyr Ala Ser Lys Gly Asn Leu Arg Glu Tyr Leu Gln Ala Arg Arg Pro
                565                 570                 575

Pro Gly Leu Glu Tyr Cys Tyr Asn Pro Ser His Asn Pro Glu Glu Gln
            580                 585                 590

Leu Ser Ser Lys Asp Leu Val Ser Cys Ala Tyr Gln Val Ala Arg Gly
        595                 600                 605

Met Glu Tyr Leu Ala Ser Lys Lys Cys Ile His Arg Asp Leu Ala Ala
    610                 615                 620

Arg Asn Val Leu Val Thr Glu Asp Asn Val Met Lys Ile Ala Asp Phe
625                 630                 635                 640

Gly Leu Ala Arg Asp Ile His His Ile Asp Tyr Tyr Lys Lys Thr Thr
                645                 650                 655

Asn Gly Arg Leu Pro Val Lys Trp Met Ala Pro Glu Ala Leu Phe Asp
            660                 665                 670

Arg Ile Tyr Thr His Gln Ser Asp Val Trp Ser Phe Gly Val Leu Leu
        675                 680                 685

Trp Glu Ile Phe Thr Leu Gly Gly Ser Pro Tyr Pro Gly Val Pro Val
    690                 695                 700

Glu Glu Leu Phe Lys Leu Leu Lys Glu Gly His Arg Met Asp Lys Pro
705                 710                 715                 720

Ser Asn Cys Thr Asn Glu Leu Tyr Met Met Met Arg Asp Cys Trp His
                725                 730                 735

Ala Val Pro Ser Gln Arg Pro Thr Phe Lys Gln Leu Val Glu Asp Leu
            740                 745                 750

Asp Arg Ile Val Ala Leu Thr Ser Asn Gln Glu Tyr Leu Asp Leu Ser
        755                 760                 765

Met Pro Leu Asp Gln Tyr Ser Pro Ser Phe Pro Asp Thr Arg Ser Ser
    770                 775                 780

Thr Cys Ser Ser Gly Glu Asp Ser Val Phe Ser His Glu Pro Leu Pro
785                 790                 795                 800

Glu Glu Pro Cys Leu Pro Arg His Pro Ala Gln Leu Ala Asn Gly Gly
                805                 810                 815

Leu Lys Arg Arg
            820
```

```
<210> SEQ ID NO 5
<211> LENGTH: 47
<212> TYPE: PRT
<213> ORGANISM: Homo sapiens

<400> SEQUENCE: 5

His Ser Gly Ile Asn Ser Ser Asp Ala Glu Val Leu Thr Leu Phe Asn
1               5                   10                  15

Val Thr Glu Ala Gln Ser Gly Glu Tyr Val Cys Lys Val Ser Asn Tyr
            20                  25                  30

Ile Gly Glu Ala Asn Gln Ser Ala Trp Leu Thr Val Thr Arg Pro
        35                  40                  45

<210> SEQ ID NO 6
<211> LENGTH: 819
<212> TYPE: PRT
<213> ORGANISM: Homo sapiens

<400> SEQUENCE: 6

Met Trp Ser Trp Lys Cys Leu Leu Phe Trp Ala Val Leu Val Thr Ala
1               5                   10                  15

Thr Leu Cys Thr Ala Arg Pro Ser Pro Thr Leu Pro Glu Gln Ala Gln
            20                  25                  30

Pro Trp Gly Ala Pro Val Glu Val Glu Ser Phe Leu Val His Pro Gly
        35                  40                  45

Asp Leu Leu Gln Leu Arg Cys Arg Leu Arg Asp Asp Val Gln Ser Ile
    50                  55                  60

Asn Trp Leu Arg Asp Gly Val Gln Leu Ala Glu Ser Asn Arg Thr Arg
65                  70                  75                  80

Ile Thr Gly Glu Glu Val Glu Val Gln Asp Ser Val Pro Ala Asp Ser
                85                  90                  95

Gly Leu Tyr Ala Cys Val Thr Ser Ser Pro Ser Gly Ser Asp Thr Thr
            100                 105                 110

Tyr Phe Ser Val Asn Val Ser Asp Ala Leu Pro Ser Ser Glu Asp Asp
        115                 120                 125

Asp Asp Asp Asp Asp Ser Ser Ser Glu Glu Lys Glu Thr Asp Asn Thr
    130                 135                 140

Lys Pro Asn Pro Val Ala Pro Tyr Trp Thr Ser Pro Glu Lys Met Glu
145                 150                 155                 160

Lys Lys Leu His Ala Val Pro Ala Ala Lys Thr Val Lys Phe Lys Cys
                165                 170                 175

Pro Ser Ser Gly Thr Pro Asn Pro Thr Leu Arg Trp Leu Lys Asn Gly
            180                 185                 190

Lys Glu Phe Lys Pro Asp His Arg Ile Gly Gly Tyr Lys Val Arg Tyr
        195                 200                 205

Ala Thr Trp Ser Ile Ile Met Asp Ser Val Val Pro Ser Asp Lys Gly
    210                 215                 220

Asn Tyr Thr Cys Ile Val Glu Asn Glu Tyr Gly Ser Ile Asn His Thr
225                 230                 235                 240

Tyr Gln Leu Asp Val Val Glu Arg Ser Pro His Arg Pro Ile Leu Gln
                245                 250                 255

Ala Gly Leu Pro Ala Asn Lys Thr Val Ala Leu Gly Ser Asn Val Glu
            260                 265                 270

Phe Met Cys Lys Val Tyr Ser Asp Pro Gln Pro His Ile Gln Trp Leu
        275                 280                 285
```

```
Lys His Ile Glu Val Asn Gly Ser Lys Ile Gly Pro Asp Asn Leu Pro
    290                 295                 300

Tyr Val Gln Ile Leu Lys His Ser Gly Ile Asn Ser Ser Asp Ala Glu
305                 310                 315                 320

Val Leu Thr Leu Phe Asn Val Thr Glu Ala Gln Ser Gly Glu Tyr Val
                325                 330                 335

Cys Lys Val Ser Asn Tyr Ile Gly Glu Ala Asn Gln Ser Ala Trp Leu
                340                 345                 350

Thr Val Thr Arg Pro Ala Leu Glu Glu Arg Pro Ala Val Met Thr Ser
                355                 360                 365

Pro Leu Tyr Leu Glu Ile Ile Ile Tyr Cys Thr Gly Ala Phe Leu Ile
370                 375                 380

Ser Cys Met Val Gly Ser Val Ile Val Tyr Lys Met Lys Ser Gly Thr
385                 390                 395                 400

Lys Lys Ser Asp Phe His Ser Gln Met Ala Val His Lys Leu Ala Lys
                405                 410                 415

Ser Ile Pro Leu Arg Arg Gln Val Thr Val Ser Ala Asp Ser Ser Ala
                420                 425                 430

Ser Met Asn Ser Gly Val Leu Leu Val Arg Pro Ser Arg Leu Ser Ser
                435                 440                 445

Ser Gly Thr Pro Met Leu Ala Gly Val Ser Glu Tyr Glu Leu Pro Glu
                450                 455                 460

Asp Pro Arg Trp Glu Leu Pro Arg Asp Arg Leu Val Leu Gly Lys Pro
465                 470                 475                 480

Leu Gly Glu Gly Cys Phe Gly Gln Val Val Leu Ala Glu Ala Ile Gly
                485                 490                 495

Leu Asp Lys Asp Lys Pro Asn Arg Val Thr Lys Val Ala Val Lys Met
                500                 505                 510

Leu Lys Ser Asp Ala Thr Glu Lys Asp Leu Ser Asp Leu Ile Ser Glu
                515                 520                 525

Met Glu Met Met Lys Met Ile Gly Lys His Lys Asn Ile Ile Asn Leu
530                 535                 540

Leu Gly Ala Cys Thr Gln Asp Gly Pro Leu Tyr Val Ile Val Glu Tyr
545                 550                 555                 560

Ala Ser Lys Gly Asn Leu Arg Glu Tyr Leu Gln Ala Arg Arg Pro Pro
                565                 570                 575

Gly Leu Glu Tyr Cys Tyr Asn Pro Ser His Asn Pro Glu Glu Gln Leu
                580                 585                 590

Ser Ser Lys Asp Leu Val Ser Cys Ala Tyr Gln Val Ala Arg Gly Met
                595                 600                 605

Glu Tyr Leu Ala Ser Lys Lys Cys Ile His Arg Asp Leu Ala Ala Arg
610                 615                 620

Asn Val Leu Val Thr Glu Asp Asn Val Met Lys Ile Ala Asp Phe Gly
625                 630                 635                 640

Leu Ala Arg Asp Ile His His Ile Asp Tyr Tyr Lys Lys Thr Thr Asn
                645                 650                 655

Gly Arg Leu Pro Val Lys Trp Met Ala Pro Glu Ala Leu Phe Asp Arg
                660                 665                 670

Ile Tyr Thr His Gln Ser Asp Val Trp Ser Phe Gly Val Leu Leu Trp
                675                 680                 685

Glu Ile Phe Thr Leu Gly Gly Ser Pro Tyr Pro Gly Val Pro Val Glu
690                 695                 700
```

```
Glu Leu Phe Lys Leu Leu Lys Glu Gly His Arg Met Asp Lys Pro Ser
705                 710                 715                 720

Asn Cys Thr Asn Glu Leu Tyr Met Met Met Arg Asp Cys Trp His Ala
                725                 730                 735

Val Pro Ser Gln Arg Pro Thr Phe Lys Gln Leu Val Glu Asp Leu Asp
                740                 745                 750

Arg Ile Val Ala Leu Thr Ser Asn Gln Glu Tyr Leu Asp Leu Ser Met
                755                 760                 765

Pro Leu Asp Gln Tyr Ser Pro Ser Phe Pro Asp Thr Arg Ser Ser Thr
                770                 775                 780

Cys Ser Ser Gly Glu Asp Ser Val Phe Ser His Glu Pro Leu Pro Glu
785                 790                 795                 800

Glu Pro Cys Leu Pro Arg His Pro Ala Gln Leu Ala Asn Gly Gly Leu
                805                 810                 815

Lys Arg Arg

<210> SEQ ID NO 7
<211> LENGTH: 48
<212> TYPE: PRT
<213> ORGANISM: Homo sapiens

<400> SEQUENCE: 7

Thr Ala Gly Val Asn Thr Thr Asp Lys Glu Met Glu Val Leu His Leu
1               5                   10                  15

Arg Asn Val Ser Phe Glu Asp Ala Gly Glu Tyr Thr Cys Leu Ala Gly
                20                  25                  30

Asn Ser Ile Gly Leu Ser His His Ser Ala Trp Leu Thr Val Leu Glu
            35                  40                  45

<210> SEQ ID NO 8
<211> LENGTH: 16
<212> TYPE: PRT
<213> ORGANISM: Artificial sequence
<220> FEATURE:
<223> OTHER INFORMATION: Synthesized peptide

<400> SEQUENCE: 8

Cys Ser Ser Ser Glu Glu Lys Glu Thr Asp Asn Thr Lys Pro Asn Arg
1               5                   10                  15

<210> SEQ ID NO 9
<211> LENGTH: 19
<212> TYPE: PRT
<213> ORGANISM: Artificial sequence
<220> FEATURE:
<223> OTHER INFORMATION: Synthesized peptide

<400> SEQUENCE: 9

Lys His Leu Cys Ser Ser Ser Glu Glu Lys Glu Thr Asp Asn Thr Lys
1               5                   10                  15

Pro Asn Arg
```